US012590120B2

(12) United States Patent
Minden et al.

(10) Patent No.: US 12,590,120 B2
(45) Date of Patent: Mar. 31, 2026

(54) MATERIALS AND METHODS FOR ISOLATING SELF-ANTIGEN POLYPEPTIDES

(71) Applicants: Impact Proteomics, Pittsburgh, PA (US); UNIVERSITY OF PITTSBURGH—OF THE COMMONWEALTH SYSTEM OF HIGHER EDUCATION, Pittsburgh, PA (US)

(72) Inventors: Jonathan Minden, Pittsburgh, PA (US); Dana Ascherman, Pittsburgh, PA (US)

(73) Assignees: IMPACT PROTEOMICS, Pittsburgh, PA (US); UNIVERSITY OF PITTSBURGH—OF THE COMMONWEALTH SYSTEM OF HIGHER EDUCATION, Pittsburgh, PA (US)

(*) Notice: Subject to any disclaimer, the term of this patent is extended or adjusted under 35 U.S.C. 154(b) by 0 days.

(21) Appl. No.: 18/438,790

(22) Filed: Feb. 12, 2024

(65) Prior Publication Data

US 2024/0279272 A1     Aug. 22, 2024

Related U.S. Application Data

(60) Provisional application No. 63/486,090, filed on Feb. 21, 2023.

(51) Int. Cl.
| | |
|---|---|
| *C07K 1/22* | (2006.01) |
| *C07K 17/00* | (2006.01) |
| *C07K 19/00* | (2006.01) |
| *C12N 9/76* | (2006.01) |

(52) U.S. Cl.
CPC ................ *C07K 1/22* (2013.01); *C07K 17/00* (2013.01); *C07K 19/00* (2013.01); *C12N 9/6427* (2013.01); *C12Y 304/21004* (2013.01)

(58) Field of Classification Search
CPC .......... C07K 1/22; C07K 17/00; C07K 19/00; C12N 9/6427; C12Y 304/21004
See application file for complete search history.

(56) References Cited

U.S. PATENT DOCUMENTS

| | | | |
|---|---|---|---|
| 5,063,162 | A | 11/1991 | Kiefer |
| 5,945,515 | A | 8/1999 | Chomczynski |
| 6,508,957 | B2 | 1/2003 | Kunimoto et al. |
| 11,655,271 | B2 | 5/2023 | Minden et al. |
| 2004/0224344 | A1 | 11/2004 | Han et al. |
| 2010/0016545 | A1 | 1/2010 | Wiessler et al. |
| 2011/0313145 | A1 | 12/2011 | Sharon et al. |

(Continued)

FOREIGN PATENT DOCUMENTS

| | | |
|---|---|---|
| WO | 2007144200 A1 | 12/2007 |
| WO | 2019236988 A1 | 12/2019 |

OTHER PUBLICATIONS

Minden et al. Patient-specific Autoantigen Sample Preparation and Analysis Using the Reversible Protein Tag ProMTag. Abstract, May 2022, vol. 36, Issue S1 (Year: 2022).*

(Continued)

*Primary Examiner* — Shafiqul Haq
(74) *Attorney, Agent, or Firm* — K&L Gates LLP

(57) ABSTRACT

Materials and methods for isolating self-antigen polypeptides are provided.

19 Claims, 17 Drawing Sheets

(56) References Cited

U.S. PATENT DOCUMENTS

| | | |
|---|---|---|
| 2016/0235716 A1 | 8/2016 | Kesicki et al. |
| 2016/0370376 A1 | 12/2016 | Polukhtin et al. |
| 2019/0247513 A1 | 8/2019 | Robillard et al. |
| 2021/0253630 A1 | 8/2021 | Minden et al. |

OTHER PUBLICATIONS

Kang et al., "Tetrazine litigation for chemical proteomics", Proteome Science, 2017, pp. 1-13, vol. 15, No. 15.

Maier et al., "Acid-Labile Traceless Click Linker for Protein Transduction", J. Am. Chem. Soc. 2012, pp. 10169-10173, vol. 134, No. 24.

Van Buggenum et al., "A covalent and cleavable antibody-DNA conjugation strategy for sensitive protein detection via immuno-PCR", Scientific Reports, 2016, pp. 1-12, vol. 6, No. 22675.

Atassi et al., "[49] Reaction of Proteins with Citraconic Anhydride", Methods Enzymol., 1972, pp. 546-553, vol. 25.

Butler et al., "[14] Maleylation of Amino Groups", Methods Enzymol., 1972, pp. 191-199, vol. 25.

Devaraj et al., "Fast and Sensitive Pretargeted Labeling of Cancer Cells via Tetrazine/Trans-Cyclooctene Cycloaddition", Agnew Chem Int Ed Engl., 2009, pp. 7013-7016, vol. 48:38.

Karver et al., "Synthesis and Evaluation of a Series of 1,2,4,5-Tetrazines for Bioorthogonal Conjugation", Bioconjug Chem., 2011, pp. 2263-2270, vol. 22:11.

Kirby et al., "Structure and Efficiency in Intramolecular and Enzymic Catalysis. Catalysis of Amide Hydrolysis by the Carboxy-group of Substituted Maleamic Acids", Journal of the Chemical Society Perkin Transactions, 1972, pp. 1206-1214, vol. 2:9.

Klapper et al., "[46] Acylation with Dicarboxylic Acid Anhydrides", Methods Enzymol., 1972, pp. 531-536, vol. 25.

Oliveira et al., "Inverse electron demand Diels-Alder reactions in chemical biology", Chemical Society Reviews, 2012, pp. 1-57.

Biedka et al., "Multi-omics Sample Preparation Workflow for Proteins and DNA Using the Reversible Protein Tag ProMTag", US HUPO Conference, Chicago, p. 1, Mar. 6-7, 2023.

Minden et al., "Patient-specific autoantigen sample preparation and analysis using ProMTag", US HUPO Conference, Chicago, p. 1, Mar. 6-7, 2023.

Pubchem, Substance Record for SID 315355093, 2016, pp. 1-4. Retrieved from https://pubchem.ncbi.nlm.nih.gov/substance/315355093.

Biedka et al., "One-pot method for preparing DNA, RNA, and protein for multiomics analysis", Communications Biology, 7:324, pp. 1-12, 2024.

Ganesan, et al., "Immunoproteomics technologies in the discovery of autoantigens in autoimmune diseases", BioMol Concepts, Mar. 21, 2016, pp. 133-143.

Biedka, S. et al., Reversible Click Chemistry Tag for Universal Proteome Sample Preparation for Top-Down and Bottom-Up Analysis, Journal of Proteome Research, Oct. 1, 2021, Sep. 15, 2021, vol. 20, No. 10; pp. 4787-4800.

Biedka et al., Multi-omics Sample Preparation Workflow for Proteins and DNA Using the Reversible Protein Tag ProMTag, 1. Impact Proteomics, HUPO Conference, p. 1, Mar. 2022.

Minden et al., "Patient-specific autoantigen sample preparation and analysis using ProMTag", US HUPO Conference, p. 1, Mar. 2022.

Wallace, "Precipitation of Nucleic Acids", Methods in Enzymology, vol. 152, pp. 41-48.

* cited by examiner cell or tissue lysate compound 1 polypeptide

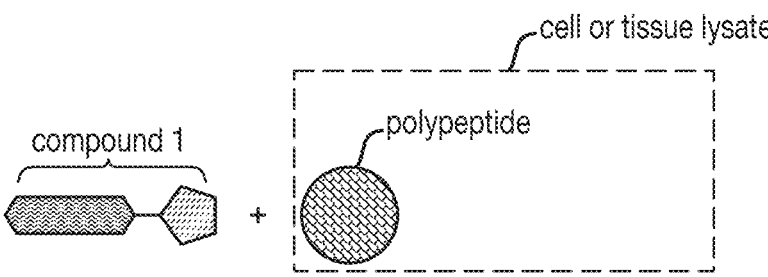

↓ polypeptide in a cell or tissue lysate bonds to compound 1 forming a mixed cell or tissue lysate comprising pH dependent tagged polypeptides

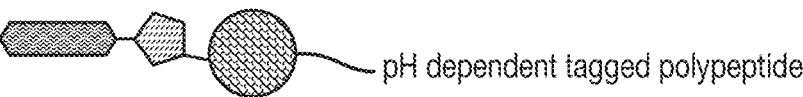

pH dependent tagged polypeptide

↓ couple tagged polypeptides to an antibody coupled substrate forming tagged polypeptides bound to the antibody coupled substrate

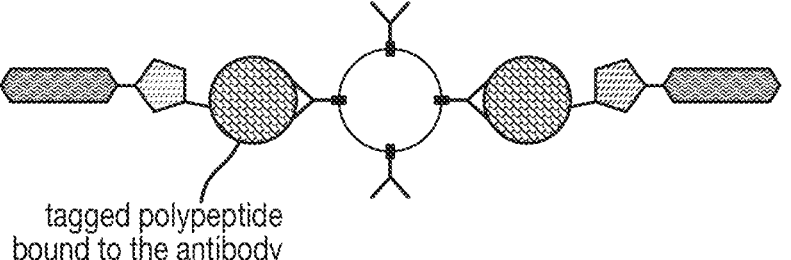

tagged polypeptide bound to the antibody coupled substrate

↓ wash away unbound protein and contaminants

↓ Elute tagged polypeptides forming tagged self-antigen polypeptides in an eluted sample

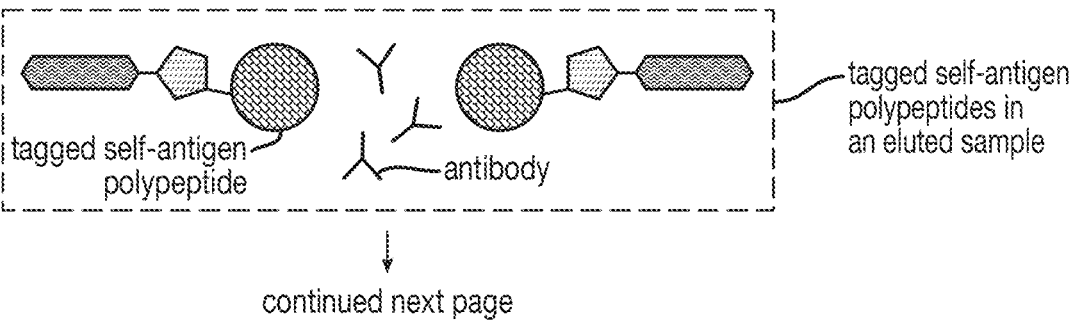

tagged self-antigen polypeptide antibody tagged self-antigen polypeptides in an eluted sample

↓

*FIG. 6* cell or tissue lysate

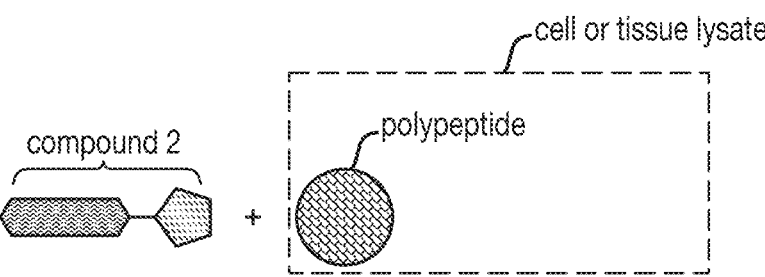

compound 2     +     polypeptide

↓ polypeptide in a cell or tissue lysate bonds to
compound 2 forming a mixed cell or tissue lysate
comprising permanently tagged polypeptides

permanently tagged polypeptide

↓ couple tagged polypeptides to an antibody coupled
substrate forming tagged polypeptides bound to the
antibody coupled substrate

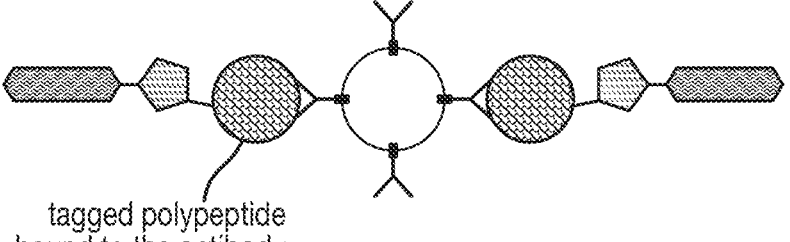

tagged polypeptide
bound to the antibody
coupled substrate

↓ wash away unbound protein and contaminants

↓ Elute tagged polypeptides forming tagged self-antigen
polypeptides in an eluted sample

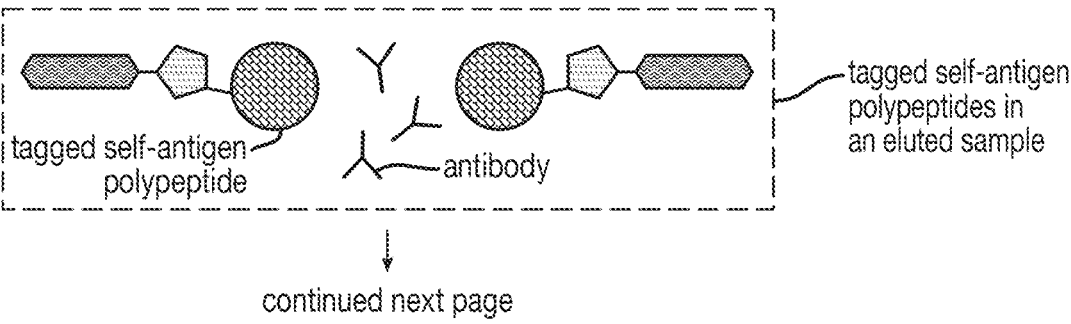

tagged self-antigen
polypeptide antibody tagged self-antigen
polypeptides in
an eluted sample

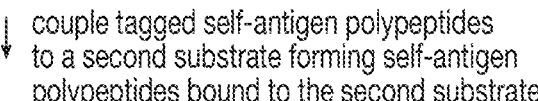

couple tagged self-antigen polypeptides
to a second substrate forming self-antigen
polypeptides bound to the second substrate

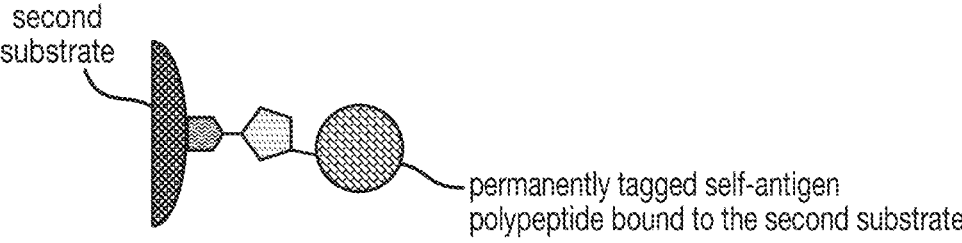

second
substrate permanently tagged self-antigen
polypeptide bound to the second substrate wash away untagged antibodies

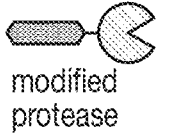

modified
protease add modified protease to permanently tagged self-antigen
polypeptide bound to the second substrate couple modified protease to second substrate
forming a modified protease bound to the second substrate

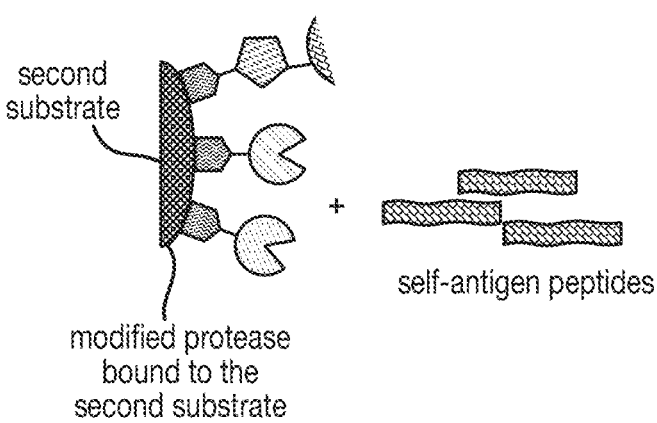

second
substrate

+ self-antigen peptides modified protease
bound to the
second substrate

*FIG. 7 (cont'd)*

| Normal Patient Serum Control | | | | | |
|---|---|---|---|---|---|
| Description | Log Prob. | Total Intensity | # of spectra | # of unique peptides | Coverage % |
| Albumin | 447.63 | 1.72E+09 | 197 | 69 | 78.82 |
| Complement C3 | 443.94 | 9.78E+08 | 211 | 85 | 54.66 |
| Vimentin | 338.95 | 1.05E+09 | 135 | 50 | 74.03 |
| Apolipoprotein B-100 | 224.01 | 1.62E+08 | 53 | 46 | 14.42 |
| CD5 antigen-like | 164.28 | 4.40E+08 | 72 | 22 | 72.05 |
| Alpha-2-macroglobulin | 84.98 | 8.10E+07 | 24 | 17 | 25.44 |
| Polyadenylate-binding protein 1 | 81.26 | 1.39E+08 | 27 | 15 | 30.66 |
| Tubulin beta chain | 69.21 | 4.70E+07 | 13 | 8 | 32.43 |
| Actin, cytoplasmic 2 | 56.92 | 1.37E+08 | 22 | 14 | 52.00 |
| Complement C4-B | 42.44 | 1.41E+07 | 5 | 4 | 3.10 |

FIG. 12A

| Anti-HSP90 Rabit polyclonal - HSP90-alpha expected | | | | | |
|---|---|---|---|---|---|
| Description | Log Prob. | Total Intensity | # of spectra | # of unique peptides | Coverage % |
| Isoform 2 of Heat shock protein HSP 90-alpha | 844.83 | 4.26E+09 | 492 | 125 | 61.73 |
| Vimentin | 677.79 | 4.32E+09 | 428 | 110 | 92.92 |
| Heat shock protein HSP 90-beta | 468.76 | 1.11E+09 | 208 | 68 | 52.62 |
| Actin, cytoplasmic 1 | 423.08 | 1.17E+09 | 179 | 56 | 77.07 |
| Albumin | 402.44 | 8.95E+08 | 139 | 55 | 70.94 |
| Tubulin beta chain | 386.28 | 7.92E+08 | 157 | 42 | 80.86 |
| Fatty acid synthase | 374.49 | 2.64E+08 | 75 | 53 | 34.81 |
| Isoform 3 of Plectin | 312.88 | 3.57E+08 | 95 | 64 | 18.64 |
| Polyadenylate-binding protein 1 | 300.77 | 6.24E+08 | 117 | 62 | 66.51 |

FIG. 12B

| Patient Serum 1 - Glycine tRNA ligase expected | | | | | |
|---|---|---|---|---|---|
| Description | Log Prob. | Total Intensity | # of spectra | # of unique peptides | Coverage % |
| Apolipoprotein B-100 | 413.86 | 5.46E+08 | 108 | 74 | 22.16 |
| Albumin | 389.03 | 1.96E+09 | 193 | 62 | 70.61 |
| Glycine-tRNA ligase | 384.67 | 1.80E+09 | 167 | 63 | 69.69 |
| Vimentin | 232.97 | 5.40E+08 | 81 | 44 | 74.89 |
| Complement C3 | 181.68 | 4.30E+08 | 78 | 43 | 32.05 |
| CD5 antigen-like | 160.45 | 9.13E+08 | 105 | 25 | 72.33 |
| Complement C4-B | 141.90 | 2.13E+08 | 26 | 20 | 19.04 |
| Keratin, type II cytoskeletal 8 | 85.05 | 1.13E+08 | 19 | 11 | 28.16 |
| Alpha-2-macroglobulin | 79.41 | 9.09E+07 | 21 | 17 | 15.81 |

FIG. 12C

| Patient Serum 2 - Topoisomerase 1 expected | | | | | |
|---|---|---|---|---|---|
| Description | Log Prob. | Total Intensity | # of spectra | # of unique peptides | Coverage % |
| Complement C3 | 451.95 | 1.31E+09 | 190 | 97 | 62.42 |
| Albumin | 371.47 | 1.29E+09 | 147 | 60 | 72.09 |
| Vimentin | 293.19 | 7.91E+08 | 127 | 48 | 80.04 |
| DNA topoisomerase 1 | 164.11 | 5.32E+08 | 80 | 44 | 44.31 |
| Complement C4-B | 147.37 | 1.46E+08 | 33 | 20 | 16.80 |
| CD5 antigen-like | 88.26 | 1.25E+08 | 23 | 13 | 62.82 |
| Polyadenylate-binding protein 1 | 85.22 | 1.35E+08 | 30 | 16 | 28.30 |
| Apolipoprotein B-100 | 83.80 | 1.17E+08 | 27 | 22 | 9.27 |
| Cystatin-C | 76.51 | 2.59E+08 | 48 | 16 | 72.60 |

FIG. 12D

| Patient Serum 3 - Alanine tRNA ligase expected | | | | | |
|---|---|---|---|---|---|
| Description | Log Prob. | Total Intensity | # of spectra | # of unique peptides | Coverage % |
| Alanine--tRNA ligase, cytoplasmic | 679.11 | 1.53E+09 | 227 | 101 | 77.07 |
| Albumin | 504.07 | 2.26E+09 | 250 | 86 | 81.94 |
| Vimentin | 369.18 | 1.02E+09 | 132 | 57 | 82.40 |
| Complement C3 | 354.78 | 6.60E+08 | 125 | 64 | 44.38 |
| Apolipoprotein B-100 | 181.54 | 1.71E+08 | 50 | 40 | 13.87 |
| Alpha-2-macroglobulin | 174.88 | 2.25E+08 | 48 | 31 | 28.83 |
| Complement C4-B | 157.54 | 3.26E+08 | 56 | 28 | 17.37 |
| CD5 antigen-like | 126.47 | 3.54E+08 | 49 | 18 | 71.76 |
| Actin, cytoplasmic 2 | 119.63 | 1.83E+08 | 34 | 19 | 60.53 |

FIG. 12E

| Patient Serum 4 - Topoisomerase 1 expected | | | | | |
|---|---|---|---|---|---|
| Description | Log Prob. | Total Intensity | # of spectra | # of unique peptides | Coverage % |
| Vimentin | 369.29 | 2.18E+09 | 213 | 66 | 80.90 |
| Albumin | 350.79 | 1.66E+09 | 174 | 57 | 65.85 |
| DNA topoisomerase 1 | 215.99 | 7.26E+08 | 99 | 47 | 49.41 |
| CD5 antigen-like | 190.55 | 9.19E+08 | 120 | 30 | 76.66 |
| Complement C3 | 138.99 | 4.10E+08 | 63 | 44 | 35.84 |
| Dihydrolipoyllysine-residue acetyltransferase | 135.73 | 3.24E+08 | 59 | 27 | 46.21 |
| Actin, cytoplasmic 2 | 122.25 | 1.58E+08 | 28 | 18 | 54.93 |
| Alpha-2-macroglobulin | 109.85 | 1.48E+08 | 30 | 24 | 27.68 |
| Nuclear pore membrane glycoprotein 210 | 96.67 | 1.43E+08 | 32 | 25 | 23.85 |

FIG. 12F

MATERIALS AND METHODS FOR ISOLATING SELF-ANTIGEN POLYPEPTIDES

CROSS-REFERENCE AND STATEMENT OF PRIORITY

The present application claims priority to U.S. Provisional Patent Application Ser. No. 63/486,090, filed Feb. 21, 2023, which is incorporated herein by reference in its entirety.

FIELD OF USE

The present disclosure relates to materials and methods for isolating self-antigen polypeptides.

BACKGROUND

Autoimmune diseases affect >20 million people in the US today. Currently, disease-specific autoantibodies are thought to be the best biomarkers for diagnosis. Conventional immunoprecipitation methods have been used to identify autoantigens from the most common autoimmune diseases. However, these diseases account for only 6.5 million of the 20 million patients suffering from autoimmune diseases, leaving many without diagnoses until irreversible damage occurs. The remaining 13.5 million patients have >70 autoimmune disorders without well-characterized autoantibodies. The state-of-the-art diagnostic test of these remaining diseases relies on gel electrophoresis of immunoprecipitated, radiolabeled proteins, which can be difficult to identify by mass spectrometry due to radiolabeling and the overwhelming presence of immunoglobulins.

Currently, there are challenges with materials and methods for safely isolating and identifying self-antigen polypeptides.

SUMMARY

Provided herein is a method of isolating self-antigen polypeptides. The method comprises: coupling antibodies from a first sample to a first substrate, thereby forming an antibody coupled substrate; mixing a second sample with a compound, thereby forming a mixed sample comprising tagged polypeptides, wherein the compound comprises a first moiety comprising a first member of a bio-orthogonal coupling pair, wherein the first member is configured to form a covalent bond with a second member of a bio-orthogonal coupling pair, a second moiety configured to form a pH dependent covalent bond with a polypeptide, and a linker linking the first moiety and the second moiety; coupling the tagged polypeptides in the mixed sample to the antibody coupled substrate, thereby forming tagged polypeptides bound to the antibody coupled substrate; eluting the tagged polypeptides bound to the antibody coupled substrate, thereby forming tagged self-antigen polypeptides in an eluted sample; coupling the tagged self-antigen polypeptides in the eluted sample to a second member of a bio-orthogonal coupling pair, wherein the second member of the bio-orthogonal coupling pair is linked to a second substrate, thereby forming self-antigen polypeptides bound to the second substrate; and eluting the self-antigen polypeptides bound to a second substrate in an elution buffer having a pH more acidic than a pH of the mixed sample by reversing the pH dependent covalent bond between the self-antigen polypeptides and the second moiety.

Also provided herein is a method of isolating self-antigen polypeptides. The method comprises: mixing a second sample with a compound, thereby forming a mixed sample comprising tagged polypeptides, wherein the compound comprises a first moiety comprising a first member of a bio-orthogonal coupling pair, wherein the first member is configured to form a covalent bond with a second member of a bio-orthogonal coupling pair, a second moiety configured to form a pH dependent covalent bond with a polypeptide, and a linker linking the first moiety and the second moiety; coupling the tagged polypeptides in the mixed sample to an antibody coupled substrate, thereby forming tagged polypeptides bound to the antibody coupled substrate, wherein the antibody coupled substrate comprises antibodies from a first sample coupled to a first substrate; eluting the tagged polypeptides bound to the antibody coupled substrate, thereby forming tagged self-antigen polypeptides in an eluted sample; coupling the tagged self-antigen polypeptides in the eluted sample to the second member of a bio-orthogonal coupling pair, wherein the second member of the bio-orthogonal coupling pair is linked to a second substrate, thereby forming self-antigen polypeptides bound to the second substrate; and eluting the self-antigen polypeptides bound to the second substrate in an elution buffer having a pH more acidic than a pH of the mixed sample by reversing the pH dependent covalent bond between the self-antigen polypeptides and the second moiety.

Also provided herein is a method of isolating self-antigen polypeptides. The method comprises: coupling tagged polypeptides in a mixed sample to an antibody coupled substrate, thereby forming tagged polypeptides bound to the antibody coupled substrate, wherein the antibody coupled substrate comprises antibodies from a first sample coupled to a first substrate, and wherein the mixed sample comprising tagged polypeptides is a mixture of a compound and a second sample, the compound comprising a first moiety comprising a first member of a bio-orthogonal coupling pair, wherein the first member is configured to form a covalent bond with a second member of a bio-orthogonal coupling pair, a second moiety configured to form a pH dependent covalent bond with a polypeptide, and a linker linking the first moiety and the second moiety; eluting the tagged polypeptides bound to the antibody coupled substrate, thereby forming tagged self-antigen polypeptides in an eluted sample; coupling the tagged self-antigen polypeptides in the eluted sample to the second member of a bio-orthogonal coupling pair, wherein the second member of the bio-orthogonal coupling pair is linked to a second substrate, thereby forming self-antigen polypeptides bound to the second substrate; and eluting the self-antigen polypeptides bound to the second substrate in an elution buffer having a pH more acidic than a pH of the mixed sample by reversing the pH dependent covalent bond between the self-antigen polypeptides and the second moiety.

Also provided herein is a method of isolating self-antigen polypeptides. The method comprises: coupling antibodies from a first sample to a first substrate, thereby forming an antibody coupled substrate; mixing a second sample with a compound, thereby forming a mixed sample comprising tagged polypeptides, wherein the compound comprises a first moiety comprising a first member of a bio-orthogonal coupling pair, wherein the first member is configured to form a covalent bond with a second member of a bio-orthogonal coupling pair, a second moiety configured to form a covalent bond with a polypeptide, and a linker linking the first moiety and the second moiety; coupling the tagged polypeptides in the mixed sample to the antibody coupled substrate, thereby forming tagged polypeptides bound to the antibody coupled substrate; eluting the tagged polypeptides bound to the antibody coupled substrate, thereby forming tagged self-antigen polypeptides in an eluted sample; coupling the tagged self-antigen polypeptides in the eluted sample to a second member of a bio-orthogonal coupling pair, wherein the second member of the bio-orthogonal coupling pair is linked to a second substrate, thereby forming self-antigen polypeptides bound to the second substrate; adding a modified protease to the self-antigen polypeptides bound to the second substrate, thereby forming self-antigen peptides, wherein the modified protease comprises a protease, and a first member of a bio-orthogonal coupling pair attached to the protease, wherein the first member is configured to form a covalent bond with a second member of a bio-orthogonal coupling pair; coupling the modified protease to the second member of a bio-orthogonal coupling pair, wherein the second member of the bio-orthogonal coupling pair is linked to the second substrate; and eluting the self-antigen peptides.

Also provided herein is a method of isolating self-antigen polypeptides. The method comprises: mixing a second sample with a compound, thereby forming a mixed sample comprising tagged polypeptides, wherein the compound comprises a first moiety comprising a first member of a bio-orthogonal coupling pair, wherein the first member is configured to form a covalent bond with a second member of a bio-orthogonal coupling pair, a second moiety configured to form a covalent bond with a polypeptide, and a linker linking the first moiety and the second moiety; coupling the tagged polypeptides in the mixed sample to an antibody coupled substrate, thereby forming tagged polypeptides bound to the antibody coupled substrate, wherein the antibody coupled substrate comprises antibodies from a first sample coupled to a first substrate; eluting the tagged polypeptides bound to the antibody coupled substrate, thereby forming tagged self-antigen polypeptides in an eluted sample; coupling the tagged self-antigen polypeptides in the eluted sample to the second member of a bio-orthogonal coupling pair, wherein the second member of the bio-orthogonal coupling pair is linked to a second substrate, thereby forming self-antigen polypeptides bound to the second substrate; adding a modified protease to the self-antigen polypeptides bound to the second substrate, thereby forming self-antigen peptides, wherein the modified protease comprises a protease, and a first member of a bio-orthogonal coupling pair attached to the protease, wherein the first member is configured to form a covalent bond with a second member of a bio-orthogonal coupling pair; coupling the modified protease to the second member of a bio-orthogonal coupling pair, wherein the second member of the bio-orthogonal coupling pair is linked to the second substrate; and eluting the self-antigen peptides.

Also provided herein is a method of isolating self-antigen polypeptides. The method comprises coupling tagged polypeptides in a mixed sample to an antibody coupled substrate, thereby forming tagged polypeptides bound to the antibody coupled substrate, wherein the antibody coupled substrate comprises antibodies from a first sample coupled to a first substrate, and wherein the mixed sample comprising tagged polypeptides is a mixture of a compound and a second sample, the compound comprising a first moiety comprising a first member of a bio-orthogonal coupling pair, wherein the first member is configured to form a covalent bond with a second member of a bio-orthogonal coupling pair, a second moiety configured to form a covalent bond with a polypeptide, and a linker linking the first moiety and the second moiety; eluting the tagged polypeptides bound to the antibody coupled substrate, thereby forming tagged self-antigen polypeptides in an eluted sample; coupling the tagged self-antigen polypeptides in the eluted sample to the second member of a bio-orthogonal coupling pair, wherein the second member of the bio-orthogonal coupling pair is linked to a second substrate, thereby forming self-antigen polypeptides bound to the second substrate; adding a modified protease to the self-antigen polypeptides bound to the second substrate, thereby forming self-antigen peptides, wherein the modified protease comprises a protease, and a first member of a bio-orthogonal coupling pair attached to the protease, wherein the first member is configured to form a covalent bond with a second member of a bio-orthogonal coupling pair; coupling the modified protease to the second member of a bio-orthogonal coupling pair, wherein the second member of the bio-orthogonal coupling pair is linked to the second substrate; and eluting the self-antigen peptides.

Also provided herein is a self-antigen isolation kit. The self-antigen isolation kit comprises a compound comprising a first moiety comprising a first member of a bio-orthogonal coupling pair, wherein the first moiety is configured to form a covalent bond with a second member of a bio-orthogonal coupling pair, a second moiety configured to form a pH dependent covalent bond with a polypeptide, and a linker linking the first moiety and the second moiety; a first substrate configured to couple antibodies from serum or plasma of a first sample, wherein the first substrate is used to isolate polypeptides having an affinity to antibodies coupled to the first substrate; and a second substrate linked to a second member of a bio-orthogonal coupling pair, wherein the second substrate is used to isolate self-antigen polypeptides bonded to the compound.

Also provided herein is a self-antigen isolation kit. The self-antigen isolation kit comprises a compound comprising a first moiety comprising a first member of a bio-orthogonal coupling pair, wherein the first moiety is configured to form a covalent bond with a second member of a bio-orthogonal coupling pair, a second moiety configured to form a covalent bond with a polypeptide, and a linker linking the first moiety and the second moiety; a first substrate configured to couple antibodies from serum or plasma of a first sample, wherein the first substrate is used to isolate polypeptides having an affinity to antibodies coupled to the first substrate; a second substrate linked to a second member of a bio-orthogonal coupling pair, wherein the second substrate is used to isolate self-antigen polypeptides bonded to the compound; and a modified protease comprising a protease, and a first member of a bio-orthogonal coupling pair attached to the protease, wherein the first member is configured to form a covalent bond with a second member of a bio-orthogonal coupling pair.

It is understood that the inventions disclosed and described in this specification are not limited to the aspects summarized in this Summary. The reader will appreciate the foregoing details, as well as others, upon considering the following detailed description of various non-limiting and non-exhaustive aspects according to this specification.

BRIEF DESCRIPTION OF THE DRAWINGS

Various aspects of the materials and methods disclosed and described in this specification can be better understood by reference to the accompanying figures, in which:

FIG. 1A shows compound 1 comprising a first moiety, a linker, and a second moiety configured to form a pH dependent covalent bond with a polypeptide. FIG. 1B shows compound 1 and a polypeptide forming a pH dependent tagged polypeptide;

FIG. 3A shows compound 2 comprising a first moiety, a linker, and a second moiety configured to form a covalent bond with a polypeptide. FIG. 3B shows compound 2 and a polypeptide forming a permanently tagged polypeptide;

FIG. 7 shows a schematic of a non-limiting method of isolating self-antigen polypeptides when using compound 2 for tagging polypeptides in a sample;

FIG. 12A is a table serving as a negative control and listing antigens identified by the method of isolating self-antigen polypeptides disclosed herein using an antibody coupled substrate comprising antibodies from serum of a healthy person;

FIG. 12B is a table serving as a positive control and listing antigens identified by the method of isolating self-antigen polypeptides disclosed herein using an antibody coupled substrate comprising anti-Hsp90 antibodies;

FIG. 12C is a table listing antigens and autoantigens identified by the method of isolating self-antigen polypeptides disclosed herein using an antibody coupled substrate comprising antibodies from serum of autoimmune patient #1;

FIG. 12D is a table listing antigens and autoantigens identified by the method of isolating self-antigen polypeptides disclosed herein using an antibody coupled substrate comprising antibodies from serum of autoimmune patient #2;

FIG. 12E is a table listing antigens and autoantigens identified by the method of isolating self-antigen polypeptides disclosed herein using an antibody coupled substrate comprising antibodies from serum of autoimmune patient #3;

FIG. 12F is a table listing antigens and autoantigens identified by the method of isolating self-antigen polypeptides disclosed herein using an antibody coupled substrate comprising antibodies from serum of autoimmune patient #4;

DETAILED DESCRIPTION OF NON-LIMITING EMBODIMENTS

Disclosed herein are methods of isolating and identifying self-antigen polypeptides.

In one aspect of the present disclosure, methods of isolating self-antigen polypeptides require compounds comprising a first moiety, a linker, and a second moiety.

Figure 1A:
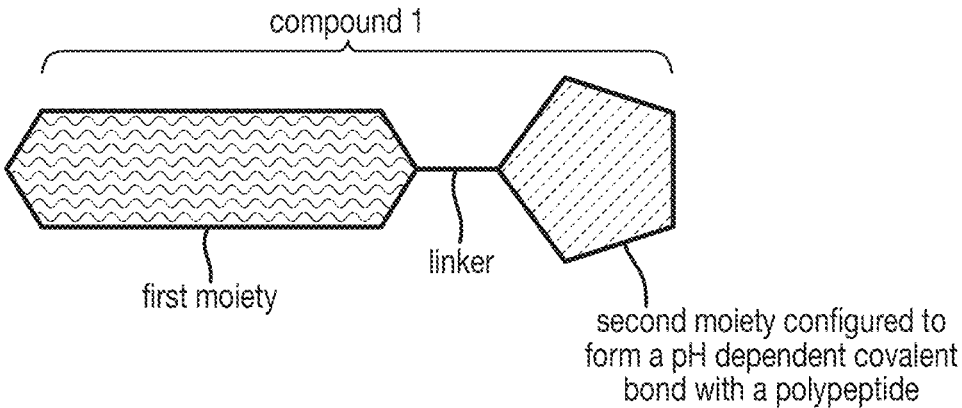
FIGS. 1A and 1B illustrate the formation of a pH dependent tagged polypeptide.
Figure 1B:
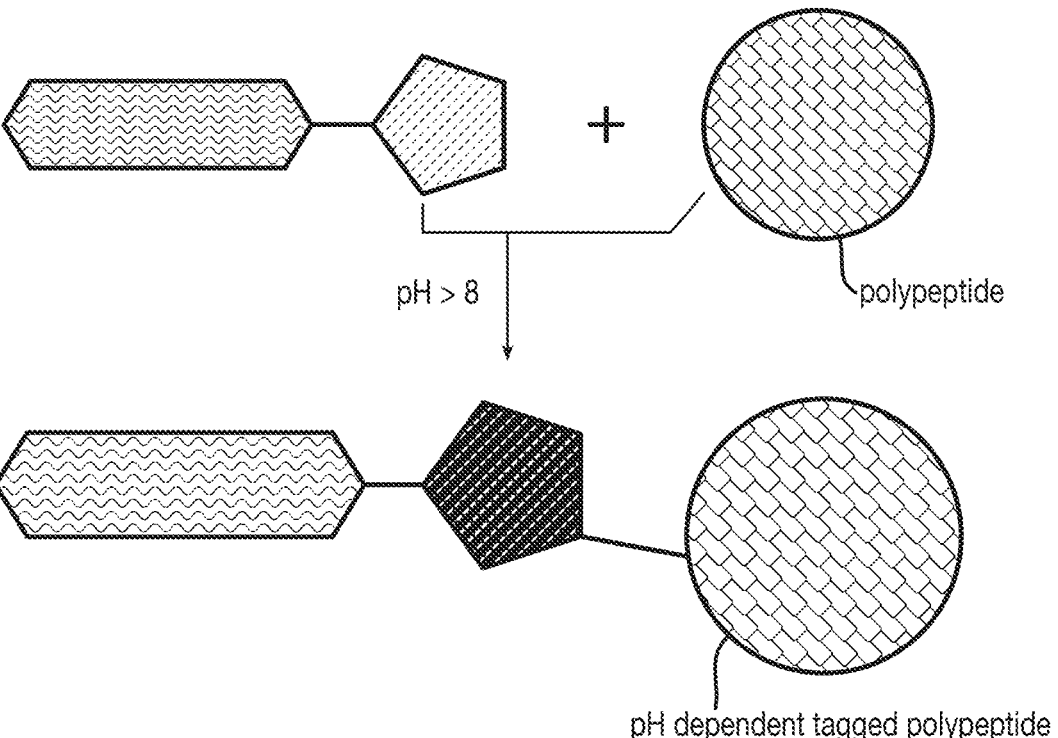
Figure 2:
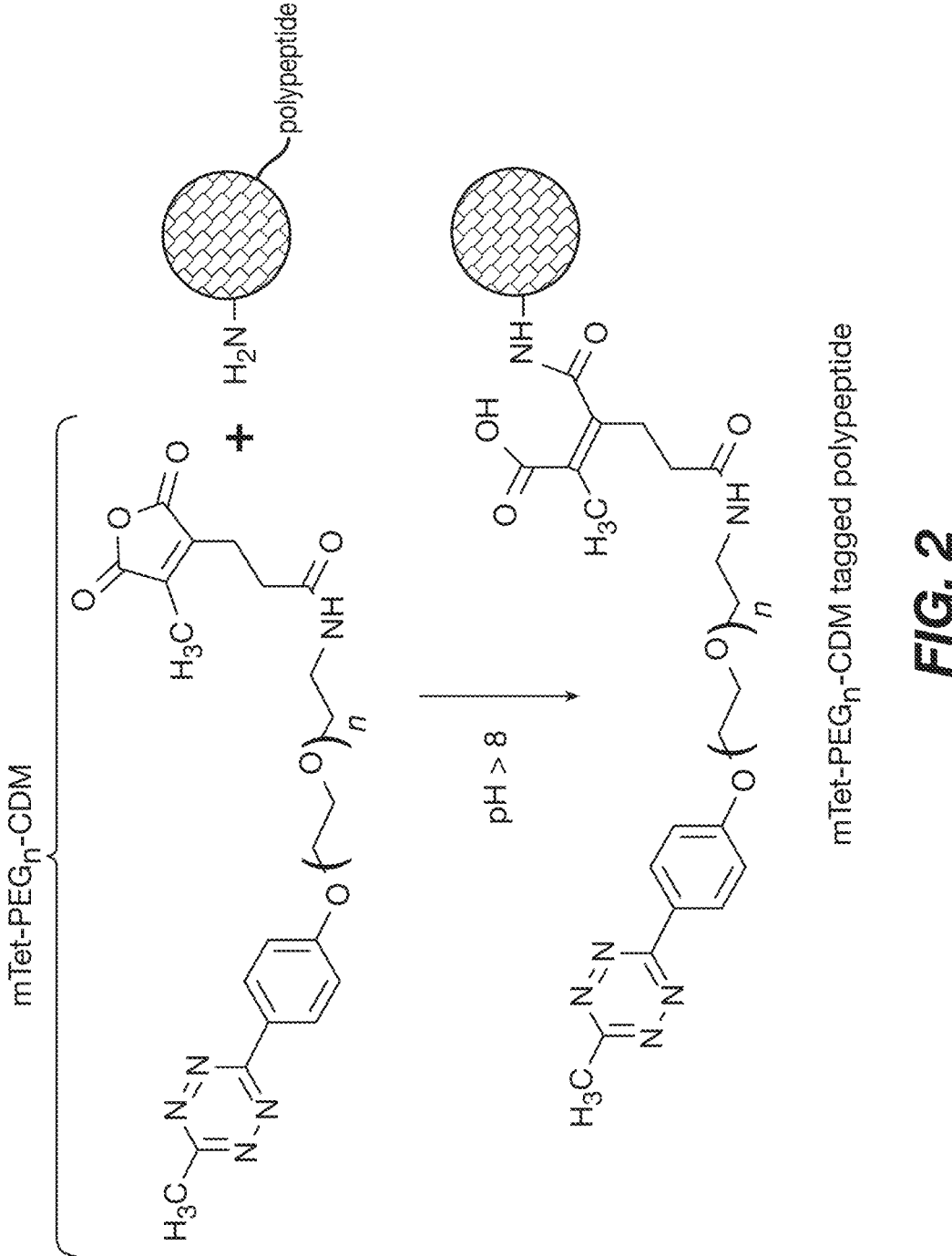
FIG. 2 shows an example of compound 1 (e.g. mTet-PEG$_n$-CDM) and a polypeptide forming a pH dependent tagged polypeptide (e.g. mTet-PEG$_n$-CDM tagged polypeptide)

In certain embodiments, the second moiety of the disclosed compounds can be configured to form a pH dependent covalent bond with polypeptides. These compounds are referred to herein as "compound 1" and illustrated in FIG. 1A. Compound 1 can form a pH dependent covalent bond with a polypeptide thereby forming a pH dependent tagged polypeptide, as illustrated in FIG. 1B. In certain embodiments, the second moiety of compound 1 can comprise a dicarboxylic acid anhydride moiety. In certain other embodiments, the dicarboxylic acid anhydride moiety can be a maleic anhydride moiety. In certain other embodiments, the dicarboxylic acid anhydride moiety can be a 2-(2'-carboxyethyl) maleic anhydride moiety. In certain embodiments, the compound can be mTet-PEG$_n$-CDM and form a pH dependent covalent bond with a polypeptide thereby forming a mTet-PEG$_n$-CDM tagged polypeptide, as illustrated in FIG. 2.

Compound 1 can be bonded to a polypeptide by formation of an amide bond between the dicarboxylic anhydride of the compound and primary amines of the polypeptide. The reaction of the dicarboxylic anhydride moiety with primary amines of a polypeptide can result in the formation of an acid-labile amide bond, which can only be cleaved by mild acids (e.g. acids with a pH ranging from >2 to 6).

An embodiment of Compound 1 is described in WO 2019/236988, which is incorporated herein by reference in its entirety.

Figure 3A:
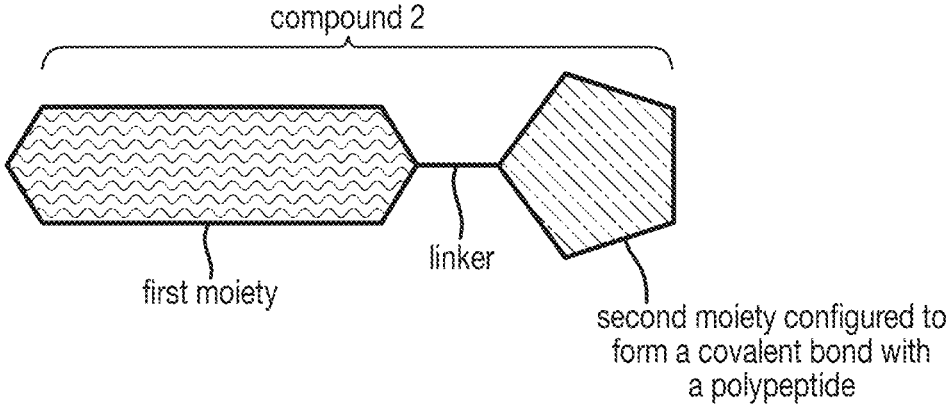
FIGS. 3A and 3B illustrate the formation of a permanently tagged polypeptide.
Figure 3B:
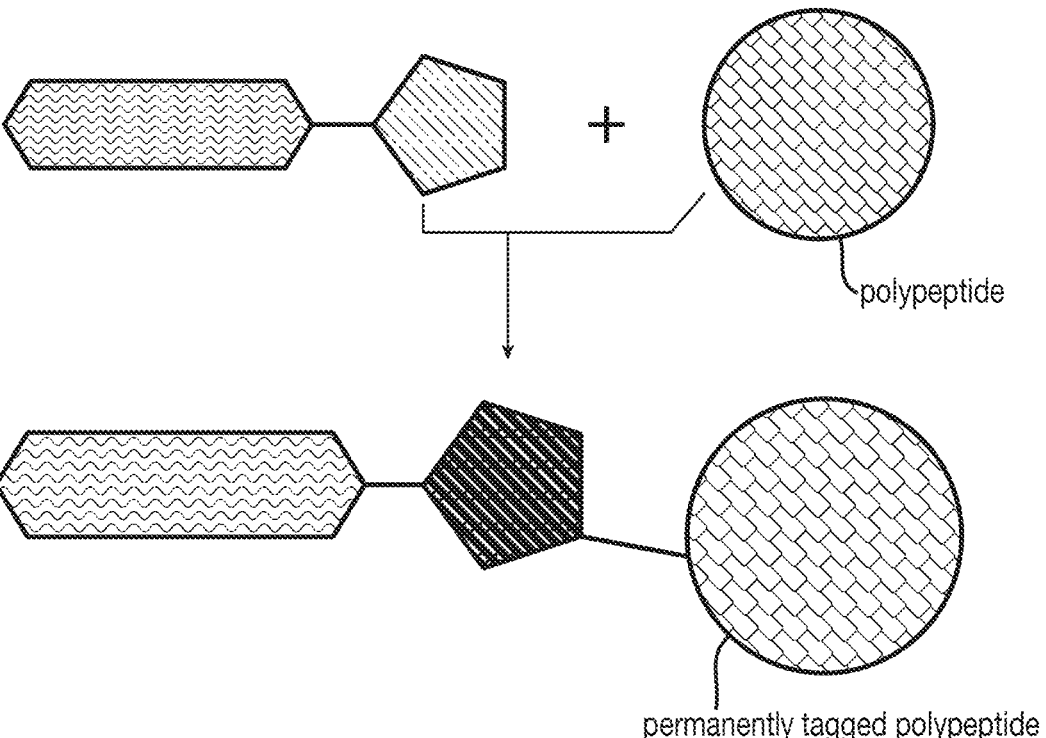
Figure 4:
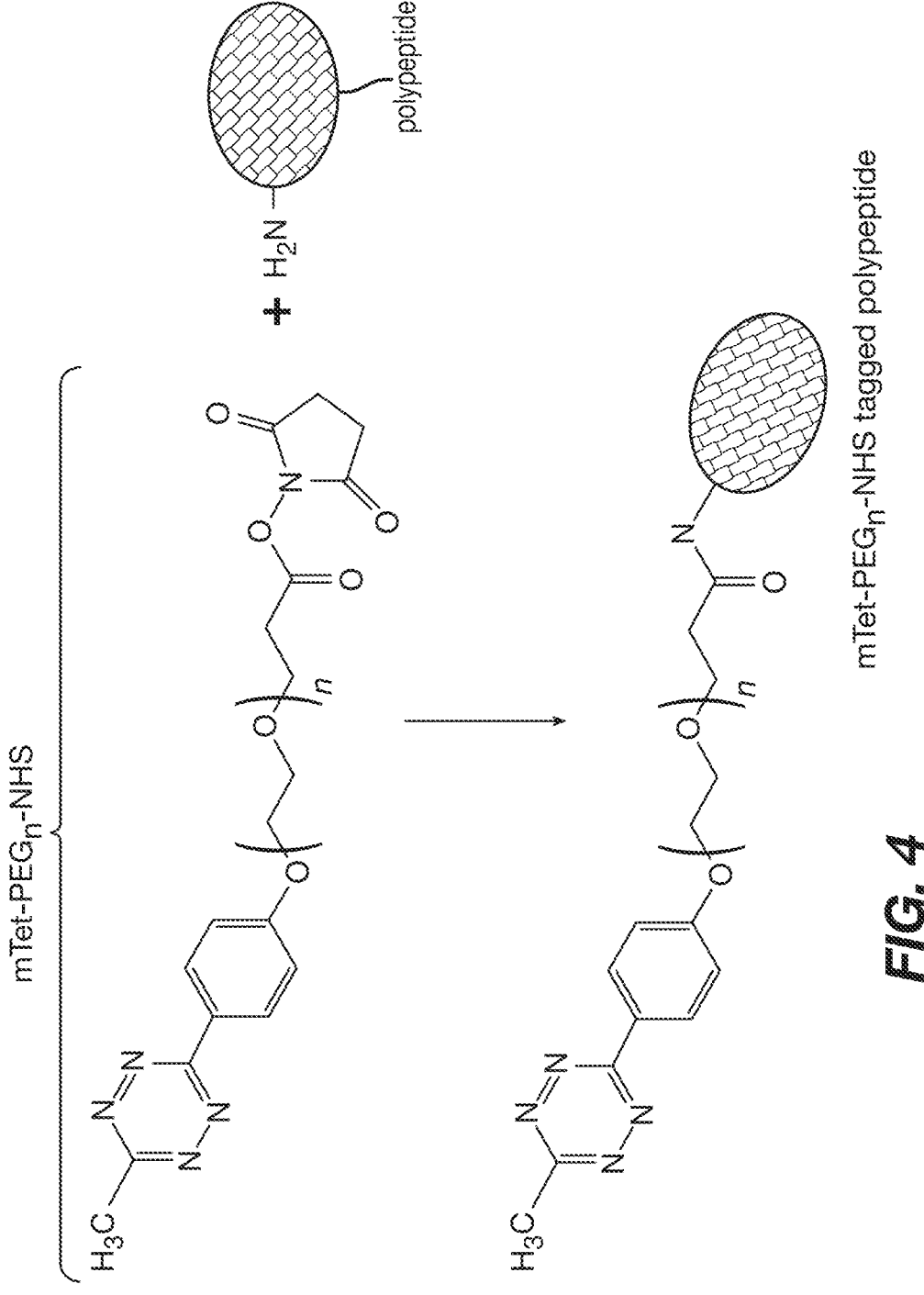
FIG. 4 shows an example of compound 2 (e.g. mTet-PEG$_n$-NHS) and a polypeptide forming a permanently tagged polypeptide (e.g. mTet-PEG$_n$-NHS tagged polypeptide)

In certain embodiments, the second moiety of the disclosed compounds can be configured to form a covalent bond with polypeptides. These compounds are referred to herein as "compound 2" and illustrated in FIG. 3A. Compound 2 can form a permanent covalent bond with a polypeptide thereby forming a permanently tagged polypeptide, as illustrated in FIG. 3B. In certain embodiments, the second moiety of compound 2 can comprise a N-hydroxysuccinimide moiety. In certain embodiments, the compound can be mTet-PEG$_n$-NHS and form a covalent bond with a polypeptide thereby forming a mTet-PEG$_n$-NHS tagged polypeptide, as illustrated in FIG. 4.

"Click Chemistry" describes reactions that are high yielding, wide in scope, create only byproducts that can be removed without chromatography, are stereospecific, simple to perform, and can be conducted in easily removable or benign solvents. In the context of the present disclosure a click chemistry reaction is biorthogonal, meaning it is sufficiently selective that it can be performed reliably even in a complex biological environment. These reactions may proceed efficiently in the presence of the multitude of functional groups found in living systems such nucleophiles, electrophiles, reductants, oxidants, and water. Simultaneously, these reactions should have a minimal impact on the biology itself.

In the context of bio-orthogonal reactions, e.g., a bio-orthogonal click chemistry reaction, relies on bond formation between molecules or moieties not found in natural compounds, referred to herein as bio-orthogonal coupling pairs. Such reactions can be selective over other potential reactive functional groups present on biomolecules, proceed in aqueous media at near physiological pH, and have fast reaction rates at room temperature (or up to 37° C.) using low reactant concentrations, which can ensure high modification efficiency (Lopes Bernardes, G., Oliveira, B., & Guo, Z. 2017. Inverse electron demand Diels-Alder reactions in chemical biology. Chemical Society Reviews https://doLorg/10.17863/CAM.10698). Bio-orthogonal reaction reagents (bio-orthogonal coupling pairs) do not react with natural cellular products, such as proteins or nucleic acids. Coupling occurs under a wide range of aqueous conditions and are stable once formed. In one embodiment, the bio-orthogonal reaction can be an inverse-electron-demand Diels-Alder reaction (IEDDA, e.g., inverse electron demand [4+2] Diels-Alder cycloaddition), in which an electron-rich dienophile reacts (e.g., a strained alkene) with an electron-poor diene (e.g., a tetrazine such as a 1,2,4,5-tetrazine or a 4-(1,2,4,5-tetrazinyl)phenyl moiety such as 4-(1,2,4,5-tetrazin-3-yl)phenyl, 6-alkyl-1,2,4,5-tetrazine, 6-pyridin-2-yl-1,2,4,5-tetrazine, 6-pyrimidin-2-yl-1,2,4,5-tetrazine, 4-(6-alkyl-1,2,4,5-tetrazin-3-yl)phenyl, 4-(6-pyridin-2-yl-1,2,4,5-tetrazin-3-yl)phenyl, or 4-(6-pyrimidin-2-yl-1,2,4,5-tetrazin-3-yl)phenyl, where alkyl may be a $C_{1-4}$ alkyl group) (see, e.g., Karver, M R, et al., Synthesis and Evaluation of a Series of 1,2,4,5-tetrazines for Bio-orthogonal Conjugation. *Bioconjug Chem.* 2011 Nov. 16; 22(11):2263-2270) in contrast to a normal electron demand Diels-Alder reaction, where an electron-rich diene reacts with an electron-poor dienophile (see, e.g., Lopes Bernardes, G., Oliveira, B., & Guo, Z. 2017. Chemical Society Reviews https://doi.org/10.17863/CAM.10698 for further details, as well as providing examples of other bio-orthogonal reactions). Of note "1,2,4,5-tetrazine" refers to the precise 1,2,4,5-tetrazine compound or a 1,2,4,5-tetrazinyl moiety, while "a 1,2,4,5-tetrazine" refers to a compound or moiety comprising the 1,2,4,5-tetrazinyl moiety. In another example, the bio-orthogonal coupling pair is an alkyne-azide coupling pair, such as a propargyl moiety and an azido moiety, as are broadly-known.

In IEDDA reactions, Electron-poor dienes, such as 1,2,4,5-tetrazines, are reacted with an electron-rich dienophile, for example, a strained dienophile, and fine-tuning the choice of electron-poor diene and electron-rich dienophile ("IEDDA coupling pair") can be used to tailor the reaction kinetics (Id.). Non-limiting examples of suitable electron-poor dienes for IEDDA reactions can include: tetrazines, such as 1,2,4,5 tetrazines, e.g. methyltetrazine and triazines (see, e.g., Devaraj, N K, et al., Fast and Sensitive Pretargeted Labeling of Cancer Cells via Tetrazine/Trans-Cyclooctene Cycloaddition *Agnew Chem Int Ed Engl.* 2009; 48(38): 7013-7016 and Karver, M R, et al., *Bioconjug Chem.* 2011 Nov. 16; 22(11):2263-2270). A non-limiting example of an electron-rich dienophile for IEDDA reactions can be trans-cyclooctene. One non-limiting example of a bio-orthogonal reaction and reaction pair can be the reaction of methyltetrazine (mTet) and trans-cyclooctene (TCO). That IEDDA pair was used because of the fast reaction kinetics and the reaction does not need a catalyst. Other suitable bio-orthogonal coupling reactions include alkyne-azide reactions, e.g. with a triazide and an alkyne, or alkyne-DBCO (dibenzocyclooctyne) reactions.

In certain embodiments, compound 1 and compound 2 disclosed herein can comprise a first moiety comprising a first member of a bio-orthogonal coupling pair, wherein the first member is configured to form a covalent bond with a second member of a bio-orthogonal coupling pair.

In certain embodiments, the first member of the bio-orthogonal coupling pair can be an electron-poor diene, an electron-rich dienophile, or a strained cycloalkene. In certain other embodiments, the first member of a bio-orthogonal coupling pair can be a tetrazine moiety selected from the group consisting of a 1,2,4,5-tetrazine moiety and a 4-(1,2,4,5-tetrazinyl)phenyl moiety.

In certain embodiments, the second member of the bio-orthogonal coupling pair can be an electron-poor diene, an electron-rich dienophile, or a strained cycloalkene. In certain other embodiments, the second member of a bio-orthogonal coupling pair can be a trans-cyclooctene (TCO).

The first member of a bio-orthogonal coupling pair can react with a second member of the bio-orthogonal coupling pair that is linked to a substrate (i.e. a second substrate), thereby forming self-antigen polypeptides bound to the second substrate. The second substrate can be a bead or a solid surface. The second substrate can be a magnetic bead. The second substrate can be a bead contained within a chromatography column or a spin column. The second substrate can be a porous matrix. The second substrate can be a TCO bead.

In certain embodiments, a linker links the first moiety and the second moiety. A linker is a moiety in a compound that connects one moiety to another. An "inert linker" is a moiety that covalently attaches, and optionally spaces, one moiety in a compound from another and which no substantial negative effect on the activity of the overall compound, e.g., in context of the present disclosure, the ability of the reactive groups, such as a tetrazine group, a succidimidyl group, or a dicarboxylic acid anhydride groups, such as maleic anhydride to react with their intended targets, and form and maintain a bond according to the methods described herein. Aside from serving to covalently-link two moieties, a linker may have a beneficial effect, such as in the physical separation of moieties to which it is attached, e.g., to optimize spacing to avoid steric effects. A linker also may serve some additional function, such as altering the hydrophobicity/hydrophilicity of the overall molecule, to provide an additional site, e.g., an amine protected by a protective group for linking additional moieties to the compound, or to rigidize the overall molecule. A linker is attached to the remainder of the compound by any suitable linkage moiety ("linkage"), e.g., by a carbon-carbon bond, an ester, a thioester, an amine, an ether, an amide, a carbonate, or a carbamate linkage to the additional moieties of the compound. The linker may be hydrocarbyl, that is including only carbons and hydrogens, or optionally comprising one or more hetero-atom, such as N, O, and/or S. In the context of the present disclosure, in one embodiment, one suitable linker is a divalent moiety comprising a PEG group-(O—CH2-CH2)n-, where n ranges from 2 to 100, e.g., from 2-15 ($PEG_{2-15}$), from 2-10 ($PEG_{2-10}$), or from 2-5 ($PEG_{2-5}$) such as 2, 3, 4 (PEG4), 5, 6, 7, 8, 9, 10, 11, 12, 13, 14, or 15. A PEG linker may comprise one or more methylene groups at either end in addition to a suitable linkage attaching the PEG group to the tetrazine and dicarboxylic anhydride moieties, e.g. maleic anhydride moieties.

Antibodies from serum or plasma of a blood sample can be coupled to a substrate (i.e., a first substrate) to form an antibody coupled substrate. The first substrate can be a bead or a solid surface. The first substrate can be a magnetic bead.

The first substrate can be a bead contained within a chromatography column or a spin column. The first substrate can be a protein A bead or protein G bead. Polypeptides in a cell or tissue lysate can bind to the antibody coupled substrate when the polypeptides have an affinity to the antibodies coupled to the antibody coupled substrate. Therefore, the antibody coupled substrate can be used to immunoprecipitate polypeptides from cell or tissue lysates. The antibody coupled substrate can be washed with a wash solution (e.g., 100 mM Hepes pH 8, 500 mM NaCl, 1% IGEPAL) to wash away all non-immunoglobulin proteins so that only antibodies couple to the first substrate.

In the methods disclosed herein, a first sample can be used to obtain antibodies to form an antibody coupled substrate. The first sample can be a biological sample. The first sample can be obtained from one biological source. The first sample can be obtained from more than one biological source, such as in the case of pooled samples. The first sample can be obtained from a healthy person or a patient with a specific disorder or disease (e.g. cancer, autoimmune disorder). The first sample can be a blood sample. The first sample can be serum or plasma. In certain embodiments, antibodies from serum or plasma of a first sample can be coupled to a substrate (i.e. a first substrate) to form an antibody coupled substrate.

In the methods disclosed herein, a second sample can be used to prepare a cell or tissue lysate. The second sample can be a biological sample. The second sample can be obtained from one biological source. The second sample can be obtained from more than one biological source, such as in the case of pooled samples. The second sample can be obtained from a healthy person or a patient. The second sample can be a blood sample. The second sample can be obtained from a cell, tissue, or organ culture; a biopsy; pelleted cells from any biological fluid sample (i.e., urine, blood, saliva, mucus, cerebrospinal fluid, semen, aspirate); or a tissue culture. The second sample can be a cell sample, tissue sample, a tumor sample, a biopsy sample, or a cell culture sample. The second sample can comprise a self-antigen polypeptide. The self-antigen polypeptide can be an autoantigen or a tumor associated antigen.

The first sample and second sample can be obtained by one of skill in the art using any means now known or later discovered including centrifugation, venipuncture, blood draw, excretion, swabbing, ejaculation, massage, biopsy, needle aspirate, lavage sample, scraping, surgical incision, laser capture microdissection, gradient separation, or other means known in the art. The first sample and second sample can be autologous samples. The first and second sample can be allogenic samples. In certain embodiments, the first sample and second sample can be the same blood sample; for example, the same blood sample can be used to prepare serum or plasma for the first sample and a cell lysate for the second sample. In certain other embodiments, the first sample and second sample can be different blood samples; for example, one blood sample can be used to prepare serum or plasma for the first sample and a separate blood sample can be used to prepare a cell lysate for the second sample. In certain other embodiments, the first sample can be blood, serum, or plasma and the second sample can be a cell sample, tissue sample, a tumor sample, a biopsy sample, or a cell culture sample.

The first sample and second sample can be isolated from a patient having cancer. The first sample and second sample can be isolated from a patient having a cancer selected from the group consisting of lung cancer, brain cancer, breast cancer, colorectal cancer, esophageal cancer, kidney cancer, liver cancer, ovarian cancer, pancreatic cancer, prostate cancer, gastric cancer, melanoma, merkel cell carcinoma, leukemia (AML, CLL), non-Hodgkin lymphoma (NHL), gallbladder cancer and cholangiocarcinoma (GBC, CCC), urinary bladder cancer (UBC), and uterine cancer (UEC). The first sample and second sample can be isolated from a patient having ovarian cancer.

The first sample and second sample can be isolated from a patient having an autoimmune disorder. The first sample and second sample can be isolated from a patient having an autoimmune disease selected from the group consisting of acquired immune deficiency syndrome (AIDS), acquired spenic atrophy, acute anterior uveitis, Acute Disseminated Encephalomyelitis (ADEM), acute gouty arthritis, acute necrotizing hemorrhagic leukoencephalitis, acute or chronic sinusitis, acute purulent meningitis (or other central nervous system inflammatory disorders), acute serious inflammation, Addison's disease, adrenalitis, adult onset diabetes mellitus (Type II diabetes), adult-onset idiopathic hypoparathyroidism (AOIH), Agammaglobulinemia, agranulocytosis, vasculitides, including vasculitis, optionally, large vessel vasculitis, optionally, polymyalgia rheumatica and giant cell (Takayasu's) arthritis, allergic conditions, allergic contact dermatitis, allergic dermatitis, allergic granulomatous angiitis, allergic hypersensitivity disorders, allergic neuritis, allergic reaction, alopecia arcata, alopecia totalis, Alport's syndrome, alvcolitis, optionally allergic alveolitis or fibrosing alveolitis, Alzheimer's disease, amyloidosis, amylotrophic lateral sclerosis (ALS; Lou Gehrig's disease), an cosinophil-related disorder, optionally cosinophilia, anaphylaxis, ankylosing spondylitis, antgicctasis, antibody-mediated nephritis, Anti-GBM/Anti-TBM nephritis, antigen-antibody complex-mediated diseases, antiglomerular basement membrane disease, anti-phospholipid antibody syndrome, antiphospholipid syndrome (APS), aphthac, aphthous stomatitis, aplastic anemia, arrhythmia, arteriosclerosis, arteriosclerotic disorders, arthritis, optionally rheumatoid arthritis such as acute arthritis, or chronic rheumatoid arthritis, arthritis chronica progrediente, arthritis deformans, ascariasis, aspergilloma, granulomas containing cosinophils, aspergillosis, aspermiogenese, asthma, optionally asthma bronchiale, bronchial asthma, or auto-immune asthma, ataxia telangiectasia, ataxic sclerosis, atherosclerosis, autism, autoimmune angioedema, autoimmune aplastic anemia, autoimmune atrophic gastritis, autoimmune diabetes, autoimmune disease of the testis and ovary including autoimmune orchitis and oophoritis, autoimmune disorders associated with collagen disease, autoimmune dysautonomia, autoimmune car disease, optionally autoimmune inner ear disease (AGED), autoimmune endocrine diseases including thyroiditis such as autoimmune thyroiditis, autoimmune enteropathy syndrome, autoimmune gonadal failure, autoimmune hearing loss, autoimmune hemolysis, Autoimmune hepatitis, autoimmune hepatological disorder, autoimmune hyperlipidemia, autoimmune immunodeficiency, autoimmune inner ear disease (AIED), autoimmune myocarditis, autoimmune neutropenia, autoimmune pancreatitis, autoimmune polyendocrinopathies, autoimmune polyglandular syndrome type I, autoimmune retinopathy, autoimmune thrombocytopenia purpura (ATP), autoimmune thyroid disease, autoimmune urticaria, autoimmune-mediated gastrointestinal diseases, Axonal & neuronal neuropathies, Balo disease, Behcet's disease, benign familial and ischemia-reperfusion injury, benign lymphocytic angiitis, Berger's disease (IgA nephropathy), bird-fancier's lung, blindness, Boeck's disease, bronchiolitis obliterans (non-transplant) vs NSIP, bronchitis, bronchopneumonic aspergillosis, Bruton's syndrome, bullous pemphigoid, Caplan's syndrome, Cardiomyopathy, cardiovascular ischemia, Castleman's syndrome, Celiac disease, celiac sprue (gluten enteropathy), cerebellar degeneration, cerebral ischemia, and disease accompanying vascularization, Chagas disease, channelopathies, optionally epilepsy, channelopathies of the CNS, chorioretinitis, choroiditis, an autoimmune hematological disorder, chronic active hepatitis or autoimmune chronic active hepatitis, chronic contact dermatitis, chronic cosinophilic pneumonia, chronic fatigue syndrome, chronic hepatitis, chronic hypersensitivity pneumonitis, chronic inflammatory arthritis, Chronic inflammatory demyelinating polyneuropathy (CIDP), chronic intractable inflammation, chronic mucocutaneous candidiasis, chronic neuropathy, optionally IgM polyneuropathies or IgM-mediated neuropathy, chronic obstructive airway disease, chronic pulmonary inflammatory disease, Chronic recurrent multifocal ostomyelitis (CRMO), chronic thyroiditis (Hashimoto's thyroiditis) or subacute thyroiditis, Churg-Strauss syndrome, cicatricial pemphigoid/benign mucosal pemphigoid, CNS inflammatory disorders, CNS vasculitis, Coeliac disease, Cogans syndrome, cold agglutinin disease, colitis polyposa, colitis such as ulcerative colitis, colitis ulcerosa, collagenous colitis, conditions involving infiltration of T cells and chronic inflammatory responses, congenital heart block, congenital rubella infection, Coombs positive anemia, coronary artery disease, Coxsackie myocarditis, CREST syndrome (calcinosis, Raynaud's phenomenon), Crohn's disease, cryoglobulinemia, Cushing's syndrome, cyclitis, optionally chronic cyclitis, heterochronic cyclitis, iridocyclitis, or Fuch's cyclitis, cystic fibrosis, cytokine-induced toxicity, deafness, degenerative arthritis, demyelinating diseases, optionally autoimmune demyelinating diseases, demyelinating neuropathies, dengue, dermatitis herpetiformis and atopic dermatitis, dermatitis including contact dermatitis, dermatomyositis, dermatoses with acute inflammatory components, Devic's disease (neuromyelitis optica), diabetic large-artery disorder, diabetic nephropathy, diabetic retinopathy, Diamond Blackfan anemia, diffuse interstitial pulmonary fibrosis, dilated cardiomyopathy, discoid lupus, diseases involving leukocyte diapedesis, Dressler's syndrome, Dupuytren's contracture, echovirus infection, eczema including allergic or atopic eczema, encephalitis such as Rasmussen's encephalitis and limbic and/or brainstem encephalitis, encephalomyelitis, optionally allergic encephalomyelitis or encephalomyelitis allergica and experimental allergic encephalomyelitis (EAE), endarterial hyperplasia, endocarditis, endocrine ophthamopathy, endometriosis, endomyocardial fibrosis, endophthalmia phacoanaphylactica, endophthalmitis, enteritis allergica, eosinophilia-myalgia syndrome, eosinophilic faciitis, epidemic keratoconjunctivitis, epidermolisis bullosa acquisita (EBA), episclera, episcleritis, Epstein-Barr virus infection, erythema elevatum et diutinum, erythema multiforme, erythema nodosum leprosum, erythema nodosum, erythroblastosis fetalis, esophageal dysmotility, Essential mixed cryoglobulinemia, ethmoid, Evan's syndrome, Experimental Allergic Encephalomyelitis (EAE), Factor VIII deficiency, farmer's lung, febris rheumatica, Felty's syndrome, fibromyalgia, fibrosing alveolitis, flariasis, focal segmental glomerulosclerosis (FSGS), food poisoning, frontal, gastric atrophy, giant cell arthritis (temporal arthritis), giant cell hepatitis, giant cell polymyalgia, glomerulonephritides, glomerulonephritis (GN) with and without nephrotic syndrome such as chronic or acute glomerulonephritis (e.g., primary GN), Goodpasture's syndrome, gouty arthritis, granulocyte transfusion-associated syndromes, granulomatosis including lymphomatoid granulomatosis, granulomatosis with polyangiitis (GPA), granulomatous uveitis, Grave's disease, Guillain-Barre syndrome, gutatte psoriasis, hemoglobinuria paroxysmatica, Hamman-Rich's disease, Hashimoto's disease, Hashimoto's encephalitis, Hashimoto's thyroiditis, hemochromatosis, hemolytic anemia or immune hemolytic anemia including autoimmune hemolytic anemia (AIHA), hemolytic anemia, hemophilia A, Henoch-Schonlein purpura, Herpes gestationis, human immunodeficiency virus (HIV) infection, hyperalgesia, hypogammaglobulinemia, hypogonadism, hypoparathyroidism, idiopathic diabetes insipidus, idiopathic facial paralysis, idiopathic hypothyroidism, idiopathic IgA nephropathy, idiopathic membranous GN or idiopathic membranous nephropathy, idiopathic nephritic syndrome, idiopathic pulmonary fibrosis, idiopathic sprue, Idiopathic thrombocytopenia purpura (ITP), IgA nephropathy, IgE-mediated diseases, optionally anaphylaxis and allergic or atopic rhinitis, IgG4-related sclerosing disease, ileitis regionalis, immune complex nephritis, immune responses associated with acute and delayed hypersensitivity mediated by cytokines and T-lymphocytes, immune-mediated GN, immunoregulatory lipoproteins, including adult or acute respiratory distress syndrome (ARDS), Inclusion body myositis, infectious arthritis, infertility due to antispermatozoan antibodies, inflammation of all or part of the uvea, inflammatory bowel disease (IBD) inflammatory hyperproliferative skin diseases, inflammatory myopathy, insulin-dependent diabetes (type1), insulitis, Interstitial cystitis, interstitial lung disease, interstitial lung fibrosis, iritis, ischemic re-perfusion disorder, joint inflammation, Juvenile arthritis, juvenile dermatomyositis, juvenile diabetes, juvenile onset (Type I) diabetes mellitus, including pediatric insulin-dependent diabetes mellitus (IDDM), juvenile-onset rheumatoid arthritis, Kawasaki syndrome, keratoconjunctivitis sicca, kypanosomiasis, Lambert-Eaton syndrome, leishmaniasis, leprosy, leucopenia, leukocyte adhesion deficiency, Leukocytoclastic vasculitis, leukopenia, lichen planus, lichen sclerosus, ligneous conjunctivitis, linear IgA dermatosis, Linear IgA disease (LAD), Loffler's syndrome, lupoid hepatitis, lupus (including nephritis, cerebritis, pediatric, non-renal, extra-renal, discoid, alopecia), Lupus (SLE), lupus erythematosus *Disseminatus*, Lyme arthritis, Lyme disease, lymphoid interstitial pneumonitis, malaria, male and female autoimmune infertility, maxillary, medium vessel vasculitis (including Kawasaki's disease and polyarteritis nodosa), membrano- or membranous proliferative GN (MPGN), including Type I and Type II, and rapidly progressive GN, membranous GN (membranous nephropathy), Meniere's disease, meningitis, microscopic colitis, microscopic polyangiitis, migraine, minimal change nephropathy, Mixed connective tissue disease (MCTD), mononucleosis infectiosa, Mooren's ulcer, Mucha-Habermann disease, multifocal motor neuropathy, multiple endocrine failure, multiple organ injury syndrome such as those secondary to septicemia, trauma or hemorrhage, multiple organ injury syndrome, multiple sclerosis (MS) such as spino-optical MS, multiple sclerosis, mumps, muscular disorders, myasthenia gravis such as thymoma-associated myasthenia gravis, myasthenia gravis, myocarditis, myositis, narcolepsy, necrotizing enterocolitis, and transmural colitis, and autoimmune inflammatory bowel disease, necrotizing, cutaneous, or hypersensitivity vasculitis, neonatal lupus syndrome (NLE), nephrosis, nephrotic syndrome, neurological disease, neuromyelitis optica (Devic's), neuromyelitis optica, neuromyotonia, neutropenia, non-cancerous lymphocytosis, nongranulomatous uveitis, non-malignant thymoma, ocular and orbital inflammatory disorders, ocular cicatricial pemphigoid, oophoritis, ophthalmia sym-
phatica, opsoclonus myoclonus syndrome (OMS), opsoclo-
nus or opsoclonus myoclonus syndrome (OMS), and sen-
sory neuropathy, optic neuritis, orchitis granulomatosa,
osteoarthritis, palindromic rheumatism, pancreatitis, pancy-
topenia, PANDAS (Pediatric Autoimmune Neuropsychiatric
Disorders Associated with *Streptococcus*), paraneoplastic
cerebellar degeneration, parancoplastic syndrome, paraneo-
plastic syndromes, including neurologic paraneoplastic syn-
dromes, optionally Lambert-Eaton myasthenic syndrome or
Eaton-Lambert syndrome, parasitic diseases such as Lesih-
mania, paroxysmal nocturnal hemoglobinuria (PNH), Parry
Romberg syndrome, pars planitis (peripheral uveitis), Par-
sonnage-Turner syndrome, parvovirus infection, pemphig-
oid such as pemphigoid bullous and skin pemphigoid, *Pem-*
*phigus* (including *Pemphigus vulgaris*), *Pemphigus*
*erythematosus, Pemphigus foliaceus, pemphigus* mucus-
membrane pemphigoid, *Pemphigus*, peptic ulcer, periodic
paralysis, peripheral neuropathy, perivenous encephalomy-
elitis, pernicious anemia (anemia perniciosa), pernicious
anemia, phacoantigenic uveitis, pneumonocirrhosis,
POEMS syndrome, polyarteritis nodosa, Type I, II, & III,
polyarthritis chronica primaria, polychondritis (e.g., refrac-
tory or relapsed polychondritis), polyendocrine autoimmune
disease, polyendocrine failure, polyglandular syndromes,
optionally autoimmune polyglandular syndromes (or polyg-
landular endocrinopathy syndromes), polymyalgia rheu-
matica, polymyositis, polymyositis/dermatomyositis, poly-
neuropathies, polyradiculitis acuta, post-cardiotomy
syndrome, posterior uveitis, or autoimmune uveitis,
postmyocardial infarction syndrome, postpericardiotomy
syndrome, post-streptococcal nephritis, post-vaccination
syndromes, presenile dementia, primary biliary cirrhosis,
primary hypothyroidism, primary idiopathic myxedema, pri-
mary lymphocytosis, which includes monoclonal B cell
lymphocytosis, optionally benign monoclonal gammopathy
and monoclonal gammopathy of undetermined significance,
MGUS, primary myxedema, primary progressive MS
(PPMS), and relapsing remitting MS (RRMS), primary
sclerosing cholangitis, progesterone dermatitis, progressive
systemic sclerosis, proliferative arthritis, psoriasis such as
plaque psoriasis, psoriasis, psoriatic arthritis, pulmonary
alveolar proteinosis, pulmonary infiltration cosinophilia,
pure red cell anemia or aplasia (PRCA), pure red cell
aplasia, purulent or nonpurulent sinusitis, pustular psoriasis
and psoriasis of the nails, pyelitis, pyoderma gangrenosum,
Quervain's thyreoiditis, Raynauds phenomenon, reactive
arthritis, recurrent abortion, reduction in blood pressure
response, reflex sympathetic dystrophy, refractory sprue,
Reiter's disease or syndrome, relapsing polychondritis,
reperfusion injury of myocardial or other tissues, reperfu-
sion injury, respiratory distress syndrome, restless legs syn-
drome, retinal autoimmunity, retroperitoneal fibrosis,
Reynaud's syndrome, rheumatic diseases, rheumatic fever,
rheumatism, rheumatoid arthritis, rheumatoid spondylitis,
rubella virus infection, Sampter's syndrome, sarcoidosis,
schistosomiasis, Schmidt syndrome, SCID and Epstein-Barr
virus-associated diseases, sclera, scleritis, sclerodactyl,
scleroderma, optionally systemic scleroderma, sclerosing
cholangitis, sclerosis disseminata, sclerosis such as systemic
sclerosis, sensoneural hearing loss, seronegative spondy-
loarthritides, Shechan's syndrome, Shulman's syndrome,
silicosis, Sjogren's syndrome, sperm & testicular autoim-
munity, sphenoid sinusitis, Stevens-Johnson syndrome, stiff-
man (or stiff-person) syndrome, subacute bacterial endo-
carditis (SBE), subacute cutaneous lupus crythematosus,
sudden hearing loss, Susac's syndrome, Sydenham's chorea, sympathetic ophthalmia, systemic lupus erythematosus
(SLE) or systemic lupus erythematodes, cutaneous SLE,
systemic necrotizing vasculitis, ANCA-associated vasculi-
tis, optionally Churg-Strauss vasculitis or syndrome (CSS),
tabes *dorsalis*, Takayasu's arteritis, telangiectasia, temporal
arteritis/Giant cell arteritis, thromboangitis ubiterans, throm-
bocytopenia, including thrombotic thrombocytopenia pur-
pura (TTP) and autoimmune or immune-mediated throm-
bocytopenia such as idiopathic thrombocytopenia purpura
(ITP) including chronic or acute ITP, thrombocytopenia
purpura (TTP), thyrotoxicosis, tissue injury, Tolosa-Hunt
syndrome, toxic epidermal necrolysis, toxic-shock syn-
drome, transfusion reaction, transient hypogammaglobu-
linemia of infancy, transverse myelitis, traverse myelitis,
tropical pulmonary cosinophilia, tuberculosis, ulcerative
colitis, undifferentiated connective tissue disease (UCTD),
urticaria, optionally chronic allergic urticaria and chronic
idiopathic urticaria, including chronic autoimmune urticaria,
uveitis, anterior uveitis, uveoretinitis, valvulitis, vascular
dysfunction, vasculitis, vertebral arthritis, vesiculobullous
dermatosis, vitiligo, Wegener's granulomatosis (Granulo-
matosis with Polyangiitis (GPA)), Wiskott-Aldrich syn-
drome, or x-linked hyper IgM syndrome.

In certain other embodiments, the first sample (e.g.,
blood, serum, plasma) can be isolated from a patient having
cancer and the second sample can be isolated from a cell
culture (e.g., high-grade serous ovarian carcinoma
(HGSOC) cell lines). In certain other embodiments, the first
sample (e.g., blood, serum, plasma) can be isolated from a
patient having an autoimmune disorder and the second
sample can be isolated from a cell culture (e.g., K562 cell
line).

In the disclosed methods, a cell or tissue lysate can be
prepared, e.g., by use of any suitable method, as are broadly-
known, e.g. by sonication or homogenization, optionally in
the presence of any suitable salts, buffers, surfactants, emul-
sifiers, chaotropic agents, chelating agents, e.g., in urea,
SDS or RIPA buffer. In certain embodiments, the mixed
sample or mixed cell or tissue lysate can be prepared in a
solution comprising at least one protease inhibitor (i.e.,
EDTA, Phenylmethylsulfonyl fluoride (PMSF), Leupeptin,
or pepstatin). In certain embodiments, the mixed sample or
mixed cell or tissue lysate can be prepared in a lysis buffer
comprising 100 mM Hepes pH 8, 500 mM NaCl, 1%
IGEPAL, 1 mM EDTA, 1 mM Phenylmethylsulfonyl fluo-
ride (PMSF), 10 μg/ml Leupeptin, 10 μg/ml pepstatin. In
certain embodiments, the mixed sample or cell or tissue
lysate can be prepared by mechanical homogenization (e.g.,
sonication or mortar and pestle or passage through narrow-
bore needles). In certain embodiments, the mixed sample or
cell or tissue lysate can be prepared in a mildly basic buffer
or salt solution, e.g., to produce a lysate having a pH ranging
from >7 to 10 (e.g., ranging from greater than 7 to 9 or 8 to
9.5). In certain other embodiments, the sample can be
cell-free, and may not require lysing, such as in the case of
analyzing a secretome, in the production of a recombinant
protein that is secreted into the medium, or in the analysis of
cell-free preparations (e.g. centrifuged supernatants) of bio-
logical fluids.

The method of isolating self-antigen polypeptides dis-
closed herein can comprise the step of coupling antibodies
from a first sample (e.g., blood, serum, or plasma) to a first
substrate thereby forming an antibody coupled substrate.
Without wishing to be bound by theory, antibody coupled
substrates can be prepared using serum of a patient with an
autoimmune disorder. The autoimmune patient's serum can
include antibodies to self-antigen polypeptides. Therefore, antibody coupled substrate having antibodies from an auto-immune patient's serum can be used to isolate and identify self-antigen polypeptides using the disclosed methods. Without wishing to be bound by theory, antibody coupled substrates can be prepared using scrum of a cancer patient. The cancer patient's serum can include antibodies to self-antigen polypeptides (e.g. tumor-associated antigens). Therefore, antibody coupled substrate having antibodies from a cancer patient's serum can be used to isolate and identify self-antigen polypeptides using the disclosed methods The method of isolating self-antigen polypeptides disclosed herein can comprise the step of mixing a sample (i.e., a second sample) or cell/tissue lysate (i.e., cell/tissue lysate of a second sample) with a compound disclosed herein (i.e., compound 1 or compound 2) thereby forming a mixed sample or mixed cell/tissue lysate. When using compound 1 (e.g., mTet-PEG''-CDM), the mixed sample or mixed cell/tissue lysate can comprise pH dependent tagged polypeptides. When using compound 2 (e.g., mTet-PEG$_n$-NHS), the mixed sample or mixed cell/tissue lysate can comprise permanently tagged polypeptides.

Figure 6:
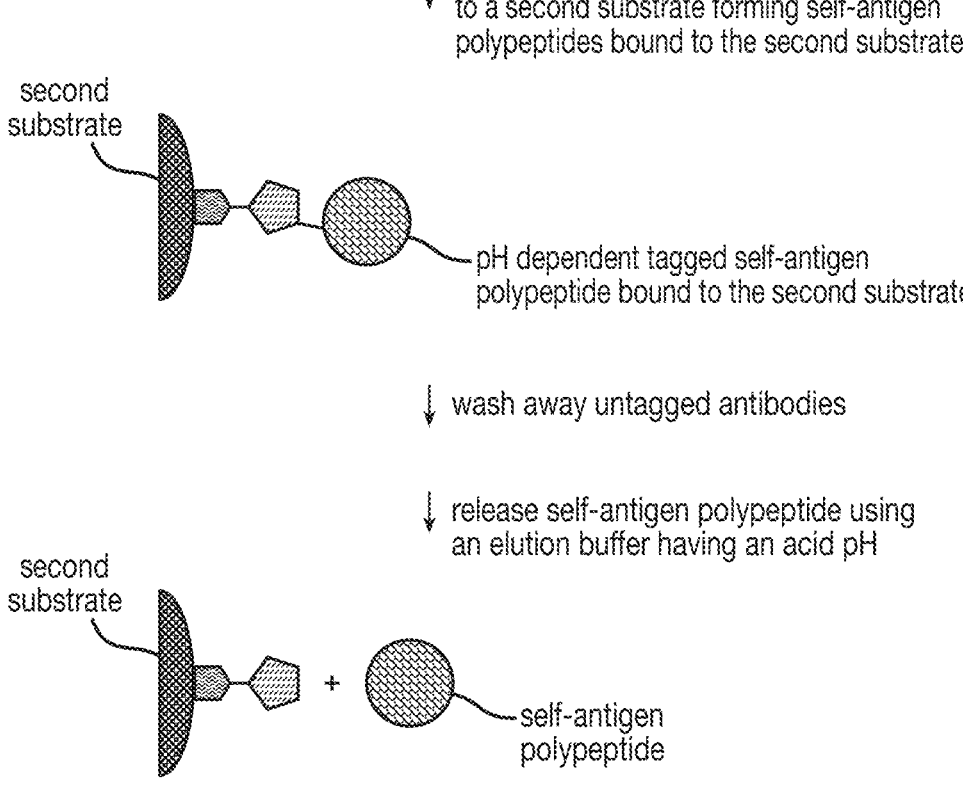
FIG. 6 shows a schematic of a non-limiting method of isolating self-antigen polypeptides when using compound 1 for tagging polypeptides in a sample.

The method of isolating self-antigen polypeptides disclosed herein can comprise the step of coupling tagged polypeptides (i.e., pH dependent tagged polypeptides) in a mixed sample or mixed cell/lysate to an antibody coupled substrate, thereby forming pH dependent tagged polypeptides bound to the antibody coupled substrate, as illustrated in FIG. 6. pH dependent tagged polypeptides in the mixed sample or mixed cell/tissue lysate can bind to the antibody coupled substrate when the pH dependent tagged polypeptides have an affinity to the antibodies coupled to the antibody coupled substrate.

The method of isolating self-antigen polypeptides disclosed herein can comprise the step of coupling tagged polypeptides (i.e., permanently tagged polypeptides) in a mixed sample or mixed cell/lysate to an antibody coupled substrate, thereby forming permanently tagged polypeptides bound to the antibody coupled substrate, as illustrated in FIG. 7. Permanently tagged polypeptides in the mixed sample or mixed cell/tissue lysate can bind to the antibody coupled substrate when the permanently tagged polypeptides have an affinity to the antibodies coupled to the antibody coupled substrate.

The method of isolating self-antigen polypeptides disclosed herein can comprise the step of eluting tagged polypeptides (i.e., pH dependent tagged polypeptides or permanently tagged polypeptides) that are bound to an antibody coupled substrate, thereby forming tagged self-antigen polypeptides in an eluted sample. The tagged polypeptides that are eluted from the antibody coupled substrate are referred to as "tagged self-antigen polypeptides". Therefore, the elution sample can comprise tagged self-antigen polypeptides. The elution sample can also comprise antibodies that were bound to the antibody coupled substrate. The tagged polypeptides and antibodies can be released from the antibody coupled substrate with the addition of a solution (e.g., 100 mM Hepes pH 8, 100 mM NaCl, 1% SDS) at room temperature with gentle rotation for two separate 10-minute incubations.

The method of isolating self-antigen polypeptides disclosed herein can comprise the step of coupling pH dependent tagged self-antigen polypeptides in an eluted sample to the second member of the bio-orthogonal coupling pair linked to a second substrate, thereby forming pH dependent tagged self-antigen polypeptides bound to a second substrate, as illustrated in FIG. 6.

The method of isolating self-antigen polypeptides disclosed herein can comprise the step of coupling permanently tagged self-antigen polypeptides in an eluted sample to the second member of the bio-orthogonal coupling pair linked to a second substrate, thereby forming permanently tagged self-antigen polypeptides bound to a second substrate, as illustrated in FIG. 7.

As illustrated in FIG. 6, the method of isolating self-antigen polypeptides disclosed herein can further comprise the step of washing the pH dependent tagged polypeptides that are bound to the antibody coupled substrate using any suitable wash solution that is not acidic (e.g., having a pH of 8 or greater). The pH of the wash solution for the pH dependent tagged polypeptides bound to the antibody coupled substrate can be selected to prevent premature hydrolysis of the amide bond between the pH dependent tagged polypeptide and the second moiety of compound 1. Suitable wash solutions include, without limitation: water, saline, PBS, Tris-EDTA, or other salt solutions or buffered salt solutions that do not hydrolyze the amide bond between the pH dependent tagged polypeptide and the second moiety of compound 1. For example, in certain embodiments, a wash solution (e.g., 100 mM Hepes pH 8, 500 mM NaCl, 1% IGEPAL) can be used to wash away substantially all unbound tagged polypeptides and contaminants without hydrolyzing the amide bond between the pH dependent tagged polypeptide and the second moiety of compound 1 so that only pH dependent tagged polypeptides were bound that have an affinity to antibodies coupled to the antibody coupled substrate.

As illustrated in FIG. 7, the method of isolating self-antigen polypeptides disclosed herein can further comprise the step of washing the permanently tagged polypeptides that are bound to the antibody coupled substrate using any suitable wash solution. The pH of the wash solution for the permanently tagged polypeptides bound to the antibody coupled substrate can vary since the tag is permanent and there can be no premature hydrolysis of the amide bond between the permanently tagged polypeptide and the second moiety of compound 2. Suitable wash solutions include, without limitation: water, saline, PBS, Tris-EDTA, or other salt solutions or buffered salt solutions. In certain embodiments, a wash solution (e.g., 100 mM Hepes pH 8, 500 mM NaCl, 1% IGEPAL) can be used to wash away all unbound tagged polypeptides and contaminants from the permanently tagged polypeptides that are bound to the antibody coupled substrate.

As illustrated in FIG. 6, the method of isolating self-antigen polypeptides disclosed herein can further comprise the step of washing the pH dependent tagged self-antigen polypeptides that are bound to a second substrate (i.e. a second substrate linked to a second member of a bio-orthogonal coupling pair; for example, the second substrate can be TCO beads) using any suitable wash solution that is not acidic (e.g., having a pH of 8 or higher). The pH of the wash solution for the pH dependent tagged self-antigen polypeptides bound to the second substrate can be selected to prevent premature hydrolysis of the amide bond attaching the pH dependent tagged self-antigen polypeptides to the second substrate. Suitable wash solutions include, without limitation: water, saline, PBS, Tris-EDTA, or other salt solutions or buffered salt solutions that do not hydrolyze the amide bond attaching the pH dependent tagged self-antigen polypeptides to the second substrate. For example, in certain embodiments, a polar aprotic solvent can be used to wash and remove any unbound materials (i.e. untagged antibodies and other contaminants) from the pH dependent tagged self-antigen polypeptides that are bound to the second substrate.

As illustrated in FIG. 7, the method of isolating self-antigen polypeptides disclosed herein can further comprise the step of washing the permanently tagged self-antigen polypeptides that are bound to a second substrate (i.e. a second substrate linked to a second member of a bio-orthogonal coupling pair; for example, the second substrate can be TCO beads) using any suitable wash solution. The pH of the wash solution for the permanently tagged self-antigen polypeptides bound to the second substrate can vary since the tag is permanent and there can be no premature hydrolysis of the amide bond attaching the permanently tagged self-antigen polypeptides to the second substrate. Suitable wash solutions include, without limitation: water, saline, PBS, Tris-EDTA, or other salt solutions or buffered salt solutions. In certain embodiments, a polar aprotic solvent can be used to wash and remove any unbound materials (i.e., untagged antibodies and other contaminants) from the permanently tagged self-antigen polypeptides that are bound to the second substrate.

The substrates (i.e., antibody coupled substrate or second substrate) can be washed one or more times in an art-recognized manner for any selected substrate. Two or more wash steps, with the same or different wash solutions can be applied.

As illustrated in FIG. 6, the method of isolating self-antigen polypeptides disclosed herein can comprise the step of eluting pH dependent tagged self-antigen polypeptides bound to a second substrate in an elution buffer having a pH more acidic than a pH of the mixed sample or mixed cell/tissue lysate by reversing the pH dependent covalent bond between the self-antigen polypeptides and the second moiety. By use of carboxylic anhydride coupling to amines of the polypeptides, once the amide bonds coupling the self-antigen polypeptides to the second substrate are cleaved, the primary amines of the polypeptides are restored. In certain embodiments, the elution buffer having a pH more acidic than a pH of the mixed sample or mixed cell/tissue lysate can comprise a weak organic acid selected from the group consisting of formic acid, acetic acid, and citric acid. In certain other embodiments, the composition of the elution buffer can have a pH ranging from 2 to <7, 3 to <7 or from 2.5 to 6.

The method of isolating self-antigen polypeptides disclosed herein can further comprise an optional step of mixing the self-antigen polypeptides eluted in the elution buffer (e.g. self-antigen polypeptides no longer bound to the second substrate) with a modified protease thereby forming a mixed sample comprising self-antigen peptides and the modified protease (this optional step is not illustrated in FIG. 6). The modified protease can be removed from the mixed sample by coupling the modified protease to a second member of a bio-orthogonal coupling pair, wherein the second member of the bio-orthogonal coupling pair is linked to the second substrate. The self-antigen peptides in the mixed sample can be eluted using any suitable elution buffer.

The modified protease can comprise a protease and a first member of a bio-orthogonal coupling pair attached to the protease. The first member can be configured to form a covalent bond with a second member of a bio-orthogonal coupling pair linked to the second substrate, thereby producing protease bound to the second substrate.

In certain embodiments, the modified protease can be a modified hydrolase and the protease can be a hydrolase. In certain other embodiments, the modified protease can be a modified serine hydrolase and the protease can be a serine hydrolase. In certain other embodiments, the modified protease can be a modified trypsin and the protease can be a trypsin.

Trypsin comprises a number of primary amines, e.g., Lys residues, and its N-terminus. The primary amine of lysine can be used to attach groups using any useful chemistry. Trypsin has 14 lysine residues, and only two arginine residues, the other target for autolysis. The modified trypsin is referred to herein as MT-trypsin. The presence of methyltetrazine on the MT-trypsin allows for the near complete removal of this protein from solution by coupling to beads containing TCO. Together, methyltetrazine and TCO form a bio-orthogonal coupling pair where these two moieties react to form a covalent linkage at very rapid rates. Other tetrazinyl moieties can be employed in this click chemistry pair, or other bio-orthogonal click chemistry pairs can be employed in the linking of trypsin to a substrate, such as a bead, for removal.

As illustrated in FIG. 7, the method of isolating self-antigen polypeptides disclosed can comprise the step of adding a modified protease disclosed herein to permanently tagged self-antigen polypeptides bound to the second substrate, thereby forming self-antigen peptides. The modified protease can be coupled to a second member of a bio-orthogonal coupling pair, wherein the second member of the bio-orthogonal coupling pair is linked to the second substrate. The self-antigen peptides can be eluted using any suitable elution buffer.

There are multiple challenges of current conventional approaches of isolating and identifying self-antigen polypeptides:

(1) For common autoimmune diseases, large pools of patient sera are required for conventional immunoprecipitation and biochemical analysis of autoantigens. While this approach has been useful for diseases such as rheumatoid arthritis, lupus, and multiple sclerosis, it is not been feasible for less common autoimmune diseases. More importantly, this methodology cannot be applied to highly heterogeneous diseases such as cancer, where a more personalized approach is necessary.

(2) Protein arrays, peptide arrays, and commercial antigen chips have been used; however, such arrays have two significant shortcomings: 1. they are limited in the number of array elements. Thus, proteome-wide screens are challenging with arrays. 2. arrays are often unable to adequately address the role of post-translational modifications in specific target recognition (something that is the well established in rheumatoid arthritis, for example). Thus, protein arrays, peptide arrays, and antigen chips are costly, biased, and highly specific for previously known antigens and therefore cannot be used to identify unknown self-antigens.

(3) A more personalized conventional approach uses patient-specific immunoprecipitation to characterize a patient's autoantigen profile. This conventional method relies on using radiolabeled proteins from culture cell lysates. Radiolabeled proteins are required to distinguish low abundance autoantigens from a very high concentration of immunoglobulins found in patient serum. In this method, a gel electrophoresis pattern of patient autoantigens is compared to a previously categorized autoimmune disease. Because the proteins are radiolabeled, this method can be undesirable and there is limited physical separation of contaminating immunoglobulins. Therefore, the autoantigens cannot be identified by mass spectrometry and the conventional approach can only approximate, but not identify, the actual autoantigens.

The method of isolating self-antigen polypeptides disclosed herein addresses each of the above-referenced challenges and is very effective at isolating and identifying patient specific autoantigens (i.e. self-antigen polypeptides). For example, the methods of isolating self-antigen polypeptides disclosed herein are proteome-wide, unbiased, amenable to identifying post-translationally modified autoantigens, personalized, safe, and eliminates immunoglobulin contamination from the purified autoantigens.

In another aspect of the present disclosure, a self-antigen isolation kit is provided for isolating self-antigen polypeptides. Disclosed herein is a self-antigen isolation kit configured to perform any one of the methods of isolating self-antigen polypeptides disclosed herein. A self-antigen isolation kit can comprise packaging and at least stated components of the kit. Packaging can be any suitable container, such as a box, sleeve, tube, carton, pouch, bag, etc., suitable for storage and/or delivery of the kit components. A "kit" may comprise one or more individual containers for the elements of the kit, though in one embodiment, all components of a kit are packaged together, or are packaged in a single container. For reagents or compositions, e.g. compounds, substrates, elution buffers, etc. described herein, the kit comprises one or more vessels containing stated reagent(s) or composition(s).

A self-antigen isolation kit disclosed herein can comprise compound 1, a first substrate (i.e., protein A or protein G beads) configured to couple antibodies from serum or plasma of a first sample, and a second substrate linked to a second member of a bio-orthogonal coupling pair (i.e., TCO beads). The first substrate can be used to isolate polypeptides having an affinity to antibodies coupled to the first substrate. The first substrate can be in any suitable form, such as in the form of a bead, a solid surface, a magnetic bead, a bead contained within a chromatography column or a spin column, a Protein A bead, or Protein G bead. The second substrate can be used to isolate self-antigen polypeptides bonded to compound 1 (pH dependent tagged self-antigen polypeptides). Additional vessels can comprise, for example, one or more of: a coupling solution disclosed herein, one or more wash solutions disclosed herein, and elution buffers disclosed herein, optionally in concentrated form, e.g., as a 2×, 5×, 10× or 25× concentrate. The coupling solution can have a pH greater than 7, such as greater than 7 to 10, greater than 7 to 9, 8 to 9.5, or greater than 8 to 9.5. The elution buffer for eluting pH dependent tagged polypeptides from an antibody coupled substrate can have a pH greater than 7, such as greater than 7 to 10, greater than 7 to 9, 8 to 9.5, or greater than 8 to 9.5. The elution buffer for eluting pH dependent tagged self-antigen polypeptides from a second substrate can have a pH less than 7, such as 2 to <7, 3 to <7, or 2.5 to 6. Additional optional vessels can comprise a modified protease described herein and elution buffer for eluting peptides. The elution buffer for eluting peptides can have any pH between 7 and 9 (e.g., ammonium bicarbonate buffers). The pH is selected between 7 and 9 to be compatible with mass spectrometry.

A self-antigen isolation kit disclosed herein can comprise compound 2, a first substrate (i.e., protein A or protein G beads) configured to couple antibodies from serum or plasma of a first sample, a second substrate linked to a second member of a bio-orthogonal coupling pair (i.e., TCO beads), and a modified protease disclosed herein. The first substrate can be used to isolate polypeptides having an affinity to antibodies coupled to the first substrate. The first substrate can be in any suitable form, such as in the form of a bead, a solid surface, a magnetic bead, a bead contained within a chromatography column or a spin column, a protein A bead, or protein G bead. The second substrate can be used to isolate self-antigen polypeptides bonded to compound 2 (permanently tagged self-antigen polypeptides). The modified protease can be used to digest the self-antigen polypeptides to self-antigen peptides. Additional vessels can comprise, for example, one or more of: a coupling solution disclosed herein, one or more wash solutions disclosed herein, and elution buffers disclosed herein, optionally in concentrated form, e.g., as a 2×, 5×, 10× or 25× concentrate. The pH of the coupling solutions and elution buffers do not have to be less than 7 for the permanently tagged polypeptides bound to the antibody coupled substrate or the permanently tagged self-antigen polypeptides bound to the second substrate since the tag is permanent and there can be no premature hydrolysis of the amide bond attaching the permanent tag between the polypeptide and second moiety of compound 2 or the permanently tagged self-antigen polypeptides to the second substrate. Instead, these solutions and buffers can have any pH between 3 and 9. The elution buffer for eluting peptides can have any pH between 7 and 9 (e.g., ammonium bicarbonate buffers). The pH can be selected between 7 and 9 to be compatible with mass spectrometry.

The vessels of the kit can be a compartment in a cartridge for use in an automated or semi-automated device or system for isolating self-antigen polypeptides.

Figure 8:
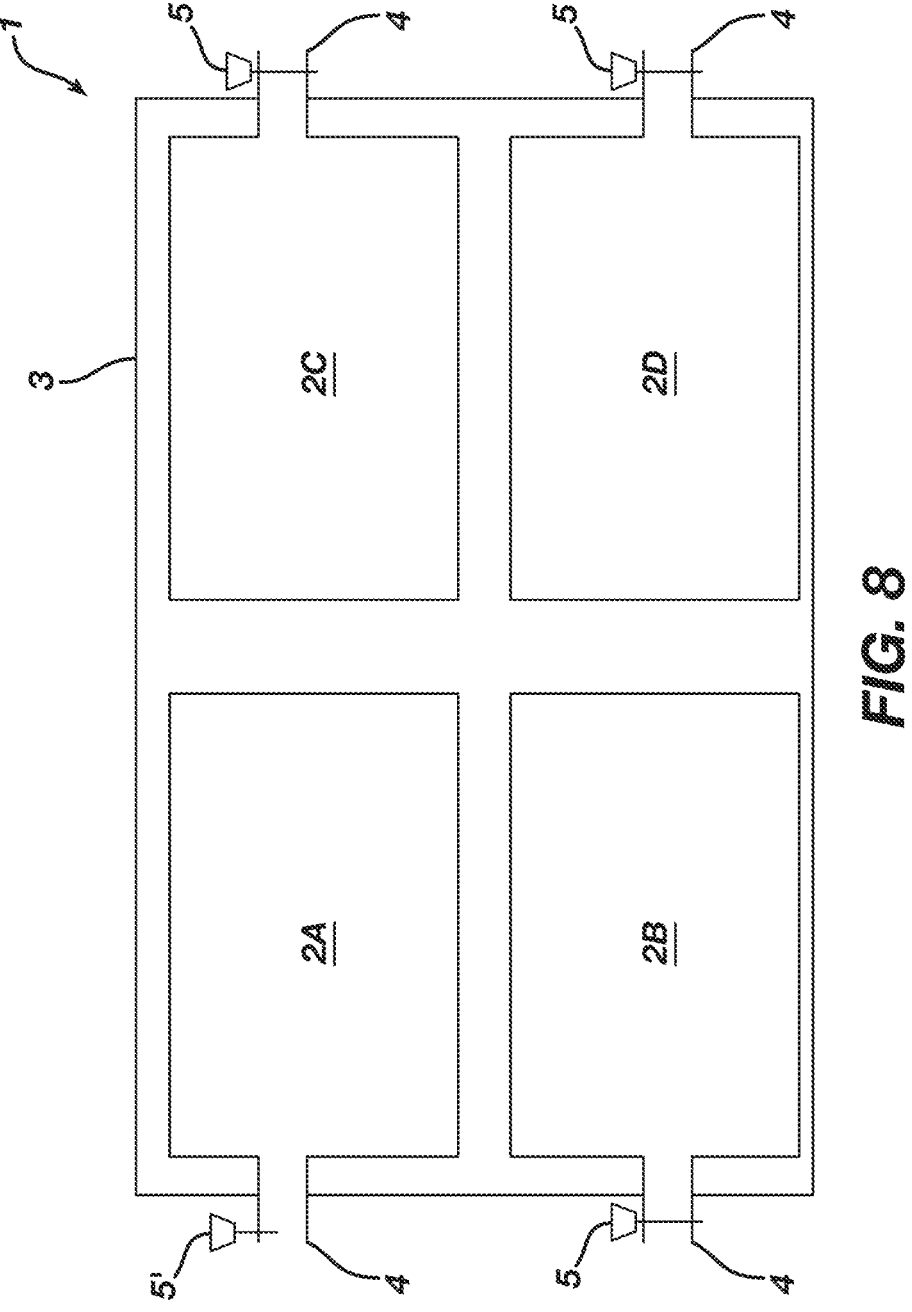
FIG. 8 shows a schematic depiction of an exemplary cartridge.

FIG. 8 depicts schematically a cartridge 1 comprising a housing 3, four compartments 2A, 2B, 2C, 2D, outlets 4, closed valves 5 and open valve 5'. The housing 5 can have any useful configuration and is adapted to insert into an automated device or system for controlling delivery of compositions contained within compartments 2A, 2B, 2C, 2D. Each compartment can contain a different reagent or composition, or the same reagent or composition. Valves 5 and 5' may be controlled by any suitable mechanical or electromechanical mechanism, such as by solenoids and may be placed at any point in or external to the cartridge 1, for example, the outlets may fluidly couple with the valves, which are part of the device into which the cartridge 1 inserts. The cartridge 1 depicted in FIG. 8 is merely exemplary and may comprise any number of compartments, any shape, any fluid path, and any fluid control mechanism. A person of ordinary skill in the engineering arts can configure a suitable cartridge for use in any device or system, such as an automated system. Control of the cartridge and/or reagents or compositions removed from the cartridge, may be automated, e.g., controlled by a computer-implemented process.

The following numbered clauses are directed to various non-limiting embodiments of inventions according to the present disclosure:

Clause 1. A method of isolating self-antigen polypeptides, the method comprising:
   a) coupling antibodies from a first sample to a first substrate, thereby forming an antibody coupled substrate;
   b) mixing a second sample with a compound, thereby forming a mixed sample comprising tagged polypeptides, wherein the compound comprises
      a first moiety comprising a first member of a bio-orthogonal coupling pair, wherein the first member is configured to form a covalent bond with a second member of a bio-orthogonal coupling pair;

a second moiety configured to form a pH dependent covalent bond with a polypeptide; and a linker linking the first moiety and the second moiety;

c) coupling the tagged polypeptides in the mixed sample to the antibody coupled substrate, thereby forming tagged polypeptides bound to the antibody coupled substrate;

d) eluting the tagged polypeptides bound to the antibody coupled substrate, thereby forming tagged self-antigen polypeptides in an eluted sample;

e) coupling the tagged self-antigen polypeptides in the eluted sample to a second member of a bio-orthogonal coupling pair, wherein the second member of the bio-orthogonal coupling pair is linked to a second substrate, thereby forming self-antigen polypeptides bound to the second substrate; and f) eluting the self-antigen polypeptides bound to a second substrate in an elution buffer having a pH more acidic than a pH of the mixed sample by reversing the pH dependent covalent bond between the self-antigen polypeptides and the second moiety.

Clause 2. A method of isolating self-antigen polypeptides, the method comprising:

a) mixing a second sample with a compound, thereby forming a mixed sample comprising tagged polypeptides, wherein the compound comprises a first moiety comprising a first member of a bio-orthogonal coupling pair, wherein the first member is configured to form a covalent bond with a second member of a bio-orthogonal coupling pair;

a second moiety configured to form a pH dependent covalent bond with a polypeptide; and a linker linking the first moiety and the second moiety;

b) coupling the tagged polypeptides in the mixed sample to an antibody coupled substrate, thereby forming tagged polypeptides bound to the antibody coupled substrate, wherein the antibody coupled substrate comprises antibodies from a first sample coupled to a first substrate;

c) eluting the tagged polypeptides bound to the antibody coupled substrate, thereby forming tagged self-antigen polypeptides in an eluted sample;

d) coupling the tagged self-antigen polypeptides in the eluted sample to the second member of a bio-orthogonal coupling pair, wherein the second member of the bio-orthogonal coupling pair is linked to a second substrate, thereby forming self-antigen polypeptides bound to the second substrate; and e) eluting the self-antigen polypeptides bound to the second substrate in an elution buffer having a pH more acidic than a pH of the mixed sample by reversing the pH dependent covalent bond between the self-antigen polypeptides and the second moiety.

Clause 3. A method of isolating self-antigen polypeptides, the method comprising:

a) coupling tagged polypeptides in a mixed sample to an antibody coupled substrate, thereby forming tagged polypeptides bound to the antibody coupled substrate, wherein the antibody coupled substrate comprises antibodies from a first sample coupled to a first substrate, and wherein the mixed sample comprising tagged polypeptides is a mixture of a compound and a second sample, the compound comprising a first moiety comprising a first member of a bio-orthogonal coupling pair, wherein the first member is configured to form a covalent bond with a second member of a bio-orthogonal coupling pair;

a second moiety configured to form a pH dependent covalent bond with a polypeptide; and a linker linking the first moiety and the second moiety;

b) eluting the tagged polypeptides bound to the antibody coupled substrate, thereby forming tagged self-antigen polypeptides in an eluted sample;

c) coupling the tagged self-antigen polypeptides in the eluted sample to the second member of a bio-orthogonal coupling pair, wherein the second member of the bio-orthogonal coupling pair is linked to a second substrate, thereby forming self-antigen polypeptides bound to the second substrate; and d) eluting the self-antigen polypeptides bound to the second substrate in an elution buffer having a pH more acidic than a pH of the mixed sample by reversing the pH dependent covalent bond between the self-antigen polypeptides and the second moiety.

Clause 4. A method of isolating self-antigen polypeptides, the method comprising:

a) coupling antibodies from serum or plasma of a first sample to a first substrate, thereby forming an antibody coupled substrate;

b) mixing cell or tissue lysate of a second sample with a compound, thereby forming a mixed cell or tissue lysate comprising tagged polypeptides, wherein the compound comprises a first moiety comprising a first member of a bio-orthogonal coupling pair, wherein the first member is configured to form a covalent bond with a second member of a bio-orthogonal coupling pair;

a second moiety configured to form a pH dependent covalent bond with a polypeptide; and a linker linking the first moiety and the second moiety;

c) coupling the tagged polypeptides in the mixed cell or tissue lysate to the antibody coupled substrate, thereby forming tagged polypeptides bound to the antibody coupled substrate;

d) eluting the tagged polypeptides bound to the antibody coupled substrate, thereby forming tagged self-antigen polypeptides in an eluted sample;

e) coupling the tagged self-antigen polypeptides in the eluted sample to the second member of a bio-orthogonal coupling pair, wherein the second member of the bio-orthogonal coupling pair is linked to a second substrate, thereby forming self-antigen polypeptides bound to the second substrate; and f) eluting the self-antigen polypeptides bound to the second substrate in an elution buffer having a pH more acidic than a pH of the mixed cell or tissue lysate by reversing the pH dependent covalent bond between the self-antigen polypeptides and the second moiety.

Clause 5. A method of isolating self-antigen polypeptides, the method comprising:

a) mixing cell or tissue lysate of a second sample with a compound, thereby forming a mixed cell or tissue lysate comprising tagged polypeptides, wherein the compound comprises a first moiety comprising a first member of a bio-orthogonal coupling pair, wherein the first member is configured to form a covalent bond with a second member of a bio-orthogonal coupling pair;
a second moiety configured to form a pH dependent covalent bond with a polypeptide; and
a linker linking the first moiety and the second moiety;

b) coupling the tagged polypeptides in the mixed cell or tissue lysate to an antibody coupled substrate, thereby forming tagged polypeptides bound to the antibody coupled substrate, wherein the antibody coupled substrate comprises antibodies from serum or plasma of a first sample coupled to a first substrate;

c) eluting the tagged polypeptides bound to the antibody coupled substrate, thereby forming tagged self-antigen polypeptides in an eluted sample;

d) coupling the tagged self-antigen polypeptides in the eluted sample to the second member of a bio-orthogonal coupling pair, wherein the second member of the bio-orthogonal coupling pair is linked to a second substrate, thereby forming self-antigen polypeptides bound to the second substrate; and e) eluting the self-antigen polypeptides bound to the second substrate in an elution buffer having a pH more acidic than a pH of the mixed cell or tissue lysate by reversing the pH dependent covalent bond between the self-antigen polypeptides and the second moiety.

Clause 6. A method of isolating self-antigen polypeptides, the method comprising:

a) coupling tagged polypeptides in a mixed cell or tissue lysate to an antibody coupled substrate, thereby forming tagged polypeptides bound to an antibody coupled substrate,
wherein the antibody coupled substrate comprises antibodies from serum or plasma of a first sample coupled to a first substrate, and
wherein the mixed cell or tissue lysate comprising tagged polypeptides is a mixture of a compound and a cell or tissue lysate from a second sample, the compound comprising
a first moiety comprising a first member of a bio-orthogonal coupling pair, wherein the first member is configured to form a covalent bond with a second member of a bio-orthogonal coupling pair;
a second moiety configured to form a pH dependent covalent bond with a polypeptide; and
a linker linking the first moiety and the second moiety;

b) eluting the tagged polypeptides bound to the antibody coupled substrate, thereby forming tagged self-antigen polypeptides in an eluted sample;

c) coupling the tagged self-antigen polypeptides in the eluted sample to the second member of a bio-orthogonal coupling pair, wherein the second member of the bio-orthogonal coupling pair is linked to a second substrate, thereby forming self-antigen polypeptides bound to the second substrate; and d) eluting the self-antigen polypeptides bound to the second substrate in an elution buffer having a pH more acidic than a pH of the mixed cell or tissue lysate by reversing the pH dependent covalent bond between the self-antigen polypeptides and the second moiety.

Clause 7. The method of any one of clauses 1-6, further comprising:
mixing the self-antigen polypeptides eluted in the elution buffer with a modified protease, thereby forming a mixed sample comprising self-antigen peptides and the modified protease, wherein the modified protease comprises
a protease; and
a first member of a bio-orthogonal coupling pair attached to the protease, wherein the first member is configured to form a covalent bond with a second member of a bio-orthogonal coupling pair;
coupling the modified protease in the mixed sample to a second member of a bio-orthogonal coupling pair, wherein the second member of the bio-orthogonal coupling pair is linked to the second substrate; and
eluting the self-antigen peptides.

Clause 8. The method of clause 7, wherein the modified protease is a modified hydrolase and the protease is a hydrolase.

Clause 9. The method of any one of clauses 7 or 8, wherein the modified protease is a modified serine hydrolase and the protease is a serine hydrolase.

Clause 10. The method of any one of clauses 7-9, wherein the modified protease is a modified trypsin and the protease is a trypsin.

Clause 11. The method of any one of clauses 1-10, wherein the first sample and second sample are autologous samples.

Clause 12. The method of any one of clauses 1-10, wherein the first sample and second sample are allogenic samples.

Clause 13. The method of any one of clauses 1-12, wherein the first sample and second sample are the same blood sample.

Clause 14. The method of any one of clauses 1-12, wherein the first sample and second sample are different blood samples.

Clause 15. The method of any one of clauses 1-12, wherein the first sample is blood, serum or plasma and wherein the second sample is selected from a group consisting of blood, a cell sample, a tissue sample, a tumor sample, a biopsy sample, and a cell culture sample.

Clause 16. The method of any one of clauses 1-15, wherein the first sample and second sample are isolated from a patient having a cancer selected from the group consisting of lung cancer, brain cancer, breast cancer, colorectal cancer, esophageal cancer, kidney cancer, liver cancer, ovarian cancer, pancreatic cancer, prostate cancer, gastric cancer, melanoma, merkel cell carcinoma, leukemia (AML, CLL), non-Hodgkin lymphoma (NHL), gallbladder cancer and cholangiocarcinoma (GBC, CCC), urinary bladder cancer (UBC), and uterine cancer (UEC).

Clause 17. The method of any one of clauses 1-16, wherein the first sample and second sample are isolated from a patient having ovarian cancer.

Clause 18. The method of any one of clauses 1-15, wherein the first sample and second sample are isolated from a patient having an autoimmune disorder.

Clause 19. The method of any one of clauses 1-18, wherein the self-antigen polypeptides are autoantigens or tumor-associated antigens.

Clause 20. The method of any one of clauses 1-19, wherein the second moiety is a dicarboxylic acid anhydride moiety.

Clause 21. The method of clause 20, wherein the dicarboxylic acid anhydride moiety is a maleic anhydride moiety.

Clause 22. The method of clause 20, wherein the dicarboxylic acid anhydride moiety is a 2-(2'-carboxyethyl) maleic anhydride moiety.

Clause 23. The method of any one of clauses 1-22, wherein the first member of a bio-orthogonal coupling pair is an electron-poor diene, an electron-rich dienophile, or a strained cycloalkene.

Clause 24. The method of any one of clauses 1-23, wherein the first member of a bio-orthogonal coupling pair is a tetrazine moiety selected from the group consisting of a 1,2,4,5-tetrazine moiety or a 4-(1,2,4,5-tetrazinyl)phenyl moiety.

Clause 25. The method of any one of clauses 1-24, wherein the linker is an inert linker.

Clause 26. The method of any one of clauses 1-25, wherein the first substrate is a bead or a solid surface.

Clause 27. The method of any one of clauses 1-26, wherein the first substrate is a magnetic bead.

Clause 28. The method of any one of clauses 1-27, wherein the first substrate is a bead contained within a chromatography column or a spin column.

Clause 29. The method of any one of clauses 1-28, wherein the first substrate is a protein A bead or protein G bead.

Clause 30. The method of any one of clauses 1-29, wherein the second substrate is a bead or a solid surface.

Clause 31. The method of any one of clauses 1-30, wherein the second substrate is a magnetic bead.

Clause 32. The method of any one of clauses 1-31, wherein the second substrate is a bead contained within a chromatography column or a spin column.

Clause 33. The method of any one of clauses 1-29, wherein the second substrate is a porous matrix.

Clause 34. The method of any one of clauses 1-33, wherein the mixed sample or the mixed cell or tissue lysate has a pH greater than 7.

Clause 35. The method of clause 34, wherein the pH greater than 7 ranges from greater than 7 to 10, greater than 7 to 9, or 8 to 9.5.

Clause 36. The method of any one of clauses 1-35, wherein the elution buffer having a pH more acidic than a pH of the mixed sample or the mixed cell or tissue lysate comprises a weak organic acid selected from the group consisting of formic acid, acetic acid, and citric acid.

Clause 37. The method of any one of clauses 1-36, wherein the pH more acidic than a pH of the mixed sample or the mixed cell or tissue lysate ranges from 2 to less than 7, 3 to less than 7, or from 2.5 to 6.

Clause 38. The method of any one of clauses 1-37, further comprising washing the tagged polypeptides bound to the antibody coupled substrate to remove any unbound materials from the tagged polypeptides bound to the antibody coupled substrate.

Clause 39. The method of any one of clauses 1-38, further comprising washing the self-antigen polypeptides bound to the second substrate using a polar aprotic solvent to remove any unbound materials from the self-antigen polypeptides bound to the second substrate.

Clause 40. A method of isolating self-antigen polypeptides, the method comprising:

a) coupling antibodies from a first sample to a first substrate, thereby forming an antibody coupled substrate;

b) mixing a second sample with a compound, thereby forming a mixed sample comprising tagged polypeptides, wherein the compound comprises a first moiety comprising a first member of a bio-orthogonal coupling pair, wherein the first member is configured to form a covalent bond with a second member of a bio-orthogonal coupling pair;

a second moiety configured to form a covalent bond with a polypeptide; and a linker linking the first moiety and the second moiety;

c) coupling the tagged polypeptides in the mixed sample to the antibody coupled substrate, thereby forming tagged polypeptides bound to the antibody coupled substrate;

d) eluting the tagged polypeptides bound to the antibody coupled substrate, thereby forming tagged self-antigen polypeptides in an eluted sample;

e) coupling the tagged self-antigen polypeptides in the eluted sample to a second member of a bio-orthogonal coupling pair, wherein the second member of the bio-orthogonal coupling pair is linked to a second substrate, thereby forming self-antigen polypeptides bound to the second substrate;

f) adding a modified protease to the self-antigen polypeptides bound to the second substrate, thereby forming self-antigen peptides, wherein the modified protease comprises a protease; and a first member of a bio-orthogonal coupling pair attached to the protease, wherein the first member is configured to form a covalent bond with a second member of a bio-orthogonal coupling pair;

g) coupling the modified protease to the second member of a bio-orthogonal coupling pair, wherein the second member of the bio-orthogonal coupling pair is linked to the second substrate; and h) eluting the self-antigen peptides.

Clause 41. A method of isolating self-antigen polypeptides, the method comprising:

a) mixing a second sample with a compound, thereby forming a mixed sample comprising tagged polypeptides, wherein the compound comprises a first moiety comprising a first member of a bio-orthogonal coupling pair, wherein the first member is configured to form a covalent bond with a second member of a bio-orthogonal coupling pair;

a second moiety configured to form a covalent bond with a polypeptide; and a linker linking the first moiety and the second moiety;

b) coupling the tagged polypeptides in the mixed sample to an antibody coupled substrate, thereby forming tagged polypeptides bound to the antibody coupled substrate, wherein the antibody coupled substrate comprises antibodies from a first sample coupled to a first substrate;

c) eluting the tagged polypeptides bound to the antibody coupled substrate, thereby forming tagged self-antigen polypeptides in an eluted sample;

d) coupling the tagged self-antigen polypeptides in the eluted sample to the second member of a bio-orthogonal coupling pair, wherein the second member of the bio-orthogonal coupling pair is linked to a second substrate, thereby forming self-antigen polypeptides bound to the second substrate;

e) adding a modified protease to the self-antigen polypeptides bound to the second substrate, thereby forming self-antigen peptides, wherein the modified protease comprises a protease; and a first member of a bio-orthogonal coupling pair attached to the protease, wherein the first member is configured to form a covalent bond with a second member of a bio-orthogonal coupling pair;

f) coupling the modified protease to the second member of a bio-orthogonal coupling pair, wherein the second member of the bio-orthogonal coupling pair is linked to the second substrate; and g) eluting the self-antigen peptides.

Clause 42. A method of isolating self-antigen polypeptides, the method comprising:

a) coupling tagged polypeptides in a mixed sample to an antibody coupled substrate, thereby forming tagged polypeptides bound to the antibody coupled substrate, wherein the antibody coupled substrate comprises antibodies from a first sample coupled to a first substrate, and wherein the mixed sample comprising tagged polypeptides is a mixture of a compound and a second sample, the compound comprising a first moiety comprising a first member of a bio-orthogonal coupling pair, wherein the first member is configured to form a covalent bond with a second member of a bio-orthogonal coupling pair;

a second moiety configured to form a covalent bond with a polypeptide; and a linker linking the first moiety and the second moiety;

b) eluting the tagged polypeptides bound to the antibody coupled substrate, thereby forming tagged self-antigen polypeptides in an eluted sample;

c) coupling the tagged self-antigen polypeptides in the eluted sample to the second member of a bio-orthogonal coupling pair, wherein the second member of the bio-orthogonal coupling pair is linked to a second substrate, thereby forming self-antigen polypeptides bound to the second substrate;

d) adding a modified protease to the self-antigen polypeptides bound to the second substrate, thereby forming self-antigen peptides, wherein the modified protease comprises a protease; and a first member of a bio-orthogonal coupling pair attached to the protease, wherein the first member is configured to form a covalent bond with a second member of a bio-orthogonal coupling pair;

e) coupling the modified protease to the second member of a bio-orthogonal coupling pair, wherein the second member of the bio-orthogonal coupling pair is linked to the second substrate; and f) eluting the self-antigen peptides.

Clause 43. A method of isolating self-antigen polypeptides, the method comprising:

a) coupling antibodies from serum or plasma of a first sample to a first substrate, thereby forming an antibody coupled substrate;

b) mixing cell or tissue lysate of a second sample with a compound, thereby forming a mixed cell or tissue lysate comprising tagged polypeptides, wherein the compound comprises a first moiety comprising a first member of a bio-orthogonal coupling pair, wherein the first member is configured to form a covalent bond with a second member of a bio-orthogonal coupling pair;

a second moiety configured to form a covalent bond with a polypeptide; and a linker linking the first moiety and the second moiety;

c) coupling the tagged polypeptides in the mixed cell or tissue lysate to the antibody coupled substrate, thereby forming tagged polypeptides bound to the antibody coupled substrate;

d) eluting the tagged polypeptides bound to the antibody coupled substrate, thereby forming tagged self-antigen polypeptides in an eluted sample;

e) coupling the tagged self-antigen polypeptides in the eluted sample to the second member of a bio-orthogonal coupling pair, wherein the second member of the bio-orthogonal coupling pair is linked to a second substrate, thereby forming self-antigen polypeptides bound to the second substrate;

f) adding a modified protease to the self-antigen polypeptides bound to the second substrate, thereby forming self-antigen peptides, wherein the modified protease comprises a protease; and a first member of a bio-orthogonal coupling pair attached to the protease, wherein the first member is configured to form a covalent bond with a second member of a bio-orthogonal coupling pair;

g) coupling the modified protease to the second member of a bio-orthogonal coupling pair, wherein the second member of the bio-orthogonal coupling pair is linked to the second substrate; and h) eluting the self-antigen peptides.

Clause 44. A method of isolating self-antigen polypeptides, the method comprising:

a) mixing cell or tissue lysate of a second sample with a compound, thereby forming a mixed cell or tissue lysate comprising tagged polypeptides, wherein the compound comprises a first moiety comprising a first member of a bio-orthogonal coupling pair, wherein the first member is configured to form a covalent bond with a second member of a bio-orthogonal coupling pair;

a second moiety configured to form a covalent bond with a polypeptide; and a linker linking the first moiety and the second moiety;

b) coupling the tagged polypeptides in the mixed cell or tissue lysate to an antibody coupled substrate, thereby forming tagged polypeptides bound to the antibody coupled substrate, wherein the antibody coupled substrate comprises antibodies from serum or plasma of a first sample coupled to a first substrate;

c) eluting the tagged polypeptides bound to the antibody coupled substrate, thereby forming tagged self-antigen polypeptides in an eluted sample;

d) coupling the tagged self-antigen polypeptides in the eluted sample to the second member of a bio-orthogonal coupling pair, wherein the second member of the bio-orthogonal coupling pair is linked to a second substrate, thereby forming self-antigen polypeptides bound to the second substrate;

e) adding a modified protease to the self-antigen polypeptides bound to the second substrate, thereby forming self-antigen peptides,
wherein the modified protease comprises
a protease; and
a first member of a bio-orthogonal coupling pair attached to the protease, wherein the first member is configured to form a covalent bond with a second member of a bio-orthogonal coupling pair;

f) coupling the modified protease to the second member of a bio-orthogonal coupling pair, wherein the second member of the bio-orthogonal coupling pair is linked to the second substrate; and g) eluting the self-antigen peptides.

Clause 45. A method of isolating self-antigen polypeptides, the method comprising:

a) coupling tagged polypeptides in a mixed cell or tissue lysate to an antibody coupled substrate, thereby forming tagged polypeptides bound to an antibody coupled substrate,
wherein the antibody coupled substrate comprises antibodies from serum or plasma of a first sample coupled to a first substrate, and
wherein the mixed cell or tissue lysate comprising tagged polypeptides is a mixture of a compound and a cell or tissue lysate from a second sample, the compound comprising
a first moiety comprising a first member of a bio-orthogonal coupling pair, wherein the first member is configured to form a covalent bond with a second member of a bio-orthogonal coupling pair;
a second moiety configured to form a covalent bond with a polypeptide; and
a linker linking the first moiety and the second moiety;

b) eluting the tagged polypeptides bound to the antibody coupled substrate, thereby forming tagged self-antigen polypeptides in an eluted sample;

c) coupling the tagged self-antigen polypeptides in the eluted sample to the second member of a bio-orthogonal coupling pair, wherein the second member of the bio-orthogonal coupling pair is linked to a second substrate, thereby forming self-antigen polypeptides bound to the second substrate;

d) adding a modified protease to the self-antigen polypeptides bound to the second substrate, thereby forming self-antigen peptides,
wherein the modified protease comprises
a protease; and
a first member of a bio-orthogonal coupling pair attached to the protease, wherein the first member is configured to form a covalent bond with a second member of a bio-orthogonal coupling pair;

e) coupling the modified protease to the second member of a bio-orthogonal coupling pair, wherein the second member of the bio-orthogonal coupling pair is linked to the second substrate; and f) eluting the self-antigen peptides.

Clause 46. The method of any one of clauses 40-45, wherein the modified protease is a modified hydrolase and the protease is a hydrolase.

Clause 47. The method of any one of clauses 40-46, wherein the modified protease is a modified serine hydrolase and the protease is a serine hydrolase.

Clause 48. The method of any one of clauses 40-47, wherein the modified protease is a modified trypsin and the protease is a trypsin.

Clause 49. The method of any one of clauses 40-48, wherein the first sample and second sample are autologous samples.

Clause 50. The method of any one of clauses 40-48, wherein the first sample and second sample are allogenic samples.

Clause 51. The method of any one of clauses 40-50, wherein the first sample and second sample are the same blood sample.

Clause 52. The method of any one of clauses 40-50, wherein the first sample and second sample are different blood samples.

Clause 53. The method of any one of clauses 40-50, wherein the first sample is blood, serum or plasma and wherein the second sample is selected from a group consisting of blood, a cell sample, a tissue sample, a tumor sample, a biopsy sample, and a cell culture sample.

Clause 54. The method of any one of clauses 40-53, wherein the first sample and second sample are isolated from a patient having a cancer selected from the group consisting of lung cancer, brain cancer, breast cancer, colorectal cancer, esophageal cancer, kidney cancer, liver cancer, ovarian cancer, pancreatic cancer, prostate cancer, gastric cancer, melanoma, merkel cell carcinoma, leukemia (AML, CLL), non-Hodgkin lymphoma (NHL), gallbladder cancer and cholangiocarcinoma (GBC, CCC), urinary bladder cancer (UBC), and uterine cancer (UEC).

Clause 55. The method of any one of clauses 40-54, wherein the first sample and second sample are isolated from a patient having ovarian cancer.

Clause 56. The method of any one of clauses 40-53, wherein the first sample and second sample are isolated from a patient having an autoimmune disorder.

Clause 57. The method of any one of clauses 40-56, wherein the self-antigen polypeptides are autoantigens or tumor-associated antigens.

Clause 58. The method of any one of clauses 40-57, wherein the second moiety is N-hydroxysuccinimide.

Clause 59. The method of any one of clauses 40-58, wherein the first member of a bio-orthogonal coupling pair is an electron-poor diene, an electron-rich dienophile, or a strained cycloalkene.

Clause 60. The method of any one of clauses 40-59, wherein the first member of a bio-orthogonal coupling pair is a tetrazine moiety selected from the group consisting of a 1,2,4,5-tetrazine moiety or a 4-(1,2,4,5-tetrazinyl)phenyl moiety.

Clause 61. The method of any one of clauses 40-60, wherein the linker is an inert linker.

Clause 62. The method of any one of clauses 40-61, wherein the first substrate is a bead or a solid surface.

Clause 63. The method of any one of clauses 40-62, wherein the first substrate is a magnetic bead.

Clause 64. The method of any one of clauses 40-63, wherein the first substrate is a bead contained within a chromatography column or a spin column.

Clause 65. The method of any one of clauses 40-64, wherein the first substrate is a protein A bead or protein G bead.

Clause 66. The method of any one of clauses 40-65, wherein the second substrate is a bead or a solid surface.

Clause 67. The method of any one of clauses 40-66, wherein the second substrate is a magnetic bead.

Clause 68. The method of any one of clauses 40-67, wherein the second substrate is a bead contained within a chromatography column or a spin column.

Clause 69. The method of any one of clauses 40-64, wherein the second substrate is a porous matrix.

Clause 70. The method of any one of clauses 40-69, wherein the mixed sample or the mixed cell or tissue lysate has a pH greater than 7.

Clause 71. The method of clause 70, wherein the pH greater than 7 ranges from greater than 7 to 10, greater than 7 to 9, or 8 to 9.5.

Clause 72. The method of any one of clauses 40-71, further comprising washing the tagged polypeptides bound to the antibody coupled substrate to remove any unbound materials from the tagged polypeptides bound to the antibody coupled substrate.

Clause 73. The method of any one of clauses 40-72, further comprising washing the self-antigen polypeptides bound to the second substrate using a polar aprotic solvent to remove any unbound materials from the self-antigen polypeptides bound to the second substrate.

Clause 74. A self-antigen isolation kit configured to perform the method of any one of clauses 1-73.

Clause 75. A self-antigen isolation kit comprising a compound comprising a first moiety comprising a first member of a bio-orthogonal coupling pair, wherein the first moiety is configured to form a covalent bond with a second member of a bio-orthogonal coupling pair;

a second moiety configured to form a pH dependent covalent bond with a polypeptide; and a linker linking the first moiety and the second moiety;

a first substrate configured to couple antibodies from serum or plasma of a first sample, wherein the first substrate is used to isolate polypeptides having an affinity to antibodies coupled to the first substrate; and a second substrate linked to a second member of a bio-orthogonal coupling pair, wherein the second substrate is used to isolate self-antigen polypeptides bonded to the compound.

Clause 76. The self-antigen isolation kit of clause 75, further comprising a modified protease comprising a protease; and a first member of a bio-orthogonal coupling pair attached to the protease, wherein the first member is configured to form a covalent bond with a second member of a bio-orthogonal coupling pair.

Clause 77. A self-antigen isolation kit comprising a compound comprising a first moiety comprising a first member of a bio-orthogonal coupling pair, wherein the first moiety is configured to form a covalent bond with a second member of a bio-orthogonal coupling pair;

a second moiety configured to form a covalent bond with a polypeptide; and a linker linking the first moiety and the second moiety;

a first substrate configured to couple antibodies from serum or plasma of a first sample, wherein the first substrate is used to isolate polypeptides having an affinity to antibodies coupled to the first substrate;

a second substrate linked to a second member of a bio-orthogonal coupling pair, wherein the second substrate is used to isolate self-antigen polypeptides bonded to the compound; and a modified protease comprising a protease; and a first member of a bio-orthogonal coupling pair attached to the protease, wherein the first member is configured to form a covalent bond with a second member of a bio-orthogonal coupling pair.

Clause 78. The self-antigen isolation kit of any one of clauses 76 or 77, wherein the modified protease is a modified hydrolase and the protease is a hydrolase.

Clause 79. The self-antigen isolation kit of any one of clauses 76-78, wherein the modified protease is a modified serine hydrolase and the protease is a serine hydrolase.

Clause 80. The self-antigen isolation kit of any one of clauses 76-79, wherein the modified protease is a modified trypsin and the protease is a trypsin.

Definitions

In addition to the definitions previously set forth herein, the following definitions are relevant to the present disclosure.

As used herein, "tag", "tagged", or "tagging" refers to coupling compound 1 or compound 2 to amines of a polypeptide, thereby bonding the compound to the polypeptide. For example, carboxylic anhydride of compound 1 forms a pH dependent covalent bond with the amines of the polypeptide. For example, N-hydroxysuccinimide of compound 2 forms a permanent covalent bond with the amines of the polypeptide.

As used herein, "pH dependent-tagged polypeptide" refers to a polypeptide with a pH dependent covalent bond between amines of the polypeptide and compound 1. For example, a pH dependent-tagged polypeptide can have a pH dependent covalent bond between amines of the polypeptide and carboxylic anhydride of compound 1. The pH dependent covalent bond between amines of the polypeptide and carboxylic anhydride of compound 1 can be reversed (i.e., cleaved) by using an elution buffer with a pH less than 7 (e.g., 2 to less than 7, 3 to less than 7, or from 2.5 to 6).

As used herein, "permanently tagged polypeptide" refers to a polypeptide with a permanent covalent bond between amines of the polypeptide and compound 2. For example, a permanently tagged polypeptide can have a permanent covalent bond between amines of the polypeptide and N-hydroxysuccinimide of compound 2. The permanent covalent bond between amines of the polypeptide and carboxylic anhydride of compound 2 is stable and cannot be reversed at a pH of 2 to 12, a temperature of less than 100° C., and an exposure time of less than 24 hours. Instead, the permanent covalent bond can only be broken by exposing the permanently tagged polypeptides to extreme conditions outside the pH, temperature and time ranges described above, such as for example, boiling the permanently tagged polypeptides in 6N hydrochloric acid for 24 hours.

A "moiety" (pl. "moieties") is a part of a chemical compound, and includes groups, such as functional groups. As such, a nucleobase moiety is a nucleobase that is modified by attachment to another compound moiety, such as a polymer monomer, e.g. the nucleic acid or nucleic acid analog monomers described herein, or a polymer, such as a nucleic acid or nucleic acid analog as described herein.

A "polypeptide" includes proteins and oligopeptides as a class, and generally refers to a polypeptide comprising two or more amino acid residues, though typically referring to longer amino acid chains.

As used herein, "self-antigen polypeptide" also known as an "autoantigen polypeptide" refers to a polypeptide within an organism against which autoantibodies are directed.

As used herein, "autoantibodies" refer to antibodies produced by the immune system of an organism directed against one or more of the organism's own polypeptides.

As used herein, "at least one of" a list of elements means one of the elements or any combination of two or more of the listed elements. As an example "at least one of A, B, and C" means A only; B only; C only; A and B; A and C; B and C; or A, B, and C.

Various features and characteristics are described in this specification to provide an understanding of the composition, structure, production, function, and/or operation of the invention, which includes the disclosed compositions, kits, and methods. It is understood that the various features and characteristics of the invention described in this specification can be combined in any suitable manner, regardless of whether such features and characteristics are expressly described in combination in this specification. The Inventors and the Applicant expressly intend such combinations of features and characteristics to be included within the scope of the invention described in this specification. As such, the claims can be amended to recite, in any combination, any features and characteristics expressly or inherently described in, or otherwise expressly or inherently supported by, this specification. Furthermore, the Applicant reserves the right to amend the claims to affirmatively disclaim features and characteristics that may be present in the prior art, even if those features and characteristics are not expressly described in this specification. Therefore, any such amendments will not add new matter to the specification or claims and will comply with the written description, sufficiency of description, and added matter requirements.

Any numerical range recited in this specification describes all sub-ranges of the same numerical precision (i.e., having the same number of specified digits) subsumed within the recited range. For example, a recited range of "1.0 to 10.0" describes all sub-ranges between (and including) the recited minimum value of 1.0 and the recited maximum value of 10.0, such as, for example, "2.4 to 7.6," even if the range of "2.4 to 7.6" is not expressly recited in the text of the specification. Accordingly, the Applicant reserves the right to amend this specification, including the claims, to expressly recite any sub-range of the same numerical precision subsumed within the ranges expressly recited in this specification. All such ranges are inherently described in this specification such that amending to expressly recite any such sub-ranges will comply with the written description, sufficiency of description, and added matter requirements.

Also, unless expressly specified or otherwise required by context, all numerical parameters described in this specification (such as those expressing values, ranges, amounts, percentages, and the like) may be read as if prefaced by the word "about," even if the word "about" does not expressly appear before a number. Additionally, numerical parameters described in this specification should be construed in light of the number of reported significant digits, numerical precision, and by applying ordinary rounding techniques. It is also understood that numerical parameters described in this specification will necessarily possess the inherent variability characteristic of the underlying measurement techniques used to determine the numerical value of the parameters.

Notwithstanding that numerical ranges and parameters setting forth the broad scope of the invention are approximations, numerical values set forth in the specific examples are reported precisely as possible. Any numerical value, however, inherently contains certain errors necessarily resulting from the standard variation found in its respective testing measurements.

Reference throughout the specification to "certain embodiments," "certain other embodiments," "one embodiment," "an embodiment," or the like means that a particular feature, structure, step, or characteristic described in connection with the example is included in at least one embodiment. Thus, appearances of the phrases "certain embodiments," "certain other embodiments," "one embodiment," "an embodiment," or the like, in places throughout the specification are not necessarily all referring to the same embodiment. Furthermore, the particular described features, structures, steps, or characteristics may be combined in any suitable manner in one or more embodiments. Thus, the particular features, structures, steps, or characteristics illustrated or described in connection with one embodiment may be combined, in whole or in part, with the features, structures, steps, or characteristics of one or more other embodiments without limitation. Such modifications and variations are intended to be included within the scope of the present embodiments.

Any patent, publication, or other document identified in this specification is incorporated by reference into this specification in its entirety unless otherwise indicated but only to the extent that the incorporated material does not conflict with existing descriptions, definitions, statements, illustrations, or other disclosure material expressly set forth in this specification. As such, and to the extent necessary, the express disclosure as set forth in this specification supersedes any conflicting material incorporated by reference. Any material, or portion thereof, that is incorporated by reference into this specification, but which conflicts with existing definitions, statements, or other disclosure material set forth herein, is only incorporated to the extent that no conflict arises between that incorporated material and the existing disclosure material. Applicant reserves the right to amend this specification to expressly recite any subject matter, or portion thereof, incorporated by reference. The amendment of this specification to add such incorporated subject matter will comply with the written description, sufficiency of description, and added matter requirements.

It is understood that the inventions described in this specification are not limited to the examples summarized in the Summary or Detailed Description. Various other aspects are described and exemplified herein.

EXAMPLES

The present disclosure will be more fully understood by reference to the following examples, which provide illustrative, non-limiting aspects of the present disclosure.

Example 1—Forming an Antibody Coupled Substrate Using Serum

Whole blood was collected in a tube from a healthy person or a patient having cancer, an autoimmune disease, or other disease/disorder. The blood was allowed to clot by leaving it undisturbed at room temperature for 15-30 minutes. The clot was then removed by centrifuging the tube at 1,000-2,000×g for 10 minutes in a refrigerated centrifuge. The resulting supernatant was serum.

Figure 5:
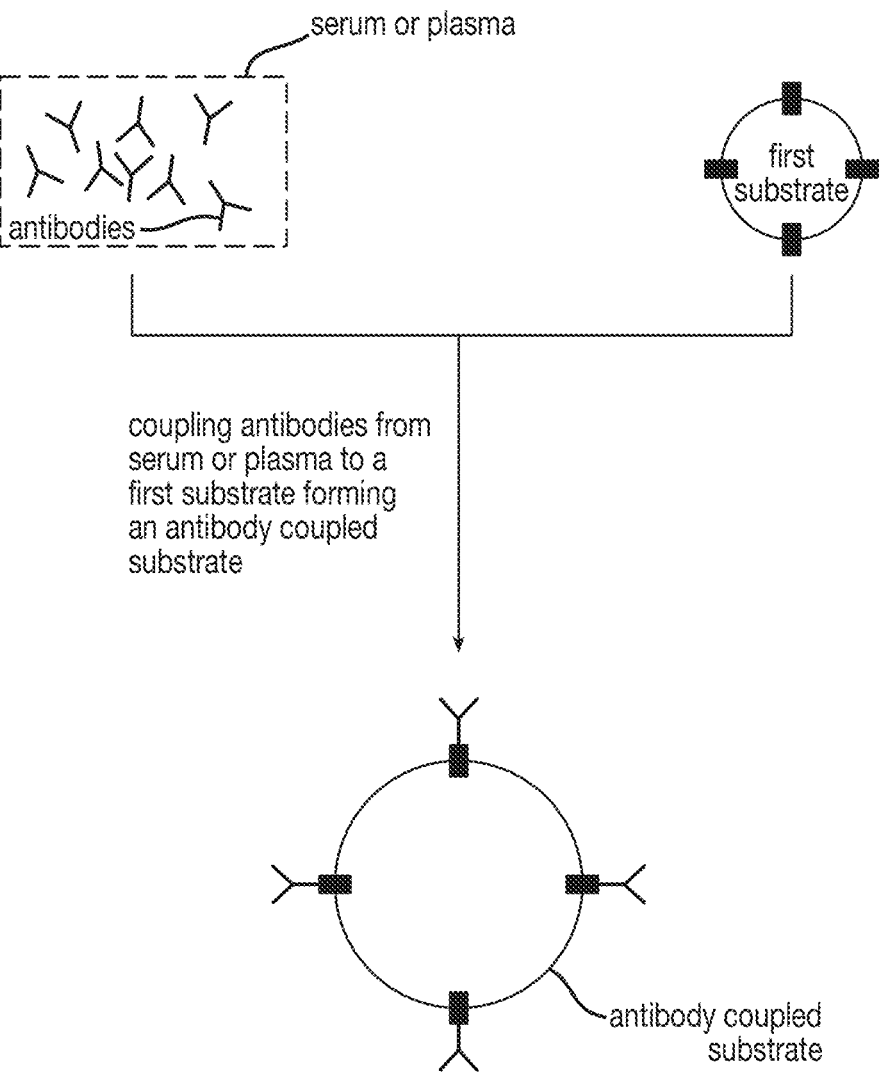
FIG. 5 shows a schematic for forming an antibody coupled substrate.

10 μl of the serum was then mixed with 10 μl of a first substrate (i.e. Protein A beads, such as PrismA beads from Cytiva, Massachusetts, USA) for at least 45 minutes, forming an antibody coupled substrate, as illustrated in FIG. 5. The antibody coupled substrate was washed with a wash solution (e.g., 100 mM Hepes pH 8, 500 mM NaCl, 1% IGEPAL) to wash away all non-immunoglobulin proteins so that only antibodies from the heathy person's serum or patient's serum were bound to the Protein A beads.

Example 2—Forming an Antibody Coupled Substrate Using Plasma

Whole blood was collected from a healthy person or a patient having cancer, an autoimmune disease, or other disease/disorder in a commercially available anticoagulant-treated tube (e.g., EDTA treated tubes). Red blood cells were removed from plasma by centrifuging the tube at 1,000-2,000×g for 10 minutes in a refrigerated centrifuge. The refrigerated centrifuge tube was further centrifuged for 15 minutes at 2,000×g to deplete platelets in the plasma sample. The resulting supernatant was plasma.

10 μl of the plasma was then mixed with 10 μl of a first substrate (i.e., Protein A beads), forming an antibody coupled substrate, as illustrated in FIG. 5. The antibody coupled substrate was washed with a wash solution (e.g., 100 mM Hepes pH 8, 500 mM NaCl, 1% IGEPAL) to wash away all non-immunoglobulin proteins so that only antibodies from the healthy person's plasma or patient's plasma were bound to the Protein A beads.

Example 3—Coupling pH Dependent Tagged Polypeptides to an Antibody Coupled Substrate A cell or tissue sample was centrifuged in a benchtop centrifuge to form a cell pellet. Lysis buffer (100 mM Hepes pH 8, 500 mM NaCl, 1% IGEPAL, 1 mM EDTA, 1 mM Phenylmethylsulfonyl fluoride (PMSF), 10 μg/ml Leupeptin, 10 μg/ml pepstatin) was added to the cell pellet and mixed, thereby forming a cell or tissue lysate. EDTA, PMSF, Leupeptin, and pepstatin were included in the lysis buffer to inhibit proteases. The cell or tissue lysate was sonicated to break up any DNA present in the lysate. Sonication conditions included: 20 blasts at 30% power, 30% duty cycle, on ice followed by centrifugation at 15,000×g for 20 minutes. The protein concentration of the cell or tissue lysate was assayed using BCA Protein Assay (available from Thermo Fisher Scientific, Pennsylvania, USA).

The cell or tissue lysate including 100 μg protein was mixed with 2.1 μl of 30 mg/ml mTet-PEG$_n$-CDM in 90% acetonitrile, 0.1% trifluoracetic acid (see FIG. 2) by pipetting the mixture gently and then incubating it for 30 minutes at 4° C. to form pH dependent tagged polypeptides in the cell or tissue lysate.

Free (un-reacted) mTet-PEG$_n$-CDM was quenched by the addition of 20 μl 5M methylamine, 10 mM Hepes pH 8 for 30 minutes at 4° C.

After 30 minutes, the mixed cell or tissue lysate (which includes the pH dependent tagged polypeptides) was added to the antibody coupled substrate prepared in Example 1 or Example 2 at 4° C. with gentle rotation for 120 minutes to form pH dependent tagged polypeptides bound to the antibody coupled substrate, as illustrated in FIG. 6.

After 120 minutes, the pH dependent tagged polypeptides bound to the antibody coupled substrate were washed with a wash solution (e.g., 100 mM Hepes pH 8, 500 mM NaCl, 1% IGEPAL) to wash away all unbound tagged polypeptides so that only pH dependent tagged polypeptides were bound that have an affinity to antibodies coupled to the antibody coupled substrate.

Example 4—Coupling pH Dependent Tagged Self-Antigen Polypeptides to a Second Substrate The pH dependent tagged polypeptides bound to the antibody coupled substrate in Example 3 were eluted from the antibody coupled substrate by adding a solution (e.g., 100 mM Hepes pH 8, 100 mM NaCl, 1% SDS) at room temperature with gentle rotation for two separate 10 minute incubations, forming pH dependent tagged self-antigen polypeptides in an eluted sample. The eluted sample also contained antibodies that had previously been bound to the antibody coupled substrate.

The eluted sample was added directly to a second substrate (e.g., a capture resin, such as TCO beads) positioned within a resin capture tube. The resin capture tube is a spin column tube with a fine slit in the tip of the centrifuge tube. The slit is so fine that TCO-beads are retained within the tube while liquid passes through the slit under centrifugal force. A second member of a bio-orthogonal coupling pair (e.g. TCO) was linked to the capture resin. The second member forms a covalent bond with the first member of a bio-orthogonal coupling pair of the pH dependent tagged self-antigen polypeptides.

The resin capture tube was then incubated at room temperature with gentle rotation for 15 minutes, thereby forming pH dependent tagged self-antigen polypeptides bound to the second substrate (pH dependent tagged self-antigen polypeptides bound to the capture resin).

A washing step was performed by adding 200 μl of wash buffer #1 (250 mM NaCl, 10% acetonitrile, 100 mM HEPES pH 8) to the resin capture tube positioned within a waste collection tube, vortexing it for 1 second, and centrifuging it briefly for 2-6 seconds in a benchtop centrifuge until all of the liquid had passed through into the waste collection tube. The liquid in the waste collection tube was discarded.

A second washing step was performed by adding 200 μl of wash buffer #2 (75% acetonitrile, 25%100 mM HEPES pH 8) to the resin capture tube positioned within a waste collection tube, vortexing it for 1 second, and centrifuging it briefly for 2-6 seconds in a benchtop centrifuge until all of the liquid had passed into the waste collection tube. The liquid in the waste collection tube was discarded.

A final washing step was performed by adding 200 μl of ultrapure water to the resin capture tube positioned within a waste collection tube, vortexing it for 1 second, and centrifuging it briefly for 2-6 seconds in a benchtop centrifuge until all of the liquid had passed into the waste collection tube. The liquid in the waste collection tube was discarded. The final washing step was performed one additional time.

Example 5—Removing PH Dependent Tagged Self-Antigen Polypeptides from the Second Substrate After the final washing step in Example 4, 50 μl of elution buffer (e.g., 100 mM formic acid) was added to the capture resin positioned within the resin capture tube. The tube was incubated at room temperature with gentle rotation for 15 minutes to release the self-antigen polypeptides from the capture resin.

Example 6—Protein Digestion of pH Dependent Tagged Self-Antigen Polypeptides Released from the Second Substrate After the 15-minute incubation at room temperature in Example 5, the resin capture tube was inserted into a low protein binding collection tube and 25 μl of a modified trypsin was directly added to the capture resin. The resin capture tube was gently tapped to mix its contents and then incubated at 37° C. for 1 hour. After 1 hour, the resin capture tube positioned in the low protein binding collection tube was centrifuged for 2-6 seconds in a benchtop centrifuge until all of the liquid had passed into the low protein binding collection tube. The liquid that passed into the low protein binding collection tube included self-antigen peptides.

50 μl of elution buffer elution (e.g., 100 mM formic acid) was directly added to the capture resin in the resin capture tube. The resin capture tube was gently tapped to mix its contents and then incubated at room temperature with gentle rotation for 5 minutes. The resin capture tube was inserted back into the low protein binding collection tube and centrifuged for 5-10 seconds in a benchtop centrifuge until all of the liquid had passed into the low protein binding collection tube. This additional liquid that passed into the low protein binding collection tube also included self-antigen peptides.

The self-antigen peptides were further analyzed by Liquid Chromatography-Mass Spectrometry (LC-MS/MS) to determine the mass of the self-antigen peptides and their purity. MS was also used to determine the amino acid sequence of the self-antigen peptides to further characterize the proteins being studied or identified.

Example 7—Coupling Permanently Tagged Polypeptides to an Antibody Coupled Substrate A cell or tissue sample was centrifuged in a benchtop centrifuge to form a cell pellet. Lysis buffer (100 mM Hepes pH 8, 500 mM NaCl, 1% IGEPAL, 1 mM EDTA, 1 mM Phenylmethylsulfonyl fluoride (PMSF), 10 μg/ml Leupeptin, 10 μg/ml pepstatin) was added to the cell pellet and mixed, thereby forming a cell or tissue lysate. EDTA, PMSF, Leupeptin, and pepstatin were included in the lysis buffer to inhibit proteases. The cell or tissue lysate was sonicated to break up any DNA present in the lysate. Sonication conditions included: 20 blasts at 30% power, 30% duty cycle, on ice followed by centrifugation at 15,000×g for 20 minutes. The protein concentration of the cell or tissue lysate was assayed using BCA Protein Assay.

The cell or tissue lysate including 100 μg protein was mixed with 2.1 μl of 30 mg/ml mTet-PEG$_n$-NHS in dimethylformamide (see FIG. 4) by pipetting the mixture gently and then incubating it for 30 minutes at 4° C. to form permanently tagged polypeptides in the cell or tissue lysate.

Free (un-reacted) mTet-PEG$_n$-NHS was quenched by the addition of 20 μl 5M methylamine, 10 mM Hepes pH 8 for 30 minutes at 4° C.

After 30 minutes, the mixed cell or tissue lysate (which includes permanently tagged polypeptides) was added to the antibody coupled substrate prepared in Example 1 or Example 2 at 4° C. with gentle rotation for 120 minutes to form permanently tagged polypeptides bound to the antibody coupled substrate, as illustrated in FIG. 7.

After 120 minutes, the permanently tagged polypeptides bound to the antibody coupled substrate were washed with a wash solution (e.g., 100 mM Hepes pH 8, 500 mM NaCl, 1% IGEPAL) to wash away all unbound tagged polypeptides so that only permanently tagged polypeptides were bound that have an affinity to antibodies coupled to the antibody coupled substrate.

Example 8—Coupling Permanently Tagged Self-Antigen Polypeptides to a Second Substrate The permanently tagged polypeptides bound to the antibody coupled substrate in Example 7 were eluted from the antibody coupled substrate by adding a solution (e.g., 100 mM Hepes pH 8, 100 mM NaCl, 1% SDS) at room temperature with gentle rotation for two separate 10 minute incubations, forming permanently tagged self-antigen polypeptides in an eluted sample. The eluted sample also contained antibodies that had previously been bound to the antibody coupled substrate.

The eluted sample was added directly to a second substrate (e.g., capture resin such as TCO beads) positioned within a resin capture tube. A second member of a bio-orthogonal coupling pair (e.g. TCO) was linked to the capture resin. The second member forms a covalent bond with the first member of a bio-orthogonal coupling pair of the permanently tagged self-antigen polypeptides.

The resin capture tube was then incubated at room temperature with gentle rotation for 15 minutes, thereby forming permanently tagged self-antigen polypeptides bound to the second substrate (permanently tagged self-antigen polypeptides bound to the capture resin).

A washing step was performed by adding 200 μl of wash buffer #1 (250 mM NaCl, 10% acetonitrile, 100 mM HEPES pH 8) to the resin capture tube positioned within a waste collection tube, vortexing it for 1 second, and centrifuging it briefly for 2-6 seconds in a benchtop centrifuge until all of the liquid had passed through into the waste collection tube. The liquid in the waste collection tube was discarded.

A second washing step was performed by adding 200 μl of wash buffer #2 (75% acetonitrile, 25%100 mM HEPES pH 8) to the resin capture tube positioned within a waste collection tube, vortexing it for 1 second, and centrifuging it briefly for 2-6 seconds in a benchtop centrifuge until all of the liquid had passed into the waste collection tube. The liquid in the waste collection tube was discarded.

A final washing step was performed by adding 200 μl of ultrapure water to the resin capture tube positioned within a waste collection tube, vortexing it for 1 second, and centrifuging it briefly for 2-6 seconds in a benchtop centrifuge until all of the liquid had passed into the waste collection tube. The liquid in the waste collection tube was discarded. The final washing step was performed one additional time.

Example 9—Protein Digestion of Permanently Tagged Polypeptides Bound to a Second Substrate After the final washing step in Example 8, the resin capture tube was inserted into a low protein binding collection tube and 25 μl of a modified trypsin was directly added to the capture resin. The resin capture tube was gently tapped to mix its contents and then incubated at 37° C. for 1 hour. After 1 hour, the resin capture tube positioned in the low protein binding collection tube was centrifuged for 2-6 seconds in a benchtop centrifuge until all of the liquid had passed into the low protein binding collection tube. The liquid that passed into the low protein binding collection tube included self-antigen peptides.

50 μl of elution buffer elution (e.g., 100 mM formic acid) was directly added to the capture resin in the resin capture tube. The resin capture tube was gently tapped to mix its contents and then incubated at room temperature with gentle rotation for 5 minutes. The resin capture tube was inserted back into the low protein binding collection tube and centrifuged for 5-10 seconds in a benchtop centrifuge until all of the liquid had passed into the low protein binding collection tube. This additional liquid that passed into the low protein binding collection tube also included self-antigen peptides.

The self-antigen peptides were further analyzed by LC-MS/MS to determine the mass of the self-antigen peptides and their purity. MS was also used to determine the amino acid sequence of the self-antigen peptides to further characterize the proteins being studied or identified.

Example 10—Capture and Elution of Tagged Polypeptides from TCO Beads

HeLa cells (available from ATCC®, Virginia, USA) were centrifuged in a benchtop centrifuge to form a cell pellet. Lysis buffer (100 mM Hepes pH 8, 500 mM NaCl, 1% IGEPAL, 1 mM EDTA, 1 mM Phenylmethylsulfonyl fluoride (PMSF), 10 μg/ml Leupeptin, 10 μg/ml pepstatin) was added to the cell pellet and mixed, thereby forming a HeLa cell lysate. The HeLa cell lysate was sonicated to break up any DNA present in the lysate. Sonication conditions included: 20 blasts at 30% power, 30% duty cycle, on ice followed by centrifugation at 15,000×g for 20 minutes. The protein concentration of the HeLa cell lysate was assayed using BCA Protein Assay.

HeLa cell lysate samples including 100 μg protein were mixed with mTet-PEG$_n$-CDM (see FIG. 2) in 90% acetonitrile, 0.1% trifluoracetic acid by pipetting the mixture gently and then incubating it for 30 minutes at 4° C. to form pH dependent tagged polypeptides in the HeLa cell lysate. Different amounts of mTet-PEG$_n$-CDM per μg of lysate were used for each sample. For example, sample 1 included 0 μg mTet-PEG$_n$-CDM per μg of lysate, sample 2 included 0.15 μg mTet-PEG$_n$-CDM per μg of lysate, sample 3 included 0.3 μg mTet-PEG$_n$-CDM per μg of lysate, sample 4 included 0.6 μg mTet-PEG$_n$-CDM per μg of lysate, and sample 5 included 0.9 μg mTet-PEG$_n$-CDM per μg of lysate.

After 30 minutes, the mixed HeLa cell lysate (which included the pH dependent tagged polypeptides) was added directly to a capture resin (TCO beads) positioned within a resin capture tube. The resin capture tube was then incubated at room temperature with gentle rotation for 15 minutes, thereby forming pH dependent tagged polypeptides bound to the capture resin.

Figure 9A:
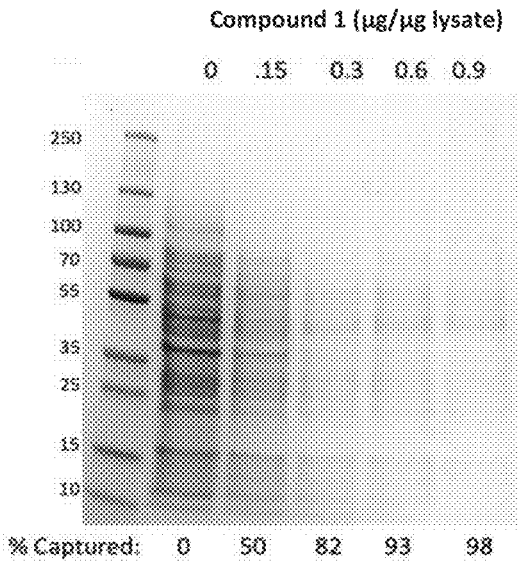
FIG. 9A is an SDS-PAGE gel showing the amount of polypeptides from a HeLa cell lysate that bind to trans-cyclooctene (TCO) beads when the HeLa cell lysate is mixed with varying amounts of mTet-PEG$_n$-CDM.

FIG. 9A shows that 0% of the polypeptides in the mixed HeLa cell lysate of sample 1 were bound to the capture resin, 50% of the polypeptides in the mixed HeLa cell lysate of sample 2 were bound to the capture resin, 82% of the polypeptides in the mixed HeLa cell lysate of sample 3 were bound to the capture resin, 93% of the polypeptides in the mixed HeLa cell lysate of sample 4 were bound to the capture resin, and 98% of the polypeptides in the mixed HeLa cell lysate of sample 5 were bound to the capture resin.

After the pH dependent tagged polypeptides bound to the capture resin, a washing step was performed by adding 200 μl of wash buffer #1 (250 mM NaCl, 10% acetonitrile, 100 mM HEPES pH 8) to the resin capture tube positioned within a waste collection tube, vortexing it for 1 second, and centrifuging it briefly for 2-6 seconds in a benchtop centrifuge until all of the liquid had passed through into the waste collection tube. The liquid in the waste collection tube was discarded.

A second washing step was performed by adding 200 μl of wash buffer #2 (75% acetonitrile, 25%100 mM HEPES pH 8) to the resin capture tube positioned within a waste collection tube, vortexing it for 1 second, and centrifuging it briefly for 2-6 seconds in a benchtop centrifuge until all of the liquid had passed into the waste collection tube. The liquid in the waste collection tube was discarded.

A final washing step was performed by adding 200 μl of ultrapure water to the resin capture tube positioned within a waste collection tube, vortexing it for 1 second, and centrifuging it briefly for 2-6 seconds in a benchtop centrifuge until all of the liquid had passed into the waste collection tube. The liquid in the waste collection tube was discarded. The final washing step was performed one additional time.

After the final washing step, 50 μl of elution buffer (e.g., 100 mM formic acid) was added to the capture resin positioned within the resin capture tube. The tube was incubated at room temperature with gentle rotation for 15 minutes to release the polypeptides from the capture resin.

Figure 9B:
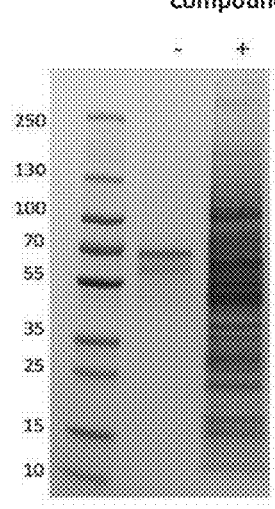
FIG. 9B is an SDS-PAGE gel showing the amount of polypeptides recovered from mTet-PEG$_n$-CDM tagged polypeptides coupled to TCO beads.

FIG. 9B shows the amount of polypeptides recovered from HeLa cell lysates when mixed with mTet-PEG$_n$-CDM (Compound 1, +) versus polypeptides recovered from HeLa cell lysates when not mixed with mTet-PEG$_n$-CDM (Compound 1,–). FIG. 9B shows high amounts of polypeptides eluted (recovered) from the capture resin when mTet-PEG$_n$-CDM was added to the HeLa cell lysate (Compound 1, +) and low amounts of polypeptides eluted (recovered) from the capture resin when mTet-PEG$_n$-CDM was not added to the HeLa cell lysate (Compound 1, –).

These experiments in FIG. 9A and FIG. 9B demonstrate that adding compound 1 (mTet-PEG$_n$-CDM) to HeLa cell lysates to form pH dependent tagged polypeptides provides at least 98% capture of the polypeptides present in the HeLa cell lysate and, also allows for the recovery of the captured polypeptides after elution.

Example 11—Capture and Elution of Purified Self-Antigen Polypeptides

HeLa cells were centrifuged in a benchtop centrifuge to form a cell pellet. Lysis buffer (100 mM Hepes pH 8, 500 mM NaCl, 1% IGEPAL, 1 mM EDTA, 1 mM Phenylmethylsulfonyl fluoride (PMSF), 10 μg/ml Leupeptin, 10 μg/ml pepstatin) was added to the cell pellet and mixed, thereby forming a HeLa cell lysate. The HeLa cell lysate was sonicated to break up any DNA present in the lysate. Sonication conditions included: 20 blasts at 30% power, 30% duty cycle, on ice followed by centrifugation at 15,000×g for 20 minutes. The protein concentration of the HeLa cell lysate was assayed using BCA Protein Assay.

The HeLa cell lysate samples including 100 μg protein were mixed with 2.1 μl of 30 mg/ml mTet-PEG$_n$-CDM in 90% acetonitrile, 0.1% trifluoracetic acid (see FIG. 2) by pipetting the mixture gently and then incubating it for 30 minutes at 4° C. to form pH dependent tagged polypeptides in the mixed HeLa cell lysate.

Free (un-reacted) mTet-PEG$_n$-CDM was quenched by the addition of 20 μl 5M methylamine, 10 mM Hepes pH 8 for 30 minutes at 4° C.

An antibody coupled substrate having anti-Hsp90 antibodies was prepared for immunoprecipitation by mixing 1 μg anti-Hsp90 with 10 μl of a first substrate (e.g. Protein A beads) for at least 45 minutes. The antibody coupled substrate having anti-Hsp90 antibodies was washed with a wash solution (e.g., 100 mM Hepes pH 8, 500 mM NaCl, 1% IGEPAL) to wash away all non-immunoglobulin proteins so that only anti-Hsp90 antibodies were bound to the Protein A beads.

Another antibody coupled substrate having anti-Hsp90 antibodies and anti-glycyl-tRNA synthetase antibodies was prepared for immunoprecipitation by mixing 1 µg anti-Hsp90, 10 µl of serum of a patient with an autoimmune disorder, and 10 µl of a first substrate (e.g. Protein A beads) for at least 45 minutes. The autoimmune patient's serum includes antibodies against glycyl-tRNA synthetase autoantigens. The antibody coupled substrate having anti-Hsp90 antibodies and anti-glycyl-tRNA synthetase antibodies was washed with a wash solution (e.g., 100 mM Hepes pH 8, 500 mM NaCl, 1% IGEPAL) to wash away all non-immunoglobulin proteins so that only anti-Hsp90 antibodies, anti-glycyl-tRNA synthetase antibodies, and other antibodies from the autoimmune patient's serum were bound to the Protein A beads.

A mixed HeLa cell lysate (including pH dependent tagged polypeptides) was added to the antibody coupled substrate having anti-Hsp90 antibodies at 4° C. with gentle rotation for 120 minutes to form pH dependent tagged polypeptides bound to the antibody coupled substrate. After 120 minutes, the antibody coupled substrate having anti-Hsp90 antibodies was washed with a wash solution (e.g., 100 mM Hepes pH 8, 500 mM NaCl, 1% IGEPAL) to wash away all unbound tagged polypeptides so that only pH dependent tagged polypeptides were bound that have an affinity to antibodies coupled to the antibody coupled substrate. Next, the pH dependent tagged polypeptides bound to the antibody coupled substrate having anti-Hsp90 antibodies were eluted by treating the antibody coupled substrate with a solution (e.g., 100 mM Hepes pH 8, 100 mM NaCl, 1% SDS) at room temperature with gentle rotation for two separate 10 minute incubations to release the pH dependent tagged polypeptides, thereby forming tagged self-antigen polypeptides in an eluted sample, as described in Example 4. The eluted sample also contained antibodies that had previously been bound to the antibody coupled substrate. The eluted sample (including the pH dependent tagged self-antigen polypeptides) was added to a second substrate (e.g. TCO beads) as described in Example 4. The self-antigen polypeptides were then eluted from the second substrate as described in Example 5. This sample is represented in lane 1 (human serum, –) of FIG. 10 and includes purified Hsp90 polypeptides.

A separate mixed HeLa cell lysate (including pH dependent tagged polypeptides) was added to the antibody coupled substrate having anti-Hsp90 antibodies and anti-glycyl-transfer RNA synthetase antibodies at 4° C. with gentle rotation for 120 minutes to form pH dependent tagged polypeptides bound to the antibody coupled substrate. After 120 minutes, the antibody coupled substrate having anti-Hsp90 and anti-glycyl-transfer RNA synthetase antibodies was washed with a wash solution (e.g., 100 mM Hepes pH 8, 500 mM NaCl, 1% IGEPAL) to wash away all unbound tagged polypeptides so that only pH dependent tagged polypeptides were bound that have an affinity to antibodies coupled to the antibody coupled substrate. Next, the pH dependent tagged polypeptides bound to the antibody coupled substrate having anti-Hsp90 antibodies and anti-glycyl-transfer RNA synthetase antibodies were eluted by treating the antibody coupled substrate with a solution (e.g., 100 mM Hepes pH 8, 100 mM NaCl, 1% SDS) at room temperature with gentle rotation for two separate 10 minute incubations to release the pH dependent tagged polypeptides, thereby forming pH dependent tagged self-antigen polypeptides (i.e. Hsp90 and glycyl-transfer RNA synthetase) in an eluted sample, as described in Example 4. The eluted sample also contained antibodies that had previously been bound to the antibody coupled substrate. The eluted sample (including the pH dependent tagged self-antigen polypeptides) was added to a second substrate (e.g. TCO beads) as described in Example 4. The self-antigen polypeptides were then eluted from the second substrate as described in Example 5. This sample is represented in lane 2 (human serum, +) of FIG. 10 and includes purified Hsp90 polypeptides and purified glycyl-transfer RNA synthetase.

Figure 10:
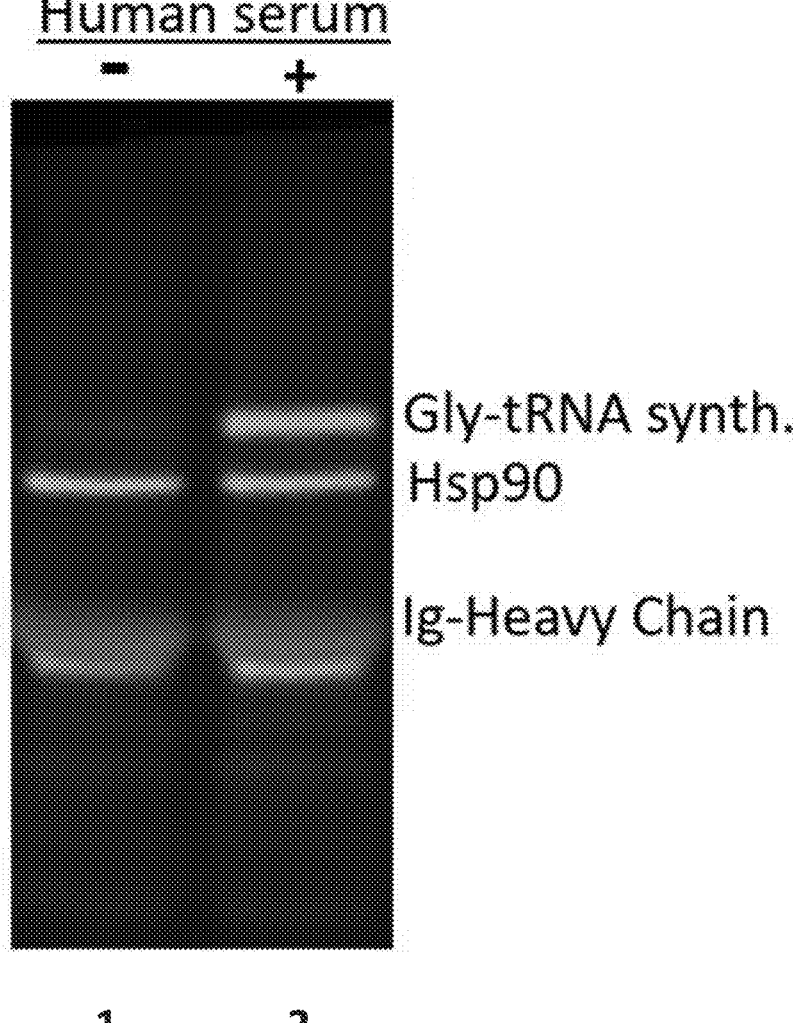
FIG. 10 is an SDS-PAGE gel showing eluted self-antigen polypeptides.

The experiment in FIG. 10 demonstrates that the disclosed method of isolating self-antigen polypeptides is capable of isolating and identifying self-antigen polypeptides, such as Hsp90 and glycyl-transfer RNA synthetase.

Example 12—Capture and Elution of Purified Self-Antigen Polypeptides without Immunoglobulin Contamination HeLa cells were centrifuged in a benchtop centrifuge to form a cell pellet. Lysis buffer (100 mM Hepes pH 8, 500 mM NaCl, 1% IGEPAL, 1 mM EDTA, 1 mM Phenylmethylsulfonyl fluoride (PMSF), 10 µg/ml Leupeptin, 10 µg/ml pepstatin) was added to the cell pellet and mixed, thereby forming a HeLa cell lysate. The HeLa cell lysate was sonicated to break up any DNA present in the lysate. Sonication conditions included: 20 blasts at 30% power, 30% duty cycle, on ice followed by centrifugation at 15,000×g for 20 minutes. The protein concentration of the HeLa cell lysate was assayed using BCA Protein Assay.

The HeLa cell lysate samples including 100 µg protein was mixed with 2.1 µl of 30 mg/ml mTet-PEG$_n$-CDM in 90% acetonitrile, 0.1% trifluoracetic acid (see FIG. 2) by pipetting the mixture gently and then incubating it for 30 minutes at 4° C. to form pH dependent tagged polypeptides in the mixed HeLa cell lysate.

Free (un-reacted) mTet-PEG$_n$-CDM was quenched by the addition of 20 µl 5M methylamine, 10 mM Hepes pH 8 for 30 minutes at 4° C.

An antibody coupled substrate having anti-Hsp90 antibodies and anti-Topo I antibodies was prepared by mixing 1 µg anti-Hsp90, 1 µg anti-Topo I, and 10 µl of a first substrate (e.g. Protein A beads) for at least 45 minutes. The antibody coupled substrate having anti-Hsp90 antibodies and anti-Topo I antibodies was washed with a wash solution (e.g., 100 mM Hepes pH 8, 500 mM NaCl, 1% IGEPAL) to wash away all non-immunoglobulin proteins so that only anti-Hsp90 antibodies and anti-Topo I antibodies were bound to the Protein A beads.

Figure 11:
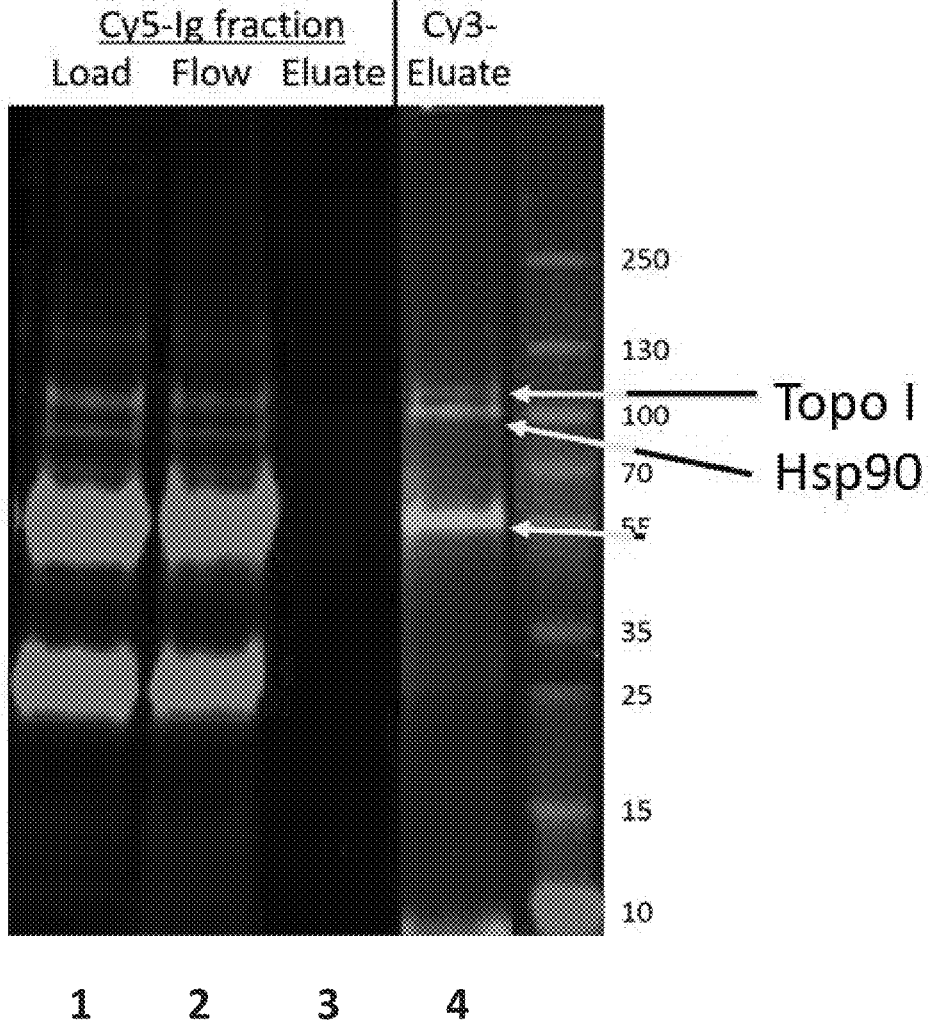
FIG. 11 is an SDS-PAGE gel showing eluted self-antigen polypeptides and eluted contaminating antibodies in separate elution samples.

A mixed HeLa cell lysate (including pH dependent tagged polypeptides) was added to the antibody coupled substrate having anti-Hsp90 antibodies and anti-Topo I antibodies at 4° C. with gentle rotation for 120 minutes to form pH dependent tagged polypeptides bound to the antibody coupled substrate. After 120 minutes, the antibody coupled substrate having anti-Hsp90 antibodies and anti-Topo I antibodies was washed with a wash solution (e.g., 100 mM Hepes pH 8, 500 mM NaCl, 1% IGEPAL) to wash away all unbound tagged polypeptides so that only pH dependent tagged polypeptides were bound that have an affinity to antibodies coupled to the antibody coupled substrate. Next, the pH dependent tagged polypeptides bound to the antibody coupled substrate having anti-Hsp90 antibodies and anti-Topo I antibodies were eluted by treating the antibody coupled substrate with a solution (e.g., 100 mM Hepes pH 8, 100 mM NaCl, 1% SDS) at room temperature with gentle rotation for two separate 10 minute incubations to release the pH dependent tagged polypeptides, thereby forming pH dependent tagged self-antigen polypeptides (i.e. Hsp90 and Topo I) in an eluted sample, as described in Example 4. The eluted sample also contained antibodies that had previously been bound to the antibody coupled substrate. The eluted sample (including the pH dependent tagged self-antigen polypeptides) was added to a second substrate (i.e., TCO beads) as described in Example 4. The self-antigen polypeptides were then eluted from the second substrate as described in Example 5. This elution is represented in lane 4 (Cy3-Eluate) of FIG. 11 and includes purified Hsp90 polypeptides and purified Topo I polypeptides. Lane 1 (Load) of FIG. 11 shows the immunoglobulin fraction eluted from the antibody coupled substrate. Lane 2 (Flow) of FIG. 11 shows the immunoglobulin fraction that did not bind to the second substrate (i.e., TCO beads). Lane 3 (Eluate) of FIG. 11 shows the immunoglobulin fraction eluted from the TCO beads.

The experiment in FIG. 11 demonstrates that the disclosed method of isolating self-antigen polypeptides is capable of isolating and identifying a self-antigen polypeptides with significantly less immunoglobulin contamination in the final purified samples so that the immunoglobulins do not interfere with identification of the self-antigen polypeptide during LC-MS/MS analysis.

Example 13—Capture and Elution of Purified Self-Antigen Peptides

K562 cells (available from ATCC®, Virginia, USA) were centrifuged in a benchtop centrifuge to form a cell pellet. Lysis buffer (100 mM Hepes pH 8, 500 mM NaCl, 1% IGEPAL, 1 mM EDTA, 1 mM Phenylmethylsulfonyl fluoride (PMSF), 10 µg/ml Leupeptin, 10 µg/ml pepstatin) was added to the cell pellet and mixed, thereby forming a K562 cell lysate. The K562 cell lysate was sonicated to break up any DNA present in the lysate. Sonication conditions included: 20 blasts at 30% power, 30% duty cycle, on ice followed by centrifugation at 15,000×g for 20 minutes. The protein concentration of the K562 cell lysate was assayed using BCA Protein Assay.

The K562 cell lysate including 100 µg protein was mixed with 2.1 µl of 30 mg/ml mTet-PEG$_n$-CDM in 90% acetonitrile, 0.1% trifluoracetic acid (see FIG. 2) by pipetting the mixture gently and then incubating it for 30 minutes at 4° C. to form pH dependent tagged polypeptides in the mixed K562 cell lysate.

Free (un-reacted) mTet-PEG$_n$-CDM was quenched by the addition of 20 µl 5M methylamine, 10 mM Hepes pH 8 for 30 minutes at 4° C.

Six different antibody coupled substrates were prepared as follows:

(1) An antibody coupled substrate was prepared by mixing 10 µl of serum from a healthy person with 10 µl of Protein A beads for at least 45 minutes, forming an antibody coupled substrate having antibodies from serum of a healthy person. The antibody coupled substrate was washed with a wash solution (e.g., 100 mM Hepes pH 8, 500 mM NaCl, 1% IGEPAL) to wash away all non-immunoglobulin proteins so that only antibodies from serum of the healthy person were bound to the Protein A beads.

(2) An antibody coupled substrate having anti-Hsp90 antibodies was prepared by mixing 1 µg anti-Hsp90 antibodies with 10 µl of Protein A beads for at least 45 minutes. The antibody coupled substrate having anti-Hsp90 antibodies was washed with a wash solution (e.g., 100 mM Hepes pH 8, 500 mM NaCl, 1% IGEPAL) to wash away all non-immunoglobulin proteins so that only anti-Hsp90 antibodies were bound to the Protein A beads.

(3) An antibody coupled substrate was prepared by mixing 10 µl of scrum from autoimmune patient #1 with 10 µl of Protein A beads for at least 45 minutes, forming an antibody coupled substrate having antibodies from autoimmune patient #1's serum. Autoimmune patient #1's serum includes at least antibodies to Glycine-tRNA ligase. The antibody coupled substrate was washed with a wash solution (e.g., 100 mM Hepes pH 8, 500 mM NaCl, 1% IGEPAL) to wash away all non-immunoglobulin proteins so that only antibodies from autoimmune patient #1's serum were bound to the Protein A beads.

(4) An antibody coupled substrate was prepared by mixing 10 µl of serum from autoimmune patient #2 with 10 µl of Protein A beads for at least 45 minutes, forming an antibody coupled substrate having antibodies from autoimmune patient #2's serum. Autoimmune patient #2's serum includes at least antibodies to DNA topoisomerase. The antibody coupled substrate was washed with a wash solution (e.g., 100 mM Hepes pH 8, 500 mM NaCl, 1% IGEPAL) to wash away all non-immunoglobulin proteins so that only antibodies from autoimmune patient #2's serum were bound to the Protein A beads.

(5) An antibody coupled substrate was prepared by mixing 10 µl of serum from autoimmune patient #3 with 10 µl of Protein A beads for at least 45 minutes, forming an antibody coupled substrate having antibodies from autoimmune patient #3's serum. Autoimmune patient #3's serum includes at least antibodies to Alanine tRNA ligase. The antibody coupled substrate was washed with a wash solution (e.g., 100 mM Hepes pH 8, 500 mM NaCl, 1% IGEPAL) to wash away all non-immunoglobulin proteins so that only antibodies from autoimmune patient #3's serum were bound to the Protein A beads.

(6) An antibody coupled substrate was prepared by mixing 10 µl of serum from autoimmune patient #4 with 10 µl of Protein A beads for at least 45 minutes, forming an antibody coupled substrate having antibodies from autoimmune patient #4's serum. Autoimmune patient #4's serum includes at least antibodies to DNA topoisomerase. The antibody coupled substrate was washed with a wash solution (e.g., 100 mM Hepes pH 8, 500 mM NaCl, 1% IGEPAL) to wash away all non-immunoglobulin proteins so that only antibodies from autoimmune patient #4's serum were bound to the Protein A beads.

A mixed K562 cell lysate (including pH dependent tagged polypeptides) was added to the antibody coupled substrate having antibodies from serum of a healthy person at 4° C. with gentle rotation for 120 minutes to form pH dependent tagged polypeptides bound to the antibody coupled substrate. After 120 minutes, the antibody coupled substrate having antibodies from serum of a healthy person was washed with a wash solution (e.g., 100 mM Hepes pH 8, 500 mM NaCl, 1% IGEPAL) to wash away all unbound tagged polypeptides so that only pH dependent tagged polypeptides were bound that have an affinity to antibodies coupled to the antibody coupled substrate. Next, the pH dependent tagged polypeptides bound to the antibody coupled substrate having antibodies from serum of a healthy person were eluted by treating the antibody coupled substrate with a solution (e.g., 100 mM Hepes pH 8, 100 mM NaCl, 1% SDS) at room temperature with gentle rotation for two separate 10 minute incubations to release the pH dependent tagged polypeptides, thereby forming tagged polypeptides in an eluted sample, as described in Example 4. The eluted sample also contained antibodies that had previously been bound to the antibody coupled substrate. The eluted sample (including the pH dependent tagged polypeptides) was added to a second substrate (e.g. TCO beads) as described in Example 4. The tagged polypeptides were then eluted from the second substrate as described in Example 5, and digested with modified trypsin as described in Example 6, thereby forming peptides, which were further analyzed by LC-MS/MS. Results of this LC-MS/MS analysis were presented in FIG. 12A. FIG. 12A shows that albumin, complement C3, vimentin, apolipoprotein B-100, CD5 antigen-like, alpha-2-macroglobulin, polyadenylate-binding protein 1, tubulin beta chain, actin cytoplasmic 2, and complement C4-B were present in the K562 cell lysate and represent non-specific binding proteins from serum of a healthy person. The information from FIG. 12A demonstrates that these non-specific binding proteins (albumin, complement C3, vimentin, apolipoprotein B-100, CD5 antigen-like, alpha-2-macroglobulin, polyadenylate-binding protein 1, tubulin beta chain, actin cytoplasmic 2, and complement C4-B) are present in immunoprecipitation reactions using serum from a healthy person. The information in FIG. 12A serves as a negative control.

A mixed K562 cell lysate (including pH dependent tagged polypeptides) was added to the antibody coupled substrate having anti-Hsp90-alpha antibodies at 4° C. with gentle rotation for 120 minutes to form pH dependent tagged polypeptides bound to the antibody coupled substrate. After 120 minutes, the antibody coupled substrate having anti-Hsp90 antibodies was washed with a wash solution (e.g., 100 mM Hepes pH 8, 500 mM NaCl, 1% IGEPAL) to wash away all unbound tagged polypeptides so that only pH dependent tagged polypeptides were bound that have an affinity to antibodies coupled to the antibody coupled substrate. Next, the pH dependent tagged polypeptides bound to the antibody coupled substrate having anti-Hsp90-alpha antibodies were eluted by treating the antibody coupled substrate with a solution (e.g., 100 mM Hepes pH 8, 100 mM NaCl, 1% SDS) at room temperature with gentle rotation for two separate 10 minute incubations to release the pH dependent tagged polypeptides, thereby forming tagged polypeptides in an eluted sample, as described in Example 4. The eluted sample also contained antibodies that had previously been bound to the antibody coupled substrate. The eluted sample (including the pH dependent tagged polypeptides) was added to a second substrate (e.g. TCO beads) as described in Example 4. The tagged polypeptides were then eluted from the second substrate as described in Example 5, and digested with modified trypsin as described in Example 6, thereby forming peptides, which were further analyzed by LC-MS/MS analysis were presented in FIG. 12B. FIG. 12B shows the successful identification of Hsp90-alpha in the K562 cell lysate. This sample and the data serve as a positive control. This sample and data also show that many proteins bound non-specifically to the antibody coupled substrate having only anti-Hsp90 antibodies. The proteins that non-specifically bound to the antibody coupled substrate were vimentin, heat shock protein HSP 90-beta, actin cytoplasmic 1, albumin, tubulin beta chain, fatty acid synthase, isoform 3 of plectin, and polyadenylate-binding protein-1.

A mixed K562 cell lysate (including pH dependent tagged polypeptides) was added to the antibody coupled substrate having antibodies from autoimmune patient #1's serum at 4° C. with gentle rotation for 120 minutes to form pH dependent tagged polypeptides bound to the antibody coupled substrate. After 120 minutes, the antibody coupled substrate having antibodies from autoimmune patient #1's serum was washed with a wash solution (e.g., 100 mM Hepes pH 8, 500 mM NaCl, 1% IGEPAL) to wash away all unbound tagged polypeptides so that only pH dependent tagged polypeptides were bound that have an affinity to antibodies coupled to the antibody coupled substrate. Next, the pH dependent tagged polypeptides bound to the antibody coupled substrate having antibodies from autoimmune patient #1's serum were eluted by treating the antibody coupled substrate with a solution (e.g., 100 mM Hepes pH 8, 100 mM NaCl, 1% SDS) at room temperature with gentle rotation for two separate 10 minute incubations to release the pH dependent tagged polypeptides, thereby forming tagged self-antigen polypeptides in an eluted sample, as described in Example 4. The eluted sample also contained antibodies that had previously been bound to the antibody coupled substrate. The eluted sample (including the pH dependent tagged self-antigen polypeptides) was added to a second substrate (e.g. TCO beads) as described in Example 4. The self-antigen polypeptides were then eluted from the second substrate as described in Example 5, and digested with modified trypsin as described in Example 6, thereby forming self-antigen peptides, which were further analyzed by LC-MS/MS. Results of the LC-MS/MS analysis were presented in FIG. 12C, which shows the successful isolation and identification of Glycine-tRNA ligase in the K562 cell lysate. These data in FIG. 12C demonstrate that the autoimmune patient #1's serum includes antibodies to Glycine-tRNA ligase. FIG. 12C also shows that non-specific binding proteins apolipoprotein B-100, albumin, vimentin, complement C3, CD5 antigen-like, complement C4-B, and alpha-2-macroglobulin were present in the K562 cell lysate, but it was previously demonstrated in FIG. 12A that these non-specific binding proteins are also present in serum of a healthy person.

A mixed K562 cell lysate (including pH dependent tagged polypeptides) was added to the antibody coupled substrate having antibodies from autoimmune patient #2's serum at 4° C. with gentle rotation for 120 minutes to form pH dependent tagged polypeptides bound to the antibody coupled substrate. After 120 minutes, the antibody coupled substrate having antibodies from autoimmune patient #2's serum was washed with a wash solution (e.g., 100 mM Hepes pH 8, 500 mM NaCl, 1% IGEPAL) to wash away all unbound tagged polypeptides so that only pH dependent tagged polypeptides were bound that have an affinity to antibodies coupled to the antibody coupled substrate. Next, the pH dependent tagged polypeptides bound to the antibody coupled substrate having antibodies from autoimmune patient #2's serum were eluted by treating the antibody coupled substrate with a solution (e.g., 100 mM Hepes pH 8, 100 mM NaCl, 1% SDS) at room temperature with gentle rotation for two separate 10 minute incubations to release the pH dependent tagged polypeptides, thereby forming tagged self-antigen polypeptides in an eluted sample, as described in Example 4. The eluted sample also contained antibodies that had previously been bound to the antibody coupled substrate. The eluted sample (including the pH dependent tagged self-antigen polypeptides) was added to a second substrate (e.g. TCO beads) as described in Example 4. The self-antigen polypeptides were then eluted from the second substrate as described in Example 5, and digested with modified trypsin as described in Example 6, thereby forming self-antigen peptides, which were further analyzed by LC-MS/MS. Results of the LC-MS/MS analysis were presented in FIG. 12D, which shows the successful identification of DNA topoisomerase 1 in K562 cell lysate. These data in FIG. 12D demonstrate that the autoimmune patient #2's serum includes antibodies to DNA topoisomerase 1. FIG. 12D also shows non-specific binding proteins complement C3, albumin, vimentin, complement C4-B, CD5 antigen-like, polyadenylate-binding protein 1, and apolipoprotein B-100, were present in the K562 cell lysate, but it was previously demonstrated in FIG. 12A that these non-specific binding proteins are also present in serum of a healthy person.

A mixed K562 cell lysate (including pH dependent tagged polypeptides) was added to the antibody coupled substrate having antibodies from autoimmune patient #3's serum at 4° C. with gentle rotation for 120 minutes to form pH dependent tagged polypeptides bound to the antibody coupled substrate. After 120 minutes, the antibody coupled substrate having antibodies from autoimmune patient #3's serum was washed with a wash solution (e.g., 100 mM Hepes pH 8, 500 mM NaCl, 1% IGEPAL) to wash away all unbound tagged polypeptides so that only pH dependent tagged polypeptides were bound that have an affinity to antibodies coupled to the antibody coupled substrate. Next, the pH dependent tagged polypeptides bound to the antibody coupled substrate having antibodies from autoimmune patient #3's serum were eluted by treating the antibody coupled substrate with a solution (e.g., 100 mM Hepes pH 8, 100 mM NaCl, 1% SDS) at room temperature with gentle rotation for two separate 10 minute incubations to release the pH dependent tagged polypeptides, thereby forming tagged self-antigen polypeptides in an eluted sample, as described in Example 4. The eluted sample also contained antibodies that had previously been bound to the antibody coupled substrate. The eluted sample (including the pH dependent tagged self-antigen polypeptides) was added to a second substrate (e.g. TCO beads) as described in Example 4. The self-antigen polypeptides were then eluted from the second substrate as described in Example 5, and digested with modified trypsin as described in Example 6, thereby forming self-antigen peptides, which were further analyzed by LC-MS/MS. Results of this LC-MS/MS analysis were presented in FIG. 12E, which shows the successful identification of Alanine tRNA ligase, cytoplasmic in K562 cell lysate. These data in FIG. 12E demonstrate that the autoimmune patient #3's serum includes antibodies to Alanine tRNA ligase, cytoplasmic. FIG. 12E also shows that non-specific binding proteins albumin, vimentin, complement C3, apolipoprotein B-100, alpha-2-macroglobulin, complement C4-B, CD5 antigen-like, and actin, cytoplasmic 2 were present in the K562 cell lysate, but it was previously demonstrated in FIG. 12A that these non-specific binding proteins are also present in serum of a healthy person.

A mixed K562 cell lysate (including pH dependent tagged polypeptides) was added to the antibody coupled substrate having antibodies from autoimmune patient #4's serum at 4° C. with gentle rotation for 120 minutes to form pH dependent tagged polypeptides bound to the antibody coupled substrate. After 120 minutes, the antibody coupled substrate having antibodies from autoimmune patient #4's serum was washed with a wash solution (e.g., 100 mM Hepes pH 8, 500 mM NaCl, 1% IGEPAL) to wash away all unbound tagged polypeptides so that only pH dependent tagged polypeptides were bound that have an affinity to antibodies coupled to the antibody coupled substrate. Next, the pH dependent tagged polypeptides bound to the antibody coupled substrate having antibodies from autoimmune patient #4's serum were eluted by treating the antibody coupled substrate with a solution (e.g., 100 mM Hepes pH 8, 100 mM NaCl, 1% SDS) at room temperature with gentle rotation for two separate 10 minute incubations to release the pH dependent tagged polypeptides, thereby forming tagged self-antigen polypeptides in an eluted sample, as described in Example 4. The eluted sample also contained antibodies that had previously been bound to the antibody coupled substrate. The eluted sample (including the pH dependent tagged self-antigen polypeptides) was added to a second substrate (e.g. TCO beads) as described in Example 4. The self-antigen polypeptides were then eluted from the second substrate as described in Example 5, and digested with modified trypsin as described in Example 6, thereby forming self-antigen peptides, which were further analyzed by LC-MS/MS. Results of this LC-MS/MS analysis were presented in FIG. 12F, which shows the successful identification of DNA topoisomerase 1 in the K562 cell lysate. These data in FIG. 12F demonstrate that the autoimmune patient #4's serum includes antibodies to DNA topoisomerase 1. These data in FIG. 12F also demonstrated that the autoimmune patient #4's serum includes antibodies to Dihydrolipoyllysine-residue acetyltransferase, which suggests that Dihydrolipoyllysine-residue acetyltransferase is another autoantigen of autoimmune patient #4 (in addition to DNA topoisomerase 1). FIG. 12F also shows non-specific binding proteins vimentin, albumin, CD5 antigen-like, complement C3, actin cytoplasmic 2, and alpha-2-macroglobulin were present in the K562 cell lysate, but it was previously demonstrated in FIG. 12A that these non-specific binding proteins are also present in serum of a healthy person.

Figure 13:
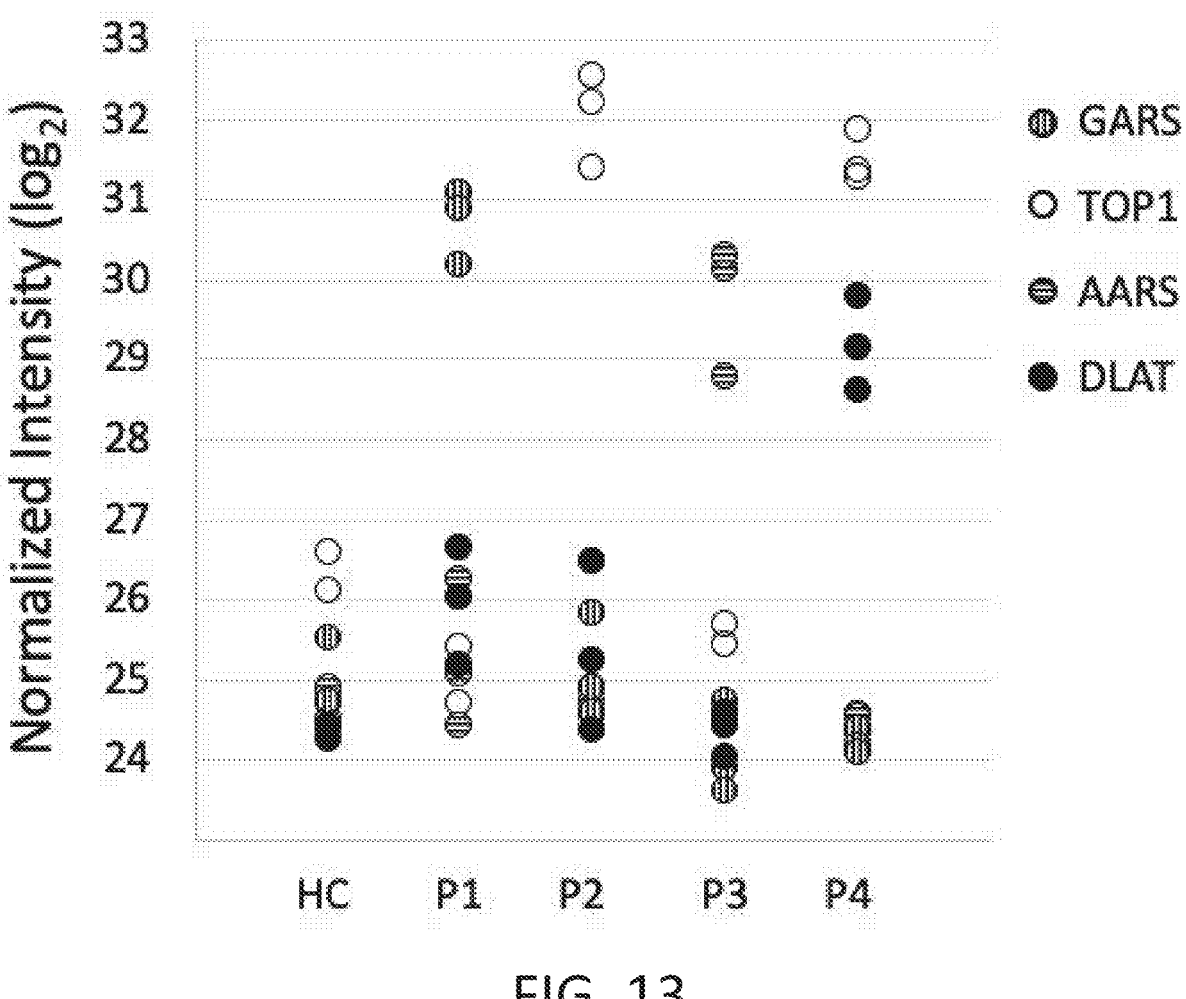
FIG. 13 is a dot plot showing circles that represent antigens identified in FIG. 12A, antigens and autoantigens identified in FIG. 12C, antigens and autoantigens identified in FIG. 12D, antigens and autoantigens identified in FIG. 12E, and antigens and autoantigens identified in FIG. 12F.

FIG. 13 is a dot plot showing autoantigens identified in the healthy person of FIG. 12A, autoimmune patient #1 of FIG. 12C, autoimmune patient #2 of FIG. 12D, autoimmune patient #3 of FIG. 12E, and autoimmune patient #4 of FIG. 12F. Each dot in the dot plot represents a specific autoantigen identified in FIGS. 12A and 12C-F that was recognized as significantly enriched in the immunoprecipitation of each patient's serum. FIG. 13 shows that glycine tRNA ligase (GARS) was greatly enriched in the immunoprecipitation described above using autoimmune patient #1's serum; DNA topoisomerase 1 (TOP1) was greatly enriched in the immunoprecipitation described above using autoimmune patient #2's serum; alanine tRNA ligase, ligase (AARS) was greatly enriched in the immunoprecipitation described above using autoimmune patient #3's serum; and DNA topoisomerase 1 (TOP1) was greatly enriched in the immunoprecipitation described above using autoimmune patient #4's serum. Dihydrolipoyllysine-residue acetyltransferase was also enriched in the immunoprecipitation described above using autoimmune patient #4's serum and is considered another autoantigen in patient #4.

The experiments in FIGS. 12A-12E and FIG. 13 demonstrate that the disclosed method of isolating self-antigen polypeptides is capable of isolating and identifying self-antigen polypeptides and is capable of discriminating non-specific binding proteins from true self-antigens.

Example 14—Capture and Elution of Purified Self-Antigen Polypeptides

Six high-grade serous ovarian carcinoma (HGSOC) cell lines will be used in this experiment including OVCAR3, COV318, OVSAHO, KURAMOCHI, CAOV3, and OVCA433. These cell lines are representative of HGSOC based on features of their genomic profiles, such as TP53 mutational status, mutation frequency, and DNA copy number alterations.

Cells will be centrifuged from each of the HGSOC cell lines in a benchtop centrifuge to form cell pellets. Lysis buffer (100 mM Hepes pH 8, 500 mM NaCl, 1% IGEPAL, 1 mM EDTA, 1 mM Phenylmethylsulfonyl fluoride (PMSF), 10 µg/ml Leupeptin, 10 µg/ml pepstatin) will be added to the cell pellets and mixed, thereby forming cell lysates. The cell lysates will be sonicated to break up any DNA present in the lysate. Sonication conditions include: 20 blasts at 30% power, 30% duty cycle, on ice followed by centrifugation at 15,000×g for 20 minutes. This will result in six different cell lysates: OVCAR3 cell lysate, COV318 cell lysate, OVSAHO cell lysate, KURAMOCHI cell lysate, CAOV3 cell lysate, and OVCA433 cell lysate. The protein concentration of the cell lysates will be assayed using BCA Protein Assay.

Each of the cell lysates including 250 µg protein will be mixed with 2.1 µl of 30 mg/ml mTet-PEG$_n$-CDM in 90% acetonitrile, 0.1% trifluoracetic acid (see FIG. 2) by pipetting the mixture gently and then incubating them for 30 minutes at 4° C. to form pH dependent tagged polypeptides in each of the mixed cell lysates.

Antibody coupled substrates will be prepared as follows:
(1) Blood will be drawn from a healthy age matched woman without cancer and without a history of auto-immunity. Serum will be prepared from the blood as described in Example 1. An antibody coupled substrate will be prepared by mixing 10 µl of serum from the healthy age matched woman with 10 µl of Protein A beads for at least 45 minutes, forming an antibody coupled substrate having antibodies from serum of the healthy woman. The antibody coupled substrate will be washed with a wash solution (e.g., 100 mM Hepes pH 8, 500 mM NaCl, 1% IGEPAL) to wash away all non-immunoglobulin proteins so that only antibodies from serum of the healthy woman will be bound to the Protein A beads. Twenty-five different antibody coupled substrates will be prepared as described in (1) above using serum from 25 different healthy age matched woman without cancer and without a history of autoimmunity. Each of the twenty-five antibody coupled substrates will be coated with antibodies from serum of a different healthy, age matched women.
(2) Blood will be drawn from an age-matched woman with HGSOC before chemotherapy or other treatment is initiated (HGSOC patient). Serum will be prepared from the blood as described in Example 1. An antibody coupled substrate will be prepared by mixing 10 µl of serum from the HGSOC patient with 10 µl of Protein A beads for at least 45 minutes, forming an antibody coupled substrate having antibodies from serum of the HGSOC patient. The antibody coupled substrate will be washed with a wash solution (e.g., 100 mM Hepes pH 8, 500 mM NaCl, 1% IGEPAL) to wash away all non-immunoglobulin proteins so that only antibodies from serum of the HGSOC patient will be bound to the Protein A beads. Twenty-five different antibody coupled substrates will be prepared as described in (2) above using serum from 25 different HGSOC patients. Each of the twenty-five antibody coupled substrates will be coated with antibodies from serum of different HGSOC patients.

Each of the mixed cell lysates (OVCAR3 mixed cell lysate, COV318 mixed cell lysate, OVSAHO mixed cell lysate, KURAMOCHI mixed cell lysate, CAOV3 mixed cell lysate, and OVCA433 mixed cell lysate) will be added to each of the twenty-five different antibody coupled substrates having antibodies from serum of healthy age matched women at 4° C. with gentle rotation for 120 minutes to form pH dependent tagged polypeptides bound to the antibody coupled substrates. After 120 minutes, the antibody coupled substrates having antibodies from serum of healthy age matched women will be washed with a wash solution (e.g., 100 mM Hepes pH 8, 500 mM NaCl, 1% IGEPAL) to wash away all unbound tagged polypeptides so that only pH dependent tagged polypeptides will be bound that have an affinity to antibodies coupled to the antibody coupled substrates. This will result in 125 different antibody coupled substrates being used. Next, the pH dependent tagged polypeptides bound to each of the 125 antibody coupled substrates having antibodies from serum of healthy age matched women will be eluted by treating the antibody coupled substrate with a solution (e.g., 100 mM Hepes pH 8, 100 mM NaCl, 1% SDS) at room temperature with gentle rotation for two separate 10 minute incubations to release the pH dependent tagged polypeptides, thereby forming tagged polypeptides in an eluted sample, as described in Example 4. The eluted samples will also contain antibodies that had previously been bound to the antibody coupled substrates. The eluted sample (including the pH dependent tagged polypeptides) will be added to a second substrate (e.g. TCO beads) as described in Example 4. The tagged polypeptides will then be eluted from the second substrate as described in Example 5, and digested with modified trypsin as described in Example 6, thereby forming peptides, which will be further analyzed by LC-MS/MS. The 125 total samples will be done in triplicate for a total of 450 samples. Results of the LC-MS/MS analysis of the 450 samples will serve as controls to eliminate signals from non-specific protein binding.

Each of the mixed cell lysates (OVCAR3 mixed cell lysate, COV318 mixed cell lysate, OVSAHO mixed cell lysate, KURAMOCHI mixed cell lysate, CAOV3 mixed cell lysate, and OVCA433 mixed cell lysate) will also be added to each of the twenty-five different antibody coupled substrates having antibodies from serum of the HGSOC patients at 4° C. with gentle rotation for 120 minutes to form pH dependent tagged polypeptides bound to the antibody coupled substrates. After 120 minutes, the antibody coupled substrates having antibodies from serum of the HGSOC patients will be washed with a wash solution (e.g., 100 mM Hepes pH 8, 500 mM NaCl, 1% IGEPAL) to wash away all unbound tagged polypeptides so that only pH dependent tagged polypeptides will be bound that have an affinity to antibodies coupled to the antibody coupled substrates. This will result in 125 different antibody coupled substrates being used. Next, the pH dependent tagged polypeptides bound to each of the 125 antibody coupled substrates having antibodies from serum of the HGSOC patients will be eluted by treating the antibody coupled substrates with a solution (e.g., 100 mM Hepes pH 8, 100 mM NaCl, 1% SDS) at room temperature with gentle rotation for two separate 10 minute incubations to release the pH dependent tagged polypeptides, thereby forming tagged self-antigen polypeptides in an eluted sample, as described in Example 4. The eluted samples will also contain antibodies that had previously been bound to the antibody coupled substrates. The eluted sample (including the pH dependent tagged self-antigen polypeptides) will be added to a second substrate (e.g. TCO beads) as described in Example 4. The self-antigen polypeptides will then be eluted from the second substrate as described in Example 5, and digested with modified trypsin as described in Example 6, thereby forming self-antigen peptides, which will be further analyzed by LC-MS/MS. The 125 total samples will be done in triplicate for a total of 450 samples. Results of the LC-MS/MS analysis of the 450 samples will look to identify self-antigen polypeptides (i.e. tumor associated antigens) associated with HGSOC. These data will be instrumental for determining the sample size necessary to identify clinically relevant tumor associated antigens for early diagnosis or recurrence of HGSOC. Applicant hypothesizes that the HGSOC patients will possess circulating antibodies against specific tumor associated antigens originating from the patient's cancer cells. These putative tumor associated antigens will also be expressed by established HGSOC cell lines. The identified tumor associated antigens could potentially serve as biomarkers for ovarian cancer diagnosis.

While the present disclosure provides descriptions of various specific aspects for the purpose of illustrating various examples of the present disclosure and/or its potential applications, it is understood that variations and modifications will occur to those skilled in the art. Accordingly, the invention or inventions described herein should be understood to be at least as broad as they are claimed and not as more narrowly defined by particular illustrative examples provided herein.

What is claimed is:

1. A method of isolating self-antigen polypeptides, the method comprising:
a) and a lysis buffer comprising leupeptin and pepstatin, wherein the compound is bonded to polypeptides in the cell sample by formation of an acid-labile amide bond between a dicarboxylic anhydride of the compound and primary amines of the polypeptides, thereby forming a mixed sample comprising compound bonded polypeptides,
wherein the cell sample comprises self-antigen polypeptides;
wherein the compound comprises
a first moiety comprising a methyltetrazine (mTet);
a second moiety comprising a carboxyl dimethyl maleic anhydride (CDM);
and
a linker linking the first moiety and the second moiety;
b) adding the compound bonded polypeptides in the mixed sample to an antibody coupled substrate, wherein the antibody coupled substrate comprises antibodies from serum of a patient with an autoimmune disorder bound to a bead or solid surface and wherein the compound bonded polypeptides bind to the antibody coupled substrate when the compound bonded polypeptides have an affinity to antibodies on the antibody coupled substrate, thereby forming compound bonded polypeptides bound to the antibody coupled substrate;
c) eluting the compound bonded polypeptides bound to the antibody coupled substrate by adding a solution comprising sodium dodecyl sulfate (SDS), thereby forming compound bonded self-antigen polypeptides in an eluted sample;
d) adding the compound bonded self-antigen polypeptides in the eluted sample to a trans-cyclooctene (TCO), wherein the TCO is linked to a second bead or solid surface, thereby forming self-antigen polypeptides bound to the second bead or solid surface; and
e) eluting the self-antigen polypeptides bound to the second bead or solid surface in an elution buffer having a pH more acidic than a pH of the mixed sample by reversing the acid-labile amide bond between the primary amines of the self-antigen polypeptides and the second moiety comprising a carboxyl dimethyl maleic anhydride (CDM).

2. A method of isolating self-antigen polypeptides, the method comprising:
a) adding compound bonded polypeptides in a mixed sample to an antibody coupled substrate, wherein the compound bonded polypeptides bind to the antibody coupled substrate when the compound bonded polypeptides have an affinity to antibodies on the antibody coupled substrate, thereby forming compound bonded polypeptides bound to the antibody coupled substrate,
wherein the antibody coupled substrate comprises antibodies from serum of a patient with an autoimmune disorder bound to a bead or solid surface, and
wherein the mixed sample comprising compound bonded polypeptides is a and a lysis buffer comprising leupeptin and pepstatin, and the compound is bonded to polypeptides in the cell sample by formation of an acid-labile amide bond between a dicarboxylic anhydride of the compound and primary amines of the polypeptides,
wherein the cell sample comprises self-antigen polypeptides;
wherein the compound comprises
a first moiety comprising a methyltetrazine (mTet);
a second moiety comprising a carboxyl dimethylmaleic anhydride (CDM); and
a linker linking the first moiety and the second moiety;
b) eluting the compound bonded polypeptides bound to the antibody coupled substrate by adding a solution comprising sodium dodecyl sulfate (SDS), thereby forming compound bonded self-antigen polypeptides in an eluted sample;
c) adding the compound bonded self-antigen polypeptides in the eluted sample to a trans-cyclooctene (TCO), wherein the TCO is linked to a second bead or solid surface, thereby forming self-antigen polypeptides bound to the second bead or solid surface; and
d) eluting the self-antigen polypeptides bound to the second bead or solid surface in an elution buffer having a pH more acidic than a pH of the mixed sample by reversing the acid-labile amide bond between the primary amines of the self-antigen polypeptides and the second moiety comprising a carboxyl dimethyl maleic anhydride (CDM).

3. The method of claim 2, further comprising:
mixing the self-antigen polypeptides eluted in the elution buffer with a modified protease, thereby forming a mixed sample comprising self-antigen peptides and the modified protease, wherein the modified protease comprises
a protease; and
a methyltetrazine (mTet) attached to the protease, wherein the mTet forms a covalent bond with a tran-cyclooctene (TCO);
adding the modified protease in the mixed sample to a TCO, wherein the TCO is linked to the second bead or solid surface; and
eluting the self-antigen peptides.

4. The method of claim 3, wherein the modified protease is (i) a modified hydrolase and the protease is a hydrolase;

(ii) a modified serine hydrolase and the protease is a serine hydrolase; or (iii) a modified trypsin and the protease is a trypsin.

5. The method of claim 2, wherein the serum and cell sample are (i) autologous samples;

(ii) allogenic samples;

(iii) the same blood sample; or (iv) different blood samples.

6. The method of claim 2, wherein the self-antigen polypeptides are autoantigens or tumor-associated antigens.

7. The method of claim 2, wherein the linker is an inert linker.

8. The method of claim 2, wherein the bead or solid surface is (i) a magnetic bead;

(ii) a bead contained within a chromatography column or a spin column; or (iii) a protein A bead or protein G bead.

9. The method of claim 2, wherein the second bead or solid surface is (i) a magnetic bead;

(ii) a bead contained within a chromatography column or a spin column; or (iii) a porous matrix.

10. The method of claim 2, wherein the mixed sample has a pH greater than 7.

11. The method of claim 10, wherein the pH greater than 7 ranges from greater than 7 to 10, greater than 7 to 9, or 8 to 9.5.

12. The method of claim 2, wherein the elution buffer having a pH more acidic than a pH of the mixed sample comprises a weak organic acid selected from the group consisting of formic acid, acetic acid, and citric acid.

13. The method of claim 2, wherein the pH more acidic than a pH of the mixed sample ranges from 2 to less than 7, 3 to less than 7, or from 2.5 to 6.

14. The method of claim 2, further comprising washing the compound bonded polypeptides bound to the antibody coupled substrate to remove any unbound materials from the compound bonded polypeptides bound to the antibody coupled substrate.

15. The method of claim 2, further comprising washing the self-antigen polypeptides bound to the second bead or solid surface using a polar aprotic solvent to remove any unbound materials from the self-antigen polypeptides bound to the second bead or solid surface.

16. A method of isolating self-antigen polypeptides, the method comprising:

a) adding compound bonded polypeptides in a mixed sample to an antibody coupled substrate, wherein the compound bonded polypeptides bind to the antibody coupled substrate when the compound bonded polypeptides have an affinity to antibodies on the antibody coupled substrate, thereby forming compound bonded polypeptides bound to the antibody coupled substrate, wherein the antibody coupled substrate comprises antibodies from a biological source of a patient with an autoimmune disorder bound to a bead or solid surface, and wherein the mixed sample comprising compound bonded polypeptides is a and a lysis buffer comprising leupeptin and pepstatin, and the compound is bonded to polypeptides in the cell sample by formation of an acid-labile amide bond between a dicarboxylic anhydride of the compound and primary amines of the polypeptides, wherein the cell sample comprises self-antigen polypeptides;

wherein the compound comprises a first moiety comprising a methyltetrazine (mTet);

a second moiety comprising a carboxyl dimethyl maleic anhydride (CDM); and a linker linking the first moiety and the second moiety;

b) eluting the compound bonded polypeptides bound to the antibody coupled substrate by adding a solution comprising sodium dodecyl sulfate (SDS), thereby forming compound bonded self-antigen polypeptides in an eluted sample;

c) adding the compound bonded self-antigen polypeptides in the eluted sample to a trans-cyclooctene (TCO), wherein the TCO is linked to a second bead or solid surface, thereby forming self-antigen polypeptides bound to the second bead or solid surface; and d) eluting the self-antigen polypeptides bound to the second bead or solid surface in an elution buffer having a pH more acidic than a pH of the mixed sample by reversing the acid-labile amide bond between the primary amines of the self-antigen polypeptides and the second moiety comprising a carboxyl dimethyl maleic anhydride (CDM).

17. The method of claim 1, wherein the cell sample is in a lysis buffer comprising octylphenoxypolyethoxyethanol (IGEPAL), Ethylenediaminetetraacetic acid (EDTA), Phenylmethylsulfonyl fluoride (PMSF), leupeptin, and pepstatin.

18. The method of claim 2, wherein the cell sample is in a lysis buffer comprising octylphenoxypolyethoxyethanol (IGEPAL), Ethylenediaminetetraacetic acid (EDTA), Phenylmethylsulfonyl fluoride (PMSF), leupeptin, and pepstatin.

19. The method of claim 16, wherein the cell sample is in a lysis buffer comprising octylphenoxypolyethoxyethanol (IGEPAL), Ethylenediaminetetraacetic acid (EDTA), Phenylmethylsulfonyl fluoride (PMSF), leupeptin, and pepstatin.

\* \* \* \* \*